(12) United States Patent
Abdul-Hafiz et al.

(10) Patent No.: US 12,727,826 B2
(45) **Date of Patent: *Sep. 8, 2026**

(54) PHYSIOLOGICAL MEASUREMENT DEVICE

(71) Applicant: Masimo Corporation, Irvine, CA (US)

(72) Inventors: Yassir Abdul-Hafiz, Irvine, CA (US); Ammar Al-Ali, San Juan Capistrano, CA (US); Kevin Forrest, Rancho Santa Margarita, CA (US); Eugene Mason, La Habra Heights, CA (US); John Schmidt, Lake Forest, CA (US); Virginia Thanh Ta, Santa Ana, CA (US)

(73) Assignee: Masimo Corporation, Irvine, CA (US)

( * ) Notice: Subject to any disclaimer, the term of this patent is extended or adjusted under 35 U.S.C. 154(b) by 436 days.

This patent is subject to a terminal disclaimer.

(21) Appl. No.: 18/537,677

(22) Filed: Dec. 12, 2023

(65) Prior Publication Data

US 2024/0172996 A1 May 30, 2024

Related U.S. Application Data

(63) Continuation of application No. 17/381,086, filed on Jul. 20, 2021, now Pat. No. 11,877,867, which is a (Continued)

(51) Int. Cl.
*A61B 5/1455* (2006.01)
*A61B 5/00* (2006.01)
(Continued)

(52) U.S. Cl.
CPC .......... *A61B 5/6867* (2013.01); *A61B 5/0205* (2013.01); *A61B 5/02427* (2013.01);
(Continued)

(58) Field of Classification Search
CPC .................................................... A61B 5/1455
See application file for complete search history.

(56) References Cited

U.S. PATENT DOCUMENTS 3,029,682 A 4/1962 Wood
3,815,583 A 6/1974 Scheidt
(Continued)

FOREIGN PATENT DOCUMENTS

CN 2142625 9/1993
CN 200954107 10/2007
(Continued)

OTHER PUBLICATIONS

US 9,579,050 B2, 02/2017, Al-Ali (withdrawn)
(Continued)

*Primary Examiner* — Marjan Fardanesh
(74) *Attorney, Agent, or Firm* — Knobbe, Martens, Olson & Bear, LLP

(57) ABSTRACT

An physiological measurement device provides a device body having a base, legs extending from the base and an optical housing disposed at ends of the legs opposite the base. An optical assembly is disposed in the housing. The device body is flexed so as to position the housing over a tissue site. The device body is unflexed so as to attach the housing to the tissue site and position the optical assembly to illuminate the tissue site. The optical assembly is configured to transmit optical radiation into tissue site tissue and receive the optical radiation after attenuation by pulsatile blood flow within the tissue.

17 Claims, 31 Drawing Sheets

Related U.S. Application Data continuation of application No. 17/360,570, filed on Jun. 28, 2021, now Pat. No. 11,432,771, which is a continuation of application No. 16/377,772, filed on Apr. 8, 2019, now Pat. No. 11,426,125, which is a continuation of application No. 15/417,640, filed on Jan. 27, 2017, now Pat. No. 10,292,657, which is a continuation of application No. 14/218,328, filed on Mar. 18, 2014, now abandoned, which is a continuation of application No. 13/975,008, filed on Aug. 23, 2013, now Pat. No. 9,259,185, which is a continuation of application No. 12/658,872, filed on Feb. 16, 2010, now Pat. No. 8,588,880.

(60) Provisional application No. 61/152,964, filed on Feb. 16, 2009.

(51) Int. Cl.
*A61B 5/0205* (2006.01)
*A61B 5/024* (2006.01)
*A61B 5/026* (2006.01)

(52) U.S. Cl.
CPC .......... *A61B 5/0261* (2013.01); *A61B 5/1455* (2013.01); *A61B 5/14552* (2013.01); *A61B 5/6815* (2013.01); *A61B 5/6816* (2013.01); *A61B 5/6817* (2013.01); *A61B 5/6838* (2013.01)

(56) References Cited

U.S. PATENT DOCUMENTS 3,909,556 A 9/1975 Johanson
3,975,599 A 8/1976 Johanson
4,550,227 A 10/1985 Topholm
4,629,833 A 12/1986 Kern et al.
4,638,125 A 1/1987 Buettner
4,680,799 A 7/1987 Henneberger
4,689,819 A 8/1987 Killion
4,723,293 A 2/1988 Harless
4,739,512 A 4/1988 Hartl et al.
4,764,957 A 8/1988 Angelini et al.
4,955,729 A 9/1990 Marx
4,960,128 A 10/1990 Gordon et al.
4,964,408 A 10/1990 Hink et al.
4,985,925 A 1/1991 Langberg et al.
5,003,608 A 3/1991 Carlson
5,041,187 A 8/1991 Hink et al.
5,069,213 A 12/1991 Hink et al.
5,163,438 A 11/1992 Gordon et al.
5,210,803 A 5/1993 Martin et al.
5,213,099 A 5/1993 Tripp, Jr.
5,228,089 A 7/1993 Inanaga et al.
5,239,588 A 8/1993 Davis
5,319,355 A 6/1994 Russek
5,333,622 A 8/1994 Casali et al.
5,337,744 A 8/1994 Branigan
5,341,805 A 8/1994 Stavridi et al.
D353,195 S 12/1994 Savage et al.
D353,196 S 12/1994 Savage et al.
5,372,134 A 12/1994 Richardson
5,377,676 A 1/1995 Vari et al.
D359,546 S 6/1995 Savage et al.
5,431,170 A 7/1995 Mathews
5,436,499 A 7/1995 Namavar et al.
D361,840 S 8/1995 Savage et al.
D362,063 S 9/1995 Savage et al.
5,452,717 A 9/1995 Branigan et al.
D363,120 S 10/1995 Savage et al.
5,456,252 A 10/1995 Vari et al.
5,479,934 A 1/1996 Imran
5,482,036 A 1/1996 Diab et al.
5,490,505 A 2/1996 Diab et al.
5,494,043 A 2/1996 O'Sullivan et al.
5,524,150 A 6/1996 Sauer
5,533,511 A 7/1996 Kaspari et al.
5,534,851 A 7/1996 Russek
5,561,275 A 10/1996 Savage et al.
5,562,002 A 10/1996 Lalin
5,590,649 A 1/1997 Caro et al.
5,602,924 A 2/1997 Durand et al.
5,632,272 A 5/1997 Diab et al.
5,638,816 A 6/1997 Kiani-Azarbayjany et al.
5,638,818 A 6/1997 Diab et al.
5,642,426 A 6/1997 Neuman et al.
5,645,440 A 7/1997 Tobler et al.
5,659,621 A 8/1997 Newton
5,671,914 A 9/1997 Kalkhoran et al.
5,673,692 A 10/1997 Schulze et al.
5,685,299 A 11/1997 Diab et al.
5,721,783 A 2/1998 Anderson
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,810,734 A 9/1998 Caro et al.
5,823,950 A 10/1998 Diab et al.
5,830,131 A 11/1998 Caro et al.
5,833,618 A 11/1998 Caro et al.
5,860,919 A 1/1999 Kiani-Azarbayjany et al.
5,890,929 A 4/1999 Mills et al.
5,904,654 A 5/1999 Wohltmann et al.
5,919,134 A 7/1999 Diab
5,934,925 A 8/1999 Tobler et al.
5,940,182 A 8/1999 Lepper, Jr. et al.
5,987,343 A 11/1999 Kinast
5,995,855 A 11/1999 Kiani et al.
5,997,343 A 12/1999 Mills et al.
6,002,952 A 12/1999 Diab et al.
6,010,937 A 1/2000 Karam et al.
6,011,986 A 1/2000 Diab et al.
6,027,452 A 2/2000 Flaherty et al.
6,036,642 A 3/2000 Diab et al.
6,040,578 A 3/2000 Malin et al.
6,045,509 A 4/2000 Caro et al.
6,066,204 A 5/2000 Haven
6,067,462 A 5/2000 Diab et al.
6,078,829 A 6/2000 Uchida
6,080,110 A 6/2000 Thorgersen
6,081,735 A 6/2000 Diab et al.
6,088,607 A 7/2000 Diab et al.
6,110,522 A 8/2000 Lepper, Jr. et al.
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,184,521 B1 2/2001 Coffin, IV et al.
6,206,830 B1 3/2001 Diab et al.
6,229,856 B1 5/2001 Diab et al.
6,232,609 B1 5/2001 Snyder et al.
6,236,872 B1 5/2001 Diab et al.
6,241,683 B1 6/2001 Macklem et al.
6,253,097 B1 6/2001 Aronow et al.
6,255,708 B1 7/2001 Sudharsanan et al.
6,256,523 B1 7/2001 Diab et al.
6,263,222 B1 7/2001 Diab et al.
6,278,522 B1 8/2001 Lepper, Jr. et al.
6,280,213 B1 8/2001 Tobler et al.
6,280,381 B1 8/2001 Malin et al.
6,285,896 B1 9/2001 Tobler et al.

(56) References Cited

U.S. PATENT DOCUMENTS 6,301,493 B1 10/2001 Marro et al.
6,308,089 B1 10/2001 von der Ruhr et al.
6,317,627 B1 11/2001 Ennen et al.
6,321,100 B1 11/2001 Parker
6,325,761 B1 12/2001 Jay
6,334,065 B1 12/2001 Al-Ali et al.
6,343,224 B1 1/2002 Parker
6,349,228 B1 2/2002 Kiani et al.
6,360,114 B1 3/2002 Diab et al.
6,368,283 B1 4/2002 Xu et al.
6,371,921 B1 4/2002 Caro et al.
6,377,829 B1 4/2002 Al-Ali
6,388,240 B2 5/2002 Schulz et al.
6,397,091 B2 5/2002 Diab et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,501,975 B2 12/2002 Diab et al.
6,505,059 B1 1/2003 Kollias et al.
6,515,273 B2 2/2003 Al-Ali
6,519,487 B1 2/2003 Parker
6,525,386 B1 2/2003 Mills et al.
6,526,300 B1 2/2003 Kiani et al.
6,534,012 B1 3/2003 Hazen et al.
6,541,756 B2 4/2003 Schulz et al.
6,542,764 B1 4/2003 Al-Ali et al.
6,556,852 B1 4/2003 Schulze et al.
6,580,086 B1 6/2003 Schulz et al.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,597,933 B2 7/2003 Kiani et al.
6,606,511 B1 8/2003 Ali et al.
6,632,181 B2 10/2003 Flaherty et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,643,530 B2 11/2003 Diab et al.
6,650,917 B2 11/2003 Diab et al.
6,654,624 B2 11/2003 Diab et al.
6,658,276 B2 12/2003 Kiani et al.
6,661,161 B1 12/2003 Lanzo et al.
6,671,531 B2 12/2003 Al-Ali
6,678,543 B2 1/2004 Diab et al.
6,684,090 B2 1/2004 Ali et al.
6,684,091 B2 1/2004 Parker
6,697,656 B1 2/2004 Al-Ali
6,697,657 B1 2/2004 Shehada et al.
6,697,658 B2 2/2004 Al-Ali
RE38,476 E 3/2004 Diab et al.
6,699,194 B1 3/2004 Diab et al.
6,714,804 B2 3/2004 Al-Ali et al.
RE38,492 E 4/2004 Diab et al.
6,721,582 B2 4/2004 Trepagnier et al.
6,721,585 B1 4/2004 Parker
6,725,075 B2 4/2004 Al-Ali
6,728,560 B2 4/2004 Kollias et al.
6,735,459 B2 5/2004 Parker
6,738,652 B2 5/2004 Mattu et al.
6,745,060 B2 6/2004 Diab et al.
6,745,764 B2 6/2004 Hickle
6,760,607 B2 7/2004 Al-Ali
D495,317 S 8/2004 Sugioka et al.
6,770,028 B1 8/2004 Ali et al.
6,771,994 B2 8/2004 Kiani et al.
6,788,965 B2 9/2004 Ruchti et al.
6,792,300 B1 9/2004 Diab et al.
6,808,473 B2 10/2004 Hisano et al.
6,813,511 B2 11/2004 Diab et al.
6,816,241 B2 11/2004 Grubisic
6,816,741 B2 11/2004 Diab
6,822,564 B2 11/2004 Al-Ali
6,826,419 B2 11/2004 Diab et al.
6,830,711 B2 12/2004 Mills et al.
6,850,787 B2 2/2005 Weber et al.
6,850,788 B2 2/2005 Al-Ali
6,852,083 B2 2/2005 Caro et al.
6,861,639 B2 3/2005 Al-Ali
6,876,931 B2 4/2005 Lorenz et al.
6,898,452 B2 5/2005 Al-Ali et al.
6,920,345 B2 7/2005 Al-Ali et al.
6,931,268 B1 8/2005 Kiani-Azarbayjany et al.
6,934,570 B2 8/2005 Kiani et al.
6,939,305 B2 9/2005 Flaherty et al.
6,943,348 B1 9/2005 Coffin, IV
6,950,687 B2 9/2005 Al-Ali
6,956,649 B2 10/2005 Acosta et al.
6,961,598 B2 11/2005 Diab
6,970,792 B1 11/2005 Diab
6,979,812 B2 12/2005 Al-Ali
6,985,764 B2 1/2006 Mason et al.
6,990,364 B2 1/2006 Ruchti et al.
6,993,371 B2 1/2006 Kiani et al.
6,996,427 B2 2/2006 Ali et al.
6,998,247 B2 2/2006 Monfre et al.
6,999,904 B2 2/2006 Weber et al.
7,003,338 B2 2/2006 Weber et al.
7,003,339 B2 2/2006 Diab et al.
7,015,451 B2 3/2006 Dalke et al.
7,024,233 B2 4/2006 Ali et al.
7,027,849 B2 4/2006 Al-Ali
7,030,749 B2 4/2006 Al-Ali
7,039,449 B2 5/2006 Al-Ali
7,041,060 B2 5/2006 Flaherty et al.
7,044,918 B2 5/2006 Diab
7,048,687 B1 5/2006 Reuss et al.
7,067,893 B2 6/2006 Mills et al.
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,132,641 B2 11/2006 Schulz et al.
7,133,710 B2 11/2006 Acosta et al.
7,142,901 B2 11/2006 Kiani et al.
7,149,561 B2 12/2006 Diab
7,175,601 B2 2/2007 Verjus et al.
7,186,966 B2 3/2007 Al-Ali
7,190,261 B2 3/2007 Al-Ali
7,209,775 B2 4/2007 Bae et al.
7,215,984 B2 5/2007 Diab et al.
7,215,986 B2 5/2007 Diab et al.
7,221,971 B2 5/2007 Diab et al.
7,225,006 B2 5/2007 Al-Ali et al.
7,225,007 B2 5/2007 Al-Ali et al.
RE39,672 E 6/2007 Shehada et al.
7,239,905 B2 7/2007 Kiani-Azarbayjany et al.
7,245,953 B1 7/2007 Parker
7,254,429 B2 8/2007 Schurman et al.
7,254,431 B2 8/2007 Al-Ali et al.
7,254,433 B2 8/2007 Diab et al.
7,254,434 B2 8/2007 Schulz et al.
7,263,396 B2 8/2007 Chen et al.
7,272,425 B2 9/2007 Al-Ali
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,295,866 B2 11/2007 Al-Ali
7,328,053 B1 2/2008 Diab et al.
7,332,784 B2 2/2008 Mills et al.
7,340,287 B2 3/2008 Mason et al.
7,341,559 B2 3/2008 Schulz et al.
7,343,186 B2 3/2008 Lamego et al.
D566,282 S 4/2008 Al-Ali et al.
7,355,512 B1 4/2008 Al-Ali
7,356,365 B2 4/2008 Schurman

(56) References Cited

U.S. PATENT DOCUMENTS 7,371,981 B2 5/2008 Abdul-Hafiz
7,373,193 B2 5/2008 Al-Ali et al.
7,373,194 B2 5/2008 Weber et al.
7,376,453 B1 5/2008 Diab et al.
7,377,794 B2 5/2008 Al-Ali et al.
7,377,899 B2 5/2008 Weber et al.
7,383,070 B2 6/2008 Diab et al.
7,386,347 B2 6/2008 Chung et al.
7,395,158 B2 7/2008 Monfre et al.
7,412,272 B2 8/2008 Medina
7,415,297 B2 8/2008 Al-Ali et al.
7,428,432 B2 9/2008 Ali et al.
7,438,683 B2 10/2008 Al-Ali et al.
7,440,787 B2 10/2008 Diab
7,454,240 B2 11/2008 Diab et al.
7,467,002 B2 12/2008 Weber et al.
7,469,157 B2 12/2008 Diab et al.
7,471,969 B2 12/2008 Diab et al.
7,471,971 B2 12/2008 Diab et al.
7,483,729 B2 1/2009 Al-Ali et al.
7,483,730 B2 1/2009 Diab et al.
7,489,958 B2 2/2009 Diab et al.
7,496,391 B2 2/2009 Diab et al.
7,496,393 B2 2/2009 Diab et al.
D587,657 S 3/2009 Al-Ali et al.
7,499,741 B2 3/2009 Diab et al.
7,499,835 B2 3/2009 Weber et al.
7,500,950 B2 3/2009 Al-Ali et al.
7,509,154 B2 3/2009 Diab et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
7,522,739 B2 4/2009 Rass et al.
7,526,328 B2 4/2009 Diab et al.
D592,507 S 5/2009 Wachman et al.
7,530,942 B1 5/2009 Diab
7,530,949 B2 5/2009 Al Ali et al.
7,530,955 B2 5/2009 Diab et al.
7,563,110 B2 7/2009 Al-Ali et al.
7,593,230 B2 9/2009 Abul-Haj et al.
7,596,398 B2 9/2009 Al-Ali et al.
7,606,608 B2 10/2009 Blank et al.
7,618,375 B2 11/2009 Flaherty et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,734,320 B2 6/2010 Al-Ali
7,761,127 B2 7/2010 Al-Ali et al.
7,761,128 B2 7/2010 Al-Ali et al.
7,764,982 B2 7/2010 Dalke et al.
D621,516 S 8/2010 Kiani et al.
7,769,435 B2 8/2010 Kuo et al.
7,791,155 B2 9/2010 Diab
7,801,581 B2 9/2010 Diab
7,822,452 B2 10/2010 Schurman et al.
RE41,912 E 11/2010 Parker
7,844,313 B2 11/2010 Kiani et al.
7,844,314 B2 11/2010 Al-Ali
7,844,315 B2 11/2010 Al-Ali
7,865,222 B2 1/2011 Weber et al.
7,873,497 B2 1/2011 Weber et al.
7,880,606 B2 2/2011 Al-Ali
7,880,626 B2 2/2011 Al-Ali et al.
7,891,355 B2 2/2011 Al-Ali et al.
7,894,868 B2 2/2011 Al-Ali et al.
7,899,507 B2 3/2011 Al-Ali et al.
7,899,518 B2 3/2011 Trepagnier et al.
7,904,132 B2 3/2011 Weber et al.
7,909,772 B2 3/2011 Popov et al.
7,910,875 B2 3/2011 Al-Ali
7,914,468 B2 3/2011 Shalon et al.
7,919,713 B2 4/2011 Al-Ali et al.
7,937,128 B2 5/2011 Al-Ali
7,937,129 B2 5/2011 Mason et al.
7,937,130 B2 5/2011 Diab et al.
7,941,199 B2 5/2011 Kiani
7,951,086 B2 5/2011 Flaherty et al.
7,957,780 B2 6/2011 Lamego et al.
7,962,188 B2 6/2011 Kiani et al.
7,962,190 B1 6/2011 Diab et al.
7,976,472 B2 7/2011 Kiani
7,986,803 B1 7/2011 DeKalb
7,988,637 B2 8/2011 Diab
7,990,382 B2 8/2011 Kiani
7,991,446 B2 8/2011 Ali et al.
8,000,761 B2 8/2011 Al-Ali
8,008,088 B2 8/2011 Bellott et al.
RE42,753 E 9/2011 Kiani-Azarbayjany et al.
8,019,400 B2 9/2011 Diab et al.
8,028,701 B2 10/2011 Al-Ali et al.
8,029,765 B2 10/2011 Bellott et al.
8,036,727 B2 10/2011 Schurman et al.
8,036,728 B2 10/2011 Diab et al.
8,046,040 B2 10/2011 Ali et al.
8,046,041 B2 10/2011 Diab et al.
8,046,042 B2 10/2011 Diab et al.
8,048,040 B2 11/2011 Kiani
8,050,728 B2 11/2011 Al-Ali et al.
8,108,036 B2 1/2012 Tran
RE43,169 E 2/2012 Parker
8,118,620 B2 2/2012 Al-Ali et al.
8,126,528 B2 2/2012 Diab et al.
8,128,572 B2 3/2012 Diab et al.
8,130,105 B2 3/2012 Al-Ali et al.
8,145,287 B2 3/2012 Diab et al.
8,150,487 B2 4/2012 Diab et al.
8,175,672 B2 5/2012 Parker
8,180,420 B2 5/2012 Diab et al.
8,182,443 B1 5/2012 Kiani
8,185,180 B2 5/2012 Diab et al.
8,190,223 B2 5/2012 Al-Ali et al.
8,190,227 B2 5/2012 Diab et al.
8,199,956 B2 6/2012 Haartsen et al.
8,203,438 B2 6/2012 Kiani et al.
8,203,704 B2 6/2012 Merritt et al.
8,204,566 B2 6/2012 Schurman et al.
8,219,172 B2 7/2012 Schurman et al.
8,224,411 B2 7/2012 Al-Ali et al.
8,228,181 B2 7/2012 Al-Ali
8,229,532 B2 7/2012 Davis
8,229,533 B2 7/2012 Diab et al.
8,233,955 B2 7/2012 Al-Ali et al.
8,244,325 B2 8/2012 Al-Ali et al.
8,251,903 B2 8/2012 LeBoeuf et al.
8,255,026 B1 8/2012 Al-Ali
8,255,027 B2 8/2012 Al-Ali et al.
8,255,028 B2 8/2012 Al-Ali et al.
8,260,577 B2 9/2012 Weber et al.
8,265,723 B1 9/2012 McHale et al.
8,271,075 B2 9/2012 Chuang et al.
8,274,360 B2 9/2012 Sampath et al.
8,280,473 B2 10/2012 Al-Ali
8,301,217 B2 10/2012 Al-Ali et al.
8,306,596 B2 11/2012 Schurman et al.
8,310,336 B2 11/2012 Muhsin et al.
8,315,683 B2 11/2012 Al-Ali et al.
8,320,982 B2 11/2012 LeBoeuf et al.
RE43,860 E 12/2012 Parker
8,337,403 B2 12/2012 Al-Ali et al.
8,346,330 B2 1/2013 Lamego
8,353,842 B2 1/2013 Al-Ali et al.
8,355,766 B2 1/2013 MacNeish, III et al.
8,359,080 B2 1/2013 Diab et al.
8,364,223 B2 1/2013 Al-Ali et al.

(56) References Cited

U.S. PATENT DOCUMENTS 8,364,226 B2 1/2013 Diab et al.
8,374,375 B2 2/2013 Hu
8,374,665 B2 2/2013 Lamego
8,385,995 B2 2/2013 Al-Ali et al.
8,385,996 B2 2/2013 Smith et al.
8,388,353 B2 3/2013 Kiani et al.
8,399,822 B2 3/2013 Al-Ali
8,401,602 B2 3/2013 Kiani
8,405,608 B2 3/2013 Al-Ali et al.
8,406,447 B2 3/2013 Kromann et al.
8,414,499 B2 4/2013 Al-Ali et al.
8,418,524 B2 4/2013 Al-Ali
8,423,106 B2 4/2013 Lamego et al.
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,703 B2 6/2013 Al-Ali
8,457,707 B2 6/2013 Kiani
8,463,349 B2 6/2013 Diab et al.
8,466,286 B2 6/2013 Bellott et al.
8,471,713 B2 6/2013 Poeze et al.
8,473,020 B2 6/2013 Kiani et al.
8,483,787 B2 7/2013 Al-Ali et al.
8,489,364 B2 7/2013 Weber et al.
8,498,439 B2 7/2013 Bae et al.
8,498,684 B2 7/2013 Weber et al.
8,504,128 B2 8/2013 Blank et al.
8,506,469 B2 8/2013 Dietrich et al.
8,509,867 B2 8/2013 Workman et al.
8,515,509 B2 8/2013 Bruinsma et al.
8,523,781 B2 9/2013 Al-Ali
8,529,301 B2 9/2013 Al-Ali et al.
8,532,727 B2 9/2013 Ali et al.
8,532,728 B2 9/2013 Diab et al.
D692,145 S 10/2013 Al-Ali et al.
8,547,209 B2 10/2013 Kiani et al.
8,548,548 B2 10/2013 Al-Ali
8,548,549 B2 10/2013 Schurman et al.
8,548,550 B2 10/2013 Al-Ali et al.
8,560,032 B2 10/2013 Al-Ali et al.
8,560,034 B1 10/2013 Diab et al.
8,570,167 B2 10/2013 Al-Ali
8,570,503 B2 10/2013 Vo et al.
8,571,617 B2 10/2013 Reichgott et al.
8,571,618 B1 10/2013 Lamego et al.
8,571,619 B2 10/2013 Al-Ali et al.
8,574,165 B2 11/2013 Marsh
8,577,431 B2 11/2013 Lamego et al.
8,581,732 B2 11/2013 Al-Ali et al.
8,584,345 B2 11/2013 Al-Ali et al.
8,588,880 B2 11/2013 Abdul-Hafiz et al.
8,600,467 B2 12/2013 Al-Ali et al.
8,606,342 B2 12/2013 Diab
8,626,255 B2 1/2014 Al-Ali et al.
8,630,436 B2 1/2014 Berg
8,630,691 B2 1/2014 Lamego et al.
8,634,889 B2 1/2014 Al-Ali et al.
8,641,631 B2 2/2014 Sierra et al.
8,647,270 B2 2/2014 LeBoeuf et al.
8,652,040 B2 2/2014 LeBoeuf et al.
8,652,060 B2 2/2014 Al-Ali
8,663,107 B2 3/2014 Kiani
8,666,468 B1 3/2014 Al-Ali
8,667,967 B2 3/2014 Al-Ali et al.
8,670,811 B2 3/2014 O'Reilly
8,670,814 B2 3/2014 Diab et al.
8,676,286 B2 3/2014 Weber et al.
8,682,407 B2 3/2014 Al-Ali
RE44,823 E 4/2014 Parker
RE44,875 E 4/2014 Kiani et al.
8,688,183 B2 4/2014 Bruinsma et al.
8,690,799 B2 4/2014 Telfort et al.
8,700,112 B2 4/2014 Kiani
8,702,627 B2 4/2014 Telfort et al.
8,706,179 B2 4/2014 Parker
8,712,494 B1 4/2014 MacNeish et al.
8,715,206 B2 5/2014 Telfort et al.
8,718,735 B2 5/2014 Lamego et al.
8,718,737 B2 5/2014 Diab et al.
8,718,738 B2 5/2014 Blank et al.
8,718,980 B2 5/2014 Garudadri et al.
8,720,249 B2 5/2014 Al-Ali
8,721,541 B2 5/2014 Al-Ali et al.
8,721,542 B2 5/2014 Al-Ali et al.
8,723,677 B1 5/2014 Kiani
8,737,669 B2 5/2014 Monahan et al.
8,740,792 B1 6/2014 Kiani et al.
8,754,776 B2 6/2014 Poeze et al.
8,755,535 B2 6/2014 Telfort et al.
8,755,856 B2 6/2014 Diab et al.
8,755,872 B1 6/2014 Marinow
8,761,850 B2 6/2014 Lamego
8,764,671 B2 7/2014 Kiani
8,768,423 B2 7/2014 Shakespeare et al.
8,771,204 B2 7/2014 Telfort et al.
8,774,435 B2 7/2014 Ambrose et al.
8,777,634 B2 7/2014 Kiani et al.
8,781,543 B2 7/2014 Diab et al.
8,781,544 B2 7/2014 Al-Ali et al.
8,781,549 B2 7/2014 Al-Ali et al.
8,788,003 B2 7/2014 Schurman et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,831,700 B2 9/2014 Schurman et al.
8,840,549 B2 9/2014 Al-Ali et al.
8,847,740 B2 9/2014 Kiani et al.
8,849,365 B2 9/2014 Smith et al.
8,852,094 B2 10/2014 Al-Ali et al.
8,852,994 B2 10/2014 Wojtczuk et al.
8,868,147 B2 10/2014 Stippick et al.
8,868,150 B2 10/2014 Al-Ali et al.
8,870,792 B2 10/2014 Al-Ali et al.
8,886,271 B2 11/2014 Kiani et al.
8,888,539 B2 11/2014 Al-Ali et al.
8,888,708 B2 11/2014 Diab et al.
8,892,180 B2 11/2014 Weber et al.
8,897,847 B2 11/2014 Al-Ali
8,897,859 B2 11/2014 Shimuta et al.
8,909,310 B2 12/2014 Lamego et al.
8,911,377 B2 12/2014 Al-Ali
8,912,909 B2 12/2014 Al-Ali et al.
8,920,317 B2 12/2014 Al-Ali et al.
8,921,699 B2 12/2014 Al-Ali et al.
8,922,382 B2 12/2014 Al-Ali et al.
8,923,918 B2 12/2014 Kreger et al.
8,929,964 B2 1/2015 Al-Ali et al.
8,942,777 B2 1/2015 Diab et al.
8,948,834 B2 2/2015 Diab et al.
8,948,835 B2 2/2015 Diab
8,965,471 B2 2/2015 Lamego
8,983,564 B2 3/2015 Al-Ali
8,989,831 B2 3/2015 Al-Ali et al.
8,996,085 B2 3/2015 Kiani et al.
8,998,809 B2 4/2015 Kiani
9,028,429 B2 5/2015 Telfort et al.
9,037,207 B2 5/2015 Al-Ali et al.
9,060,721 B2 6/2015 Reichgott et al.
9,066,666 B2 6/2015 Kiani
9,066,680 B1 6/2015 Al-Ali et al.
9,072,474 B2 7/2015 Al-Ali et al.
9,078,560 B2 7/2015 Schurman et al.
9,082,388 B2 7/2015 Annunziato et al.
9,084,569 B2 7/2015 Weber et al.
9,095,316 B2 8/2015 Welch et al.
9,106,038 B2 8/2015 Telfort et al.
9,107,625 B2 8/2015 Telfort et al.
9,107,626 B2 8/2015 Al-Ali et al.
9,113,831 B2 8/2015 Al-Ali
9,113,832 B2 8/2015 Al-Ali
9,119,595 B2 9/2015 Lamego

(56) References Cited

U.S. PATENT DOCUMENTS 9,131,881 B2 9/2015 Diab et al.
9,131,882 B2 9/2015 Al-Ali et al.
9,131,883 B2 9/2015 Al-Ali
9,131,917 B2 9/2015 Telfort et al.
9,138,180 B1 9/2015 Coverston et al.
9,138,182 B2 9/2015 Al-Ali et al.
9,138,192 B2 9/2015 Weber et al.
9,142,117 B2 9/2015 Muhsin et al.
D740,255 S 10/2015 Samrelius
9,153,112 B1 10/2015 Kiani et al.
9,153,121 B2 10/2015 Kiani et al.
9,161,114 B2 10/2015 Bone et al.
9,161,696 B2 10/2015 Al-Ali et al.
9,161,713 B2 10/2015 Al-Ali et al.
9,167,995 B2 10/2015 Lamego et al.
9,176,141 B2 11/2015 Al-Ali et al.
9,186,102 B2 11/2015 Bruinsma et al.
9,192,312 B2 11/2015 Al-Ali
9,192,329 B2 11/2015 Al-Ali
9,192,351 B1 11/2015 Telfort et al.
9,195,385 B2 11/2015 Al-Ali et al.
9,211,072 B2 12/2015 Kiani
9,211,095 B1 12/2015 Al-Ali
9,218,454 B2 12/2015 Kiani et al.
9,226,696 B2 1/2016 Kiani
9,241,662 B2 1/2016 Al-Ali et al.
9,245,668 B1 1/2016 Vo et al.
9,259,185 B2 2/2016 Abdul-Hafiz et al.
9,267,572 B2 2/2016 Barker et al.
9,277,880 B2 3/2016 Poeze et al.
9,289,167 B2 3/2016 Diab et al.
9,295,421 B2 3/2016 Kiani et al.
9,307,928 B1 4/2016 Al-Ali et al.
9,313,585 B2 4/2016 Lunner
9,323,894 B2 4/2016 Kiani
9,323,899 B2 4/2016 Goldstein
D755,392 S 5/2016 Hwang et al.
9,326,712 B1 5/2016 Kiani
9,333,316 B2 5/2016 Kiani
9,339,220 B2 5/2016 Lamego et al.
9,341,565 B2 5/2016 Lamego et al.
9,351,673 B2 5/2016 Diab et al.
9,351,675 B2 5/2016 Al-Ali et al.
9,364,181 B2 6/2016 Kiani et al.
9,368,671 B2 6/2016 Wojtczuk et al.
9,370,325 B2 6/2016 Al-Ali et al.
9,370,326 B2 6/2016 McHale et al.
9,370,335 B2 6/2016 Al-Ali et al.
9,375,185 B2 6/2016 Ali et al.
9,386,953 B2 7/2016 Al-Ali
9,386,961 B2 7/2016 Al-Ali et al.
9,392,945 B2 7/2016 Al-Ali et al.
9,397,448 B2 7/2016 Al-Ali et al.
9,398,891 B2 7/2016 Bagha
9,408,542 B1 8/2016 Kinast et al.
9,436,645 B2 9/2016 Al-Ali et al.
9,438,294 B2 9/2016 Boesen
9,445,759 B1 9/2016 Lamego et al.
9,466,919 B2 10/2016 Kiani et al.
9,474,474 B2 10/2016 Lamego et al.
9,480,422 B2 11/2016 Al-Ali
9,480,435 B2 11/2016 Olsen
9,492,110 B2 11/2016 Al-Ali et al.
9,510,779 B2 12/2016 Poeze et al.
9,517,024 B2 12/2016 Kiani et al.
9,532,722 B2 1/2017 Lamego et al.
9,538,949 B2 1/2017 Al-Ali et al.
9,538,980 B2 1/2017 Telfort et al.
9,549,696 B2 1/2017 Lamego et al.
9,554,737 B2 1/2017 Schurman et al.
9,560,996 B2 2/2017 Kiani
9,560,998 B2 2/2017 Al-Ali et al.
9,566,019 B2 2/2017 Al-Ali et al.
9,579,039 B2 2/2017 Jansen et al.
9,591,975 B2 3/2017 Dalvi et al.
9,602,938 B2 3/2017 Goldstein et al.
9,622,692 B2 4/2017 Lamego et al.
9,622,693 B2 4/2017 Diab
D788,312 S 5/2017 Al-Ali et al.
9,636,055 B2 5/2017 Al Ali et al.
9,636,056 B2 5/2017 Al-Ali
9,649,054 B2 5/2017 Lamego et al.
9,658,825 B2 5/2017 Garudadri et al.
9,662,052 B2 5/2017 Al-Ali et al.
9,668,679 B2 6/2017 Schurman et al.
9,668,680 B2 6/2017 Bruinsma et al.
9,668,703 B2 6/2017 Al-Ali
9,675,286 B2 6/2017 Diab
9,687,160 B2 6/2017 Kiani
9,693,719 B2 7/2017 Al-Ali et al.
9,693,737 B2 7/2017 Al-Ali
9,697,928 B2 7/2017 Al-Ali et al.
9,699,546 B2 7/2017 Qian et al.
9,717,425 B2 8/2017 Kiani et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,730,640 B2 8/2017 Diab et al.
9,736,569 B2 8/2017 Kelly et al.
9,743,887 B2 8/2017 Al-Ali et al.
9,749,232 B2 8/2017 Sampath et al.
9,750,442 B2 9/2017 Olsen
9,750,443 B2 9/2017 Smith et al.
9,750,461 B1 9/2017 Telfort
9,774,963 B1 9/2017 Han
9,775,520 B2 10/2017 Tran
9,775,545 B2 10/2017 Al-Ali et al.
9,775,546 B2 10/2017 Diab et al.
9,775,570 B2 10/2017 Al-Ali
9,778,079 B1 10/2017 Al-Ali et al.
9,782,077 B2 10/2017 Lamego et al.
9,782,110 B2 10/2017 Kiani
9,787,568 B2 10/2017 Lamego et al.
9,788,735 B2 10/2017 Al-Ali
9,788,768 B2 10/2017 Al-Ali et al.
9,795,300 B2 10/2017 Al-Ali
9,795,310 B2 10/2017 Al-Ali
9,795,358 B2 10/2017 Telfort et al.
9,795,739 B2 10/2017 Al-Ali et al.
9,801,556 B2 10/2017 Kiani
9,801,588 B2 10/2017 Weber et al.
9,808,188 B1 11/2017 Perea et al.
9,808,199 B2 11/2017 Kilsgaard et al.
9,814,418 B2 11/2017 Weber et al.
9,820,691 B2 11/2017 Kiani
9,833,152 B2 12/2017 Kiani et al.
9,833,180 B2 12/2017 Shakespeare et al.
9,839,379 B2 12/2017 Al-Ali et al.
9,839,381 B1 12/2017 Weber et al.
9,847,002 B2 12/2017 Kiani et al.
9,847,749 B2 12/2017 Kiani et al.
9,848,800 B1 12/2017 Lee et al.
9,848,806 B2 12/2017 Al-Ali
9,848,807 B2 12/2017 Lamego
D808,934 S 1/2018 Tang et al.
9,861,298 B2 1/2018 Eckerbom et al.
9,861,304 B2 1/2018 Al-Ali et al.
9,861,305 B1 1/2018 Weber et al.
9,867,578 B2 1/2018 Al-Ali et al.
9,872,623 B2 1/2018 Al-Ali
9,876,320 B2 1/2018 Coverston et al.
9,877,650 B2 1/2018 Muhsin et al.
9,877,686 B2 1/2018 Al-Ali et al.
9,891,079 B2 2/2018 Dalvi
9,895,107 B2 2/2018 Al-Ali et al.
9,900,687 B2 2/2018 Sorensen
9,913,617 B2 3/2018 Al-Ali et al.
9,924,893 B2 3/2018 Schurman et al.
9,924,897 B1 3/2018 Abdul-Hafiz
9,936,312 B2 4/2018 Meskens et al.
9,936,917 B2 4/2018 Poeze et al.
9,937,355 B2 4/2018 Kaib et al.
9,943,269 B2 4/2018 Muhsin et al.

(56) References Cited

U.S. PATENT DOCUMENTS 9,949,676 B2 4/2018 Al-Ali
D817,309 S 5/2018 Czaniecki et al.
9,955,919 B2 5/2018 LeBoeuf et al.
9,955,937 B2 5/2018 Telfort
9,965,946 B2 5/2018 Al-Ali et al.
9,980,667 B2 5/2018 Kiani et al.
D820,865 S 6/2018 Muhsin et al.
9,986,919 B2 6/2018 Lamego et al.
9,986,952 B2 6/2018 Dalvi et al.
9,989,560 B2 6/2018 Poeze et al.
9,993,207 B2 6/2018 Al-Ali et al.
10,007,758 B2 6/2018 Al-Ali et al.
D822,215 S 7/2018 Al-Ali et al.
D822,216 S 7/2018 Barker et al.
10,010,276 B2 7/2018 Al-Ali et al.
10,032,002 B2 7/2018 Kiani et al.
D826,211 S 8/2018 Kim
10,039,482 B2 8/2018 Al-Ali et al.
10,052,037 B2 8/2018 Kinast et al.
10,058,275 B2 8/2018 Al-Ali et al.
10,064,562 B2 9/2018 Al-Ali
10,086,138 B1 10/2018 Novak, Jr.
10,092,200 B2 10/2018 Al-Ali et al.
10,092,249 B2 10/2018 Kiani et al.
10,098,550 B2 10/2018 Al-Ali et al.
10,098,591 B2 10/2018 Al-Ali et al.
10,098,610 B2 10/2018 Al-Ali et al.
10,111,591 B2 10/2018 Dyell et al.
D833,624 S 11/2018 DeJong et al.
10,123,726 B2 11/2018 Al-Ali et al.
10,123,729 B2 11/2018 Dyell et al.
10,130,289 B2 11/2018 Al-Ali et al.
10,130,291 B2 11/2018 Schurman et al.
D835,282 S 12/2018 Barker et al.
D835,283 S 12/2018 Barker et al.
D835,284 S 12/2018 Barker et al.
D835,285 S 12/2018 Barker et al.
10,149,037 B1 12/2018 Chen
10,149,616 B2 12/2018 Al-Ali et al.
10,154,815 B2 12/2018 Al-Ali et al.
10,159,412 B2 12/2018 Lamego et al.
10,188,296 B2 1/2019 Al-Ali et al.
10,188,331 B1 1/2019 Kiani et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,194,847 B2 2/2019 Al-Ali
10,194,848 B1 2/2019 Kiani et al.
10,201,298 B2 2/2019 Al-Ali et al.
10,205,272 B2 2/2019 Kiani et al.
10,205,291 B2 2/2019 Scruggs et al.
10,213,108 B2 2/2019 Al-Ali
10,226,187 B2 3/2019 Al-Ali et al.
10,231,657 B2 3/2019 Al-Ali et al.
10,231,670 B2 3/2019 Blank et al.
RE47,353 E 4/2019 Kiani et al.
10,279,247 B2 5/2019 Kiani
10,292,657 B2 5/2019 Abdul-Hafiz et al.
10,292,664 B2 5/2019 Ai-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,362,384 B2 7/2019 Yun
10,383,520 B2 8/2019 Wojtczuk et al.
10,383,527 B2 8/2019 Al-Ali
10,388,120 B2 8/2019 Muhsin et al.
D864,120 S 10/2019 Forrest et al.
10,433,045 B2 10/2019 Trainer et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,463,340 B2 11/2019 Telfort et al.
10,471,159 B1 11/2019 Lapotko et al.
D868,752 S 12/2019 Zhu
D870,708 S 12/2019 Lindenberger
D871,376 S 12/2019 Zhou
10,499,183 B2 12/2019 Zellner
10,505,311 B2 12/2019 Al-Ali et al.
10,511,901 B2 12/2019 Garrett
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
RE47,882 E 3/2020 Al-Ali
D879,074 S 3/2020 Komiya et al.
10,602,255 B2 3/2020 Sandanger
10,608,817 B2 3/2020 Haider et al.
D880,477 S 4/2020 Forrest et al.
10,617,302 B2 4/2020 Al-Ali et al.
10,617,335 B2 4/2020 Al-Ali et al.
10,637,181 B2 4/2020 Al-Ali et al.
D883,257 S 5/2020 Duddy
D885,372 S 5/2020 Wang
10,639,468 B2 5/2020 Cook et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
10,681,445 B2 6/2020 Hatfield et al.
D889,441 S 7/2020 Lin
D890,708 S 7/2020 Forrest et al.
D890,727 S 7/2020 Park et al.
10,721,785 B2 7/2020 Al-Ali
10,728,645 B2 7/2020 Briggs et al.
D894,158 S 8/2020 Gu
10,736,518 B2 8/2020 Al-Ali et al.
10,750,984 B2 8/2020 Pauley et al.
D895,578 S 9/2020 Yang
D896,205 S 9/2020 Zhang et al.
D897,098 S 9/2020 Al-Ali
D897,319 S 9/2020 Wang
10,779,098 B2 9/2020 Iswanto et al.
10,791,390 B2 9/2020 Karayiannis et al.
D902,184 S 11/2020 Yang
10,827,249 B1 11/2020 Pine et al.
10,827,961 B1 11/2020 Iyengar et al.
10,828,007 B1 11/2020 Telfort et al.
10,832,818 B2 11/2020 Muhsin et al.
10,834,492 B2 11/2020 Feng et al.
D904,349 S 12/2020 Saxton et al.
D906,298 S 12/2020 Wang
10,849,554 B2 12/2020 Shreim et al.
10,856,750 B2 12/2020 Indorf et al.
10,869,115 B2 12/2020 Cohen et al.
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
10,959,639 B2 3/2021 Kidmose et al.
D916,135 S 4/2021 Indorf et al.
D917,046 S 4/2021 Abdul-Hafiz et al.
D917,425 S 4/2021 Wang
D917,550 S 4/2021 Indorf et al.
D917,564 S 4/2021 Indorf et al.
D917,704 S 4/2021 Al-Ali et al.
10,984,776 B2 4/2021 Yamkovoy
10,987,005 B2 4/2021 LeBoeuf et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
D920,288 S 5/2021 Vautour
11,006,867 B2 5/2021 Al-Ali
D921,202 S 6/2021 Al-Ali et al.
D922,985 S 6/2021 Kataoa

(56) References Cited

U.S. PATENT DOCUMENTS

D923,610 S 6/2021 Bonahoom et al.
11,024,064 B2 6/2021 Muhsin et al.
11,026,023 B2 6/2021 Wang et al.
11,026,604 B2 6/2021 Chen et al.
D924,848 S 7/2021 Yang
D925,597 S 7/2021 Chandran et al.
D927,699 S 8/2021 Al-Ali et al.
D928,122 S 8/2021 Yoshida et al.
D928,742 S 8/2021 Liu
11,076,777 B2 8/2021 Lee et al.
11,095,973 B1 8/2021 Zalisk et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
D939,479 S 12/2021 Wang et al.
11,191,484 B2 12/2021 Kiani et al.
D941,278 S 1/2022 Laffon de Mazieres et al.
11,252,494 B2 2/2022 Mori
D945,404 S 3/2022 Birger
D945,405 S 3/2022 Rose et al.
D946,596 S 3/2022 Ahmed
D946,597 S 3/2022 Ahmed
D946,598 S 3/2022 Ahmed
D946,617 S 3/2022 Ahmed
11,266,531 B2 3/2022 Aceti et al.
11,272,839 B2 3/2022 Al-Ali et al.
11,289,199 B2 3/2022 Al-Ali
RE49,034 E 4/2022 Al-Ali
11,298,021 B2 4/2022 Muhsin et al.
11,317,185 B2 4/2022 Imamura
D950,580 S 5/2022 Ahmed
D950,599 S 5/2022 Ahmed
D950,738 S 5/2022 Al-Ali et al.
D957,648 S 7/2022 Al-Ali
11,389,093 B2 7/2022 Triman et al.
D959,411 S 8/2022 Ando et al.
11,406,286 B2 8/2022 Al-Ali et al.
11,417,426 B2 8/2022 Muhsin et al.
11,425,484 B2 8/2022 Kim et al.
11,426,125 B2 8/2022 Abdul-Hafiz et al.
11,432,771 B2 9/2022 Abdul-Hafiz et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
D999,244 S 9/2023 Indorf et al.
D999,245 S 9/2023 Indorf et al.
D999,246 S 9/2023 Indorf et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,877,867 B2 1/2024 Abdul-Hafiz et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
12,336,796 B2 6/2025 Al-Ali
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2003/0220584 A1 11/2003 Honeyager et al.
2004/0106163 A1 6/2004 Workman, Jr. et al.
2005/0033131 A1 2/2005 Chen et al.
2005/0055276 A1 3/2005 Kiani et al.
2005/0124375 A1 6/2005 Nowosielski
2005/0209516 A1 9/2005 Fraden
2005/0234317 A1 10/2005 Kiani
2006/0045304 A1 3/2006 Lee et al.
2006/0073719 A1 4/2006 Kiani
2006/0161054 A1 7/2006 Reuss et al.
2006/0189871 A1 8/2006 Al-Ali et al.
2007/0032715 A1 2/2007 Eghbal et al.
2007/0032731 A1 2/2007 Lovejoy et al.
2007/0073116 A1 3/2007 Kiani et al.
2007/0078315 A1 4/2007 Kling et al.
2007/0180140 A1 8/2007 Welch et al.
2007/0197881 A1 8/2007 Wolf et al.
2007/0244377 A1 10/2007 Cozad et al.

(56) References Cited

U.S. PATENT DOCUMENTS

2007/0282478 A1 12/2007 Al-Ali et al.
2008/0064965 A1 3/2008 Jay et al.
2008/0076972 A1 3/2008 Dorogusker et al.
2008/0094228 A1 4/2008 Welch et al.
2008/0154098 A1 6/2008 Morris et al.
2008/0177162 A1 7/2008 Bae et al.
2008/0205679 A1 8/2008 Darbut et al.
2008/0221418 A1 9/2008 Al-Ali et al.
2009/0010461 A1 1/2009 Klinghult
2009/0024004 A1 1/2009 Yang
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275813 A1 11/2009 Davis
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0160714 A1 6/2010 Chua et al.
2010/0197360 A1 8/2010 Namgoong et al.
2010/0234718 A1 9/2010 Sampath et al.
2010/0270257 A1 10/2010 Wachman et al.
2010/0274109 A1 10/2010 Hu et al.
2010/0308999 A1 12/2010 Chornenky
2010/0331631 A1 12/2010 MacLaughlin
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0118561 A1 5/2011 Tari et al.
2011/0125060 A1 5/2011 Telfort et al.
2011/0137141 A1 6/2011 Razoumov et al.
2011/0137297 A1 6/2011 Kiani et al.
2011/0144779 A1 6/2011 Janse et al.
2011/0166624 A1 7/2011 Dietrich et al.
2011/0172498 A1 7/2011 Olsen et al.
2011/0208015 A1 8/2011 Welch et al.
2011/0230733 A1 9/2011 Al-Ali
2012/0123231 A1 5/2012 O'Reilly
2012/0165629 A1 6/2012 Merritt et al.
2012/0209082 A1 8/2012 Al-Ali
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0041591 A1 2/2013 Lamego
2013/0060147 A1 3/2013 Welch et al.
2013/0096405 A1 4/2013 Garfio
2013/0096936 A1 4/2013 Sampath et al.
2013/0243021 A1 9/2013 Siskavich
2013/0253334 A1 9/2013 Al-Ali et al.
2013/0296672 A1 11/2013 O'Neil et al.
2013/0296713 A1 11/2013 Al-Ali et al.
2013/0324808 A1 12/2013 Al-Ali et al.
2013/0331660 A1 12/2013 Al-Ali et al.
2013/0345921 A1 12/2013 Al-Ali et al.
2014/0012100 A1 1/2014 Al-Ali et al.
2014/0051953 A1 2/2014 Lamego et al.
2014/0120564 A1 5/2014 Workman et al.
2014/0121482 A1 5/2014 Merritt et al.
2014/0127137 A1 5/2014 Bellott et al.
2014/0163344 A1 6/2014 Al-Ali
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0180160 A1 6/2014 Brown et al.
2014/0187885 A1 7/2014 Kreuzer
2014/0187973 A1 7/2014 Brown et al.
2014/0213864 A1 7/2014 Abdul-Hafiz et al.
2014/0275835 A1 9/2014 Lamego et al.
2014/0275871 A1 9/2014 Lamego et al.
2014/0275872 A1 9/2014 Merritt et al.
2014/0288400 A1 9/2014 Diab et al.
2014/0316217 A1 10/2014 Purdon et al.
2014/0316218 A1 10/2014 Purdon et al.
2014/0316228 A1 10/2014 Blank et al.
2014/0323825 A1 10/2014 Al-Ali et al.
2014/0323897 A1 10/2014 Brown et al.
2014/0323898 A1 10/2014 Purdon et al.
2014/0330092 A1 11/2014 Al-Ali et al.
2014/0330098 A1 11/2014 Merritt et al.
2014/0357966 A1 12/2014 Al-Ali et al.
2015/0005600 A1 1/2015 Blank et al.
2015/0011907 A1 1/2015 Purdon et al.
2015/0032029 A1 1/2015 Al-Ali et al.
2015/0038859 A1 2/2015 Dalvi et al.
2015/0073241 A1 3/2015 Lamego
2015/0080754 A1 3/2015 Purdon et al.
2015/0087936 A1 3/2015 Al-Ali et al.
2015/0094546 A1 4/2015 Al-Ali
2015/0099950 A1 4/2015 Al-Ali et al.
2015/0101844 A1 4/2015 Al-Ali et al.
2015/0106121 A1 4/2015 Muhsin et al.
2015/0112151 A1 4/2015 Muhsin et al.
2015/0165312 A1 6/2015 Kiani
2015/0196249 A1 7/2015 Brown et al.
2015/0216459 A1 8/2015 Al-Ali et al.
2015/0238722 A1 8/2015 Al-Ali
2015/0245773 A1 9/2015 Lamego et al.
2015/0245794 A1 9/2015 Al-Ali
2015/0257689 A1 9/2015 Al-Ali et al.
2015/0272514 A1 10/2015 Kiani et al.
2015/0351697 A1 12/2015 Weber et al.
2015/0359429 A1 12/2015 Al-Ali et al.
2015/0366507 A1 12/2015 Blank et al.
2016/0029932 A1 2/2016 Al-Ali
2016/0058347 A1 3/2016 Reichgott et al.
2016/0066080 A1 3/2016 Kolton
2016/0066824 A1 3/2016 Al-Ali et al.
2016/0081552 A1 3/2016 Wojtczuk et al.
2016/0095543 A1 4/2016 Telfort et al.
2016/0095548 A1 4/2016 Al-Ali et al.
2016/0103598 A1 4/2016 Al-Ali et al.
2016/0166182 A1 6/2016 Al-Ali et al.
2016/0166183 A1 6/2016 Poeze et al.
2016/0173969 A1 6/2016 DeKalb
2016/0196388 A1 7/2016 Lamego
2016/0197436 A1 7/2016 Barker et al.
2016/0213281 A1 7/2016 Eckerbom et al.
2016/0228043 A1 8/2016 O'Neil et al.
2016/0233632 A1 8/2016 Scruggs et al.
2016/0234944 A1 8/2016 Schmidt et al.
2016/0270735 A1 9/2016 Diab et al.
2016/0283665 A1 9/2016 Sampath et al.
2016/0287090 A1 10/2016 Al-Ali et al.
2016/0287786 A1 10/2016 Kiani
2016/0296169 A1 10/2016 McHale et al.
2016/0310052 A1 10/2016 Al-Ali et al.
2016/0314260 A1 10/2016 Kiani
2016/0324488 A1 11/2016 Olsen
2016/0327984 A1 11/2016 Al-Ali et al.
2016/0331332 A1 11/2016 Al-Ali
2016/0367173 A1 12/2016 Dalvi et al.
2017/0000394 A1 1/2017 Al-Ali et al.
2017/0007134 A1 1/2017 Al-Ali et al.
2017/0007198 A1 1/2017 Al-Ali et al.
2017/0014083 A1 1/2017 Diab et al.
2017/0014084 A1 1/2017 Al-Ali et al.
2017/0024748 A1 1/2017 Haider
2017/0042488 A1 2/2017 Muhsin
2017/0055851 A1 3/2017 Al-Ali
2017/0055882 A1 3/2017 Al-Ali et al.
2017/0055887 A1 3/2017 Al-Ali
2017/0055896 A1 3/2017 Al-Ali
2017/0079594 A1 3/2017 Telfort et al.
2017/0086723 A1 3/2017 Al-Ali et al.
2017/0143281 A1 5/2017 Olsen
2017/0147774 A1 5/2017 Kiani
2017/0156620 A1 6/2017 Al-Ali et al.
2017/0173632 A1 6/2017 Al-Ali
2017/0187146 A1 6/2017 Kiani et al.

(56) References Cited

U.S. PATENT DOCUMENTS

2017/0188919 A1 7/2017 Al-Ali et al.
2017/0196464 A1 7/2017 Jansen et al.
2017/0196470 A1 7/2017 Lamego et al.
2017/0224262 A1 8/2017 Al-Ali
2017/0228516 A1 8/2017 Sampath et al.
2017/0245790 A1 8/2017 Al-Ali et al.
2017/0251974 A1 9/2017 Shreim et al.
2017/0251975 A1 9/2017 Shreim et al.
2017/0258403 A1 9/2017 Abdul-Hafiz et al.
2017/0311851 A1 11/2017 Schurman et al.
2017/0311891 A1 11/2017 Kiani et al.
2017/0325728 A1 11/2017 Al-Ali et al.
2017/0332976 A1 11/2017 Al-Ali
2017/0340293 A1 11/2017 Al-Ali et al.
2017/0360310 A1 12/2017 Kiani
2017/0367632 A1 12/2017 Al-Ali et al.
2018/0008146 A1 1/2018 Al-Ali et al.
2018/0013562 A1 1/2018 Haider et al.
2018/0014752 A1 1/2018 Al-Ali et al.
2018/0028124 A1 2/2018 Al-Ali et al.
2018/0055385 A1 3/2018 Al-Ali
2018/0055390 A1 3/2018 Kiani et al.
2018/0055430 A1 3/2018 Diab et al.
2018/0064381 A1 3/2018 Shakespeare et al.
2018/0069776 A1 3/2018 Lamego et al.
2018/0070867 A1 3/2018 Smith et al.
2018/0082767 A1 3/2018 Al-Ali et al.
2018/0085068 A1 3/2018 Telfort
2018/0087937 A1 3/2018 Al-Ali et al.
2018/0103874 A1 4/2018 Lee et al.
2018/0103905 A1 4/2018 Kiani
2018/0110478 A1 4/2018 Al-Ali
2018/0116575 A1 5/2018 Perea et al.
2018/0125368 A1 5/2018 Lamego et al.
2018/0125430 A1 5/2018 Al-Ali et al.
2018/0125445 A1 5/2018 Telfort et al.
2018/0130325 A1 5/2018 Kiani et al.
2018/0132769 A1 5/2018 Weber et al.
2018/0132770 A1 5/2018 Lamego
2018/0146901 A1 5/2018 Al-Ali et al.
2018/0146902 A1 5/2018 Kiani et al.
2018/0153442 A1 6/2018 Eckerbom et al.
2018/0153446 A1 6/2018 Kiani
2018/0153447 A1 6/2018 Al-Ali et al.
2018/0153448 A1 6/2018 Weber et al.
2018/0161499 A1 6/2018 Al-Ali et al.
2018/0168491 A1 6/2018 Al-Ali et al.
2018/0174679 A1 6/2018 Sampath et al.
2018/0174680 A1 6/2018 Sampath et al.
2018/0182484 A1 6/2018 Sampath et al.
2018/0184917 A1 7/2018 Kiani
2018/0192924 A1 7/2018 Al-Ali
2018/0192953 A1 7/2018 Shreim et al.
2018/0192955 A1 7/2018 Al-Ali et al.
2018/0199871 A1 7/2018 Pauley et al.
2018/0206795 A1 7/2018 Al-Ali
2018/0206815 A1 7/2018 Telfort
2018/0213583 A1 7/2018 Al-Ali
2018/0214031 A1 8/2018 Kiani et al.
2018/0214090 A1 8/2018 Al-Ali et al.
2018/0218792 A1 8/2018 Muhsin et al.
2018/0225960 A1 8/2018 Al-Ali et al.
2018/0238718 A1 8/2018 Dalvi
2018/0242853 A1 8/2018 Al-Ali
2018/0242921 A1 8/2018 Muhsin et al.
2018/0242923 A1 8/2018 Al-Ali et al.
2018/0242924 A1 8/2018 Barker et al.
2018/0242926 A1 8/2018 Muhsin et al.
2018/0247353 A1 8/2018 Al-Ali et al.
2018/0247712 A1 8/2018 Muhsin et al.
2018/0249933 A1 9/2018 Schurman et al.
2018/0253947 A1 9/2018 Muhsin et al.
2018/0256087 A1 9/2018 Al-Ali et al.
2018/0256113 A1 9/2018 Weber et al.
2018/0285094 A1 10/2018 Housel et al.
2018/0289325 A1 10/2018 Poeze et al.
2018/0289337 A1 10/2018 Al-Ali et al.
2018/0296161 A1 10/2018 Shreim et al.
2018/0300919 A1 10/2018 Muhsin et al.
2018/0310822 A1 11/2018 Indorf et al.
2018/0310823 A1 11/2018 Al-Ali et al.
2018/0317826 A1 11/2018 Muhsin et al.
2018/0317841 A1 11/2018 Novak, Jr.
2018/0332379 A1 11/2018 McGarry et al.
2018/0333055 A1 11/2018 Lamego et al.
2018/0333087 A1 11/2018 Al-Ali
2018/0352338 A1 12/2018 Murarka et al.
2019/0000317 A1 1/2019 Muhsin et al.
2019/0000362 A1 1/2019 Kiani et al.
2019/0015023 A1 1/2019 Monfre
2019/0021638 A1 1/2019 Al-Ali et al.
2019/0029574 A1 1/2019 Schurman et al.
2019/0029578 A1 1/2019 Al-Ali et al.
2019/0029593 A1 1/2019 Orron et al.
2019/0038143 A1 2/2019 Al-Ali
2019/0058280 A1 2/2019 Al-Ali et al.
2019/0058281 A1 2/2019 Al-Ali et al.
2019/0117070 A1 4/2019 Muhsin et al.
2019/0231270 A1 8/2019 Abdul-Hafiz et al.
2019/0239787 A1 8/2019 Pauley et al.
2019/0239796 A1 8/2019 Avrahamson
2019/0320906 A1 10/2019 Olsen
2019/0374139 A1 12/2019 Kiani et al.
2019/0374713 A1 12/2019 Kiani et al.
2020/0060869 A1 2/2020 Telfort et al.
2020/0111552 A1 4/2020 Ahmed
2020/0113435 A1 4/2020 Muhsin
2020/0113488 A1 4/2020 Al-Ali et al.
2020/0113496 A1 4/2020 Scruggs et al.
2020/0113497 A1 4/2020 Triman et al.
2020/0113520 A1 4/2020 Abdul-Hafiz et al.
2020/0138288 A1 5/2020 Al-Ali et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0236729 A1 8/2021 Kiani et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0321946 A1 10/2021 Abdul-Hafiz et al.
2021/0330228 A1 10/2021 Olsen et al.
2021/0386382 A1 12/2021 Olsen et al.
2021/0390941 A1 12/2021 Lakshminarayanan et al.
2021/0402110 A1 12/2021 Pauley et al.
2022/0007097 A1 1/2022 Ko et al.
2022/0026355 A1 1/2022 Normand et al.
2022/0039707 A1 2/2022 Sharma et al.
2022/0053892 A1 2/2022 Al-Ali et al.
2022/0060807 A1 2/2022 Wei
2022/0071562 A1 3/2022 Kiani
2022/0095040 A1 3/2022 Holley et al.

(56) References Cited

U.S. PATENT DOCUMENTS

2022/0096603 A1 3/2022 Kiani et al.
2022/0151521 A1 5/2022 Krishnamani et al.
2022/0218244 A1 7/2022 Kiani et al.
2022/0248120 A1 8/2022 Ito et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo
2023/0058052 A1 2/2023 Al-Ali
2023/0058342 A1 2/2023 Kiani
2023/0069789 A1 3/2023 Koo et al.
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0116371 A1 4/2023 Mills et al.
2023/0145155 A1 5/2023 Krishnamani et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0252046 A1 8/2024 Jansen et al.
2024/0260894 A1 8/2024 Olsen
2024/0267698 A1 8/2024 Telfort et al.
2024/0277233 A1 8/2024 Al-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen

FOREIGN PATENT DOCUMENTS

CN 201105090 8/2008
CN 201230878 5/2009
CN 201280178 7/2009
CN 101530647 9/2009
CN 101708121 5/2010
DE 35 05 099 9/1985
DE 37 23 809 1/1989
DE 20 2004 018 615 4/2006
EM D006885901-0001 9/2019
EM D006636254-0001 10/2019
EM D006772273-0002 10/2019
EM D007538657-0002 2/2020
EM D006523809-0001 3/2020
EM D007725007-0001 3/2020
EM D007735212-0001 3/2020
EM D007719497-0002 4/2020
EM D007223698-0001 5/2020
EM D007984109-0001 6/2020
EM D007797287-0009 7/2020
EM D007797287-0010 7/2020
EM D008053755-0002 7/2020
EM D008053755-0003 7/2020
EM D008086896-0001 8/2020
EM D008086896-0002 8/2020
EM D008099535-0001 9/2020
EM D008166235-0002 9/2020
EM D007290614-0006 10/2020
EM D008129456-0001 10/2020
EM D008172480-0002 10/2020
EM D008025118-0007 11/2020
EM D008025118-0008 11/2020
EM D008025118-0009 11/2020
EM D008025118-0010 11/2020
EM D008277826-0001 12/2020
EM D008150452-0002 1/2021
EM D008368757-0001 1/2021
EM D008499883-0001 4/2021
EM D008534457-0001 5/2021
EM D008559868-0001 6/2021
EM D008599195-0002 7/2021
EM D008324495-0002 9/2021
EM D008656482-0011 2/2022
EM D008860423-0005 4/2022
EM D008860423-0006 4/2022
EM D009074032-0001 7/2022
EM D009074032-0002 7/2022
EM D009079510-0001 7/2022
EM D009101983-0002 8/2022
EP 2 116 183 11/2009
EP 2 214 554 1/2012
GB 09166 7/1914
JP 61-279222 12/1986
JP 63-102767 5/1988
JP 63-292799 11/1988
JP 04-242400 8/1992
JP 3013262 7/1995
JP 08-195999 7/1996
JP 09-253062 9/1997
JP 10-239158 9/1998
JP 2837641 12/1998
JP 2905116 6/1999
JP 2002-000576 1/2002
JP 2007-021106 2/2007
JP 2007-215722 8/2007
JP 2008-136556 6/2008
JP 2008-219586 9/2008
JP 2009-082263 4/2009
JP 4952244 6/2012
KR 10-2005-0099444 10/2005
KR 10-2006-0002448 1/2006
KR 10-2006-0007334 1/2006
KR 10-0561091 3/2006
KR 10-0677583 2/2007
KR 10-2008-0088217 10/2008
KR 10-0958106 5/2010
KR 10-1020508 3/2011
KR 10-1030887 4/2011
KR 10-2011-0052783 5/2011
KR 10-1044883 6/2011
KR 10-1225554 1/2013
TW M344138 11/2008
TW M348587 1/2009
TW M360013 7/2009
WO WO 95/015067 6/1995
WO WO 99/062403 12/1999
WO WO 2007/050487 5/2007
WO WO 2007/100959 9/2007
WO WO 2009/001449 12/2008
WO WO 2009/033181 3/2009
WO WO 2010/079257 7/2010
WO WO 2010/108287 9/2010
WO WO 2011/102846 8/2011
WO WO 2021/263098 12/2021

OTHER PUBLICATIONS

US 2024/0016391 A1, 01/2024, Lapotko et al. (withdrawn)
International Search Report and Written Opinion as received in PCT Application No. PCT/US2010/033796 as mailed Oct. 17, 2011, pp. 13.

1800
1840
1860
1850

1800
1840
1860
1830
1850
1830
1810

1800
1840
1860
1810
1850
1830
1820

1800
1860
1830
1810
1822
1850
1820

1800
1840
1830
1810

2200
2210
2250
2230

2210
2212
2214
SENSOR
2216
RED
IR
2254
2250
2256
2252
WHITE (DETECTOR ANODE)
GREEN (DETECTOR CATHODE)
OUTER SHIELD
INNER SHIELD
ORANGE (IR ANODE)
RED (RED ANODE)
MC8 CONNECTOR PINOUT
2230
2 1 4 3 5 6 8 7
2232
2236
EEPROM GND
EEPROM I/O 2300
2330
2350
2310

SENSOR
RED
IR
2312
2314
2316
2352
2354
M15 CONNECTOR
RED (RED ANODE)
ORANGE (IR ANODE)
GREEN (DET CATHODE)
WHITE (DET ANODE)
INNER SHIELD
OUTER SHIELD
R1
R2
2 & 9
3 & 10
8
15
6
7
14
5
13
1
2332
2334
2336
2356

2700
2740
2760
2750

2700
2750
2740
2760
2722

2700
2760
2730
2710
2750
2720

2700
2740
2760
2750
2730
2710
2720

2700
2740
2730
2710

2700
2760
2740
2730
2750
2710

PHYSIOLOGICAL MEASUREMENT DEVICE

CROSS-REFERENCE TO RELATED APPLICATIONS

The present application is a continuation of U.S. patent application Ser. No. 17/381,086, filed Jul. 20, 2021, titled "PHYSIOLOGICAL MEASUREMENT DEVICE," which is a continuation of U.S. patent application Ser. No. 17/360,570, filed Jun. 28, 2021, titled "PHYSIOLOGICAL MEASUREMENT DEVICE," which is a continuation of U.S. patent application Ser. No. 16/377,772, filed Apr. 8, 2019, titled "PHYSIOLOGICAL MEASUREMENT DEVICE," which is a continuation of U.S. patent application Ser. No. 15/417,640, filed Jan. 27, 2017, titled "Ear Sensor," which is a continuation of U.S. patent application Ser. No. 14/218,328, filed Mar. 18, 2014, titled "Ear Sensor," which is a continuation of U.S. patent application Ser. No. 13/975,008, filed Aug. 23, 2013, titled "Ear Sensor," which is a continuation of U.S. patent application Ser. No. 12/658,872, filed Feb. 16, 2010, titled "Ear Sensor," which claims priority benefit under 35 U.S.C. § 119(e) to U.S. Provisional Patent Application No. 61/152,964, filed Feb. 16, 2009, titled "Ear Sensor," each of which is hereby incorporated by reference herein in its entirety.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are typically attached to a finger, and the patient cable transmits drive signals to these emitters from the monitor. The emitters respond to the drive signals to transmit light into the fleshy fingertip tissue. The detector generates a signal responsive to the emitted light after attenuation by pulsatile blood flow within the fingertip. The patient cable transmits the detector signal to the monitor, which processes the signal to provide a numerical readout of physiological parameters such as oxygen saturation ($SpO_2$) and pulse rate.

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. Nos. 6,088,607 and 5,782,757; all of which are assigned to Masimo Corporation, Irvine, California ("Masimo") and are incorporated by reference herein. An ear sensor is disclosed in U.S. Pat. No. 7,341,559 titled Pulse Oximetry Ear Sensor, also assigned to Masimo and also incorporated by reference herein.

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), as a few examples. Advanced physiological monitors and corresponding multiple wavelength optical sensors capable of measuring parameters in addition to $SpO_2$, such as HbCO, HbMet and Hbt are described in at least U.S. patent application Ser. No. 12/056,179, filed Mar. 26, 2008, titled Multiple Wavelength Optical Sensor and U.S. patent application Ser. No. 11/366,208, filed Mar. 1, 2006, titled Noninvasive Multi-Parameter Patient Monitor, both incorporated by reference herein. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index (PI), signal quality (SiQ), pulse variability index (PVI), HbCO and HbMet among other parameters are also available from Masimo.

SUMMARY OF THE INVENTION

FIG. 1 illustrates various areas of the ear 100 that are amenable to blood parameter measurements, such as oxygen saturation ($SpO_2$). An ear site has the advantage of more quickly and more accurately reflecting oxygenation changes in the body's core as compared to peripheral site measurements, such as a fingertip. Conventional ear sensors utilize a sensor clip on the ear lobe 110. However, significant variations in lobe size, shape and thickness and the general floppiness of the ear lobe render this site less suitable for central oxygen saturation measurements than the concha 120 and the ear canal 130. Disclosed herein are various embodiments for obtaining noninvasive blood parameter measurements from concha 120 and ear canal 130 tissue sites.

One aspect of an ear sensor optically measures physiological parameters related to blood constituents by transmitting multiple wavelengths of light into a concha site and receiving the light after attenuation by pulsatile blood flow within the concha site. The ear sensor comprises a sensor body, a sensor connector and a sensor cable interconnecting the sensor body and the sensor connector. The sensor body comprises a base, legs and an optical assembly. The legs extend from the base to detector and emitter housings. An optical assembly has an emitter and a detector. The emitter is disposed in the emitter housing and the detector is disposed in the detector housing. The legs have an unflexed position with the emitter housing proximate the detector housing and a flexed position with the emitter housing distal the detector housing. The legs are moved to the flexed position so as to position the detector housing and emitter housing over opposite sides of a concha site. The legs are released to the unflexed position so that the concha site is grasped between the detector housing and emitter housing.

In various embodiments, the ear sensor has a resilient frame and a one piece molded skin disposed over the resilient frame. A cup is disposed proximate the detector housing and has a surface that generally conforms to the curvature of the concha site so as to couple the detector to the concha site and so as to block ambient light. A sensor cable has wires extending from one end of the sensor cable and disposed within channels defined by the resilient frame. The wires electrically and mechanically attach to the optical assembly. A connector is attached to the other end of the sensor cable, and the cable wires electrically and mechanically attach to the connector so as to provide communications between the connector and the optical assembly.

In other embodiments, a stabilizer maintains the position of the detector housing and the emitter housing on the concha site. The stabilizer may have a ring that encircles the legs. The ring has a hold position disposed against the legs and a release position spaced from the legs. A release, when pressed, moves the ring from the hold position to the release position, allowing the ring to slidably move along the legs in a direction away from the base so as to increase the force of the emitter housing and detector housing on the concha site in the hold position and in a direction toward the base so as to decrease the force of the emitter housing and the detector housing on the concha site in the hold position. The stabilizer may have an ear hanger that rests along the back of the ear and couples to at least one of the legs and the sensor cable.

Another aspect of an ear sensor comprises providing a sensor body having a base, legs extending from the base and an optical housing disposed at ends of the legs distal the base. An optical assembly is disposed in the housing. The sensor body is flexed so as to position the housing over a concha site. The sensor body is unflexed so as to attach the housing to the concha site and position the optical assembly to illuminate the concha site.

In various embodiments, an ear surface conforming member is molded to at least a portion of the housing so as to physically couple the housing to the concha site and block ambient light from the optical assembly accordingly. The force of the housing against the concha site is adjusted. The adjusting comprises positioning a force adjustment ring on the sensor body so as to encircle the legs. The positioning comprises squeezing a ring release so as to move ring grips away from the legs, moving the force adjustment ring along the legs and toward the housing so as to increase the force of the housing on the concha site, and moving the force adjustment ring along the legs and away from the housing so as to decrease the force of the housing on the concha site.

In other embodiments, an aspect of the ear sensor comprises supporting at least a portion of the weight of the sensor body and corresponding sensor cable so as to reduce the force needed to attach the housing to the concha site. The supporting comprises attaching at least one of the sensor body and sensor cable to an ear hook placed over the ear.

A further aspect of an ear sensor comprising a clip means having a flexed position and an unflexed position. An optical means transmits multiple wavelength light into a tissue site when activated and receives the light after attenuation by pulsatile blood flow within the tissue site. The optical means is disposed on the clip means so that the optical means can be positioned on a concha site in the flexed position and pinched against the concha site in the unflexed position. A connector means mechanically attaches to and electrically communicates with a monitor. A cable means interconnects the connector means with the optical means. In various embodiments, the clip means comprises a resilient frame means for securing the optical means in a fixed position relative to the tissue site. A housing means encloses the resilient frame means and the optical means. A cup means physically couples at least a portion of the optical means to the concha site and blocks ambient light from the optical means. An adjustable force means holds the clip means to the concha site. Alternatively, or in addition to, a support means holds the clip means to the concha site.

BRIEF DESCRIPTION OF THE DRAWINGS

FIGS. 2A-B are a side view and a perspective view of an ear bud embodiment of an ear sensor;

FIGS. 3A-B are perspective views of a flexible ear pad embodiment of an ear sensor;

FIGS. 4A-D are side views of "C"-clip embodiments for attaching an ear sensor to a concha site;

FIGS. 5A-B are perspective views of alligator clip embodiments for attaching an ear sensor to a concha site;

FIGS. 6A-B are perspective views of a clear adhesive disk embodiment for attaching an ear sensor to a concha site;

FIGS. 7A-C are perspective views of a flexible magnet disk embodiment for attaching an ear sensor to a concha site;

FIGS. 8A-B illustrate a concha-placed reflective sensor embodiment;

FIGS. 9A-B illustrate an "in-the-canal" reflective sensor embodiment;

FIGS. 10A-B illustrate "behind-the-ear" transmissive and/or reflective sensor embodiments;

FIGS. 11A-B illustrate an integrated ear lobe attachment and concha-placed sensor embodiment;

FIGS. 12A-F illustrate a "Y"-clip sensor embodiment for concha-placement;

FIGS. 13A-F are side views of ear-hook support embodiments;

FIGS. 14A-B are perspective views of headband support embodiments;

FIGS. 15A-B are front and perspective views of a "stethoscope" support embodiment;

FIG. 16 is a perspective view of a "headphone" support embodiment;

FIGS. 17A-B are perspective views of a concha-clip sensor;

FIGS. 18A-E are top, perspective, front, detector-side and emitter-side views, respectively, of a concha-clip sensor body;

FIG. 19 is an exploded view of an concha-clip sensor;

FIGS. 20A-B are assembly and detailed assembly views of a concha-clip sensor;

FIG. 21A-B are a mechanical representation and a corresponding electrical (schematic) representation of a concha-clip sensor having a DB9 connector;

FIG. 22A-B are a mechanical representation and a corresponding electrical (schematic) representation of a concha-clip sensor having a MC8 connector;

FIG. 23A-B are a mechanical representation and a corresponding electrical (schematic) representation of a concha-clip sensor having a M15 connector;

FIGS. 24A-C are assembly step representations for installing an optical assembly into a resilient frame and installing the resilient frame into a sensor housing;

FIGS. 25A-E are top, perspective, front, side cross-section; and side views, respectively, of a force adjustment ring;

FIGS. 26A-F are top, disassembled perspective, assembled perspective, front, detector-side and emitter-side views of a concha-clip sensor body and corresponding force adjustment ring; and FIGS. 27A-F are top, bottom, perspective, detector-side, front, emitter side and perspective views, respectively of an concha-clip sensor body having a parallel-routed sensor cable.

DETAILED DESCRIPTION OF THE PREFERRED EMBODIMENTS

Figure 1:
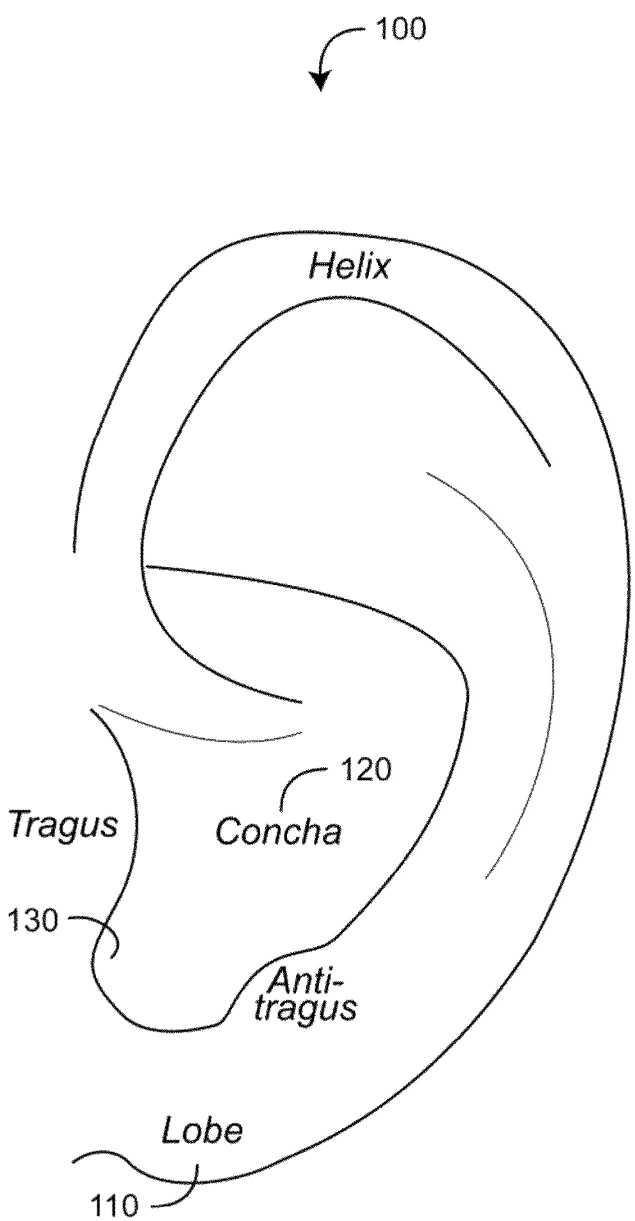
FIG. 1 is an illustration of the pinna or external ear structure, including the concha.
Figure 2A:
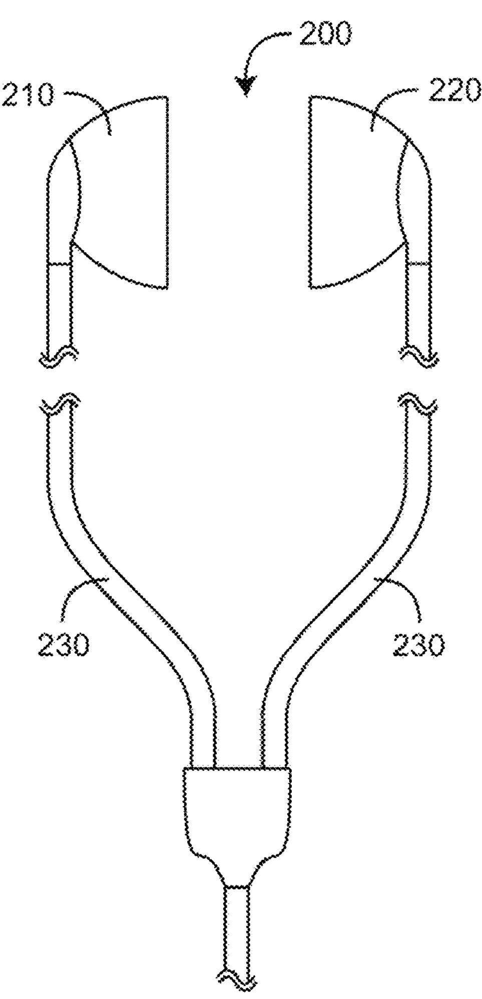
FIGS. 2A-B and 3A-B illustrate various ear sensor embodiments.
Figure 2B:
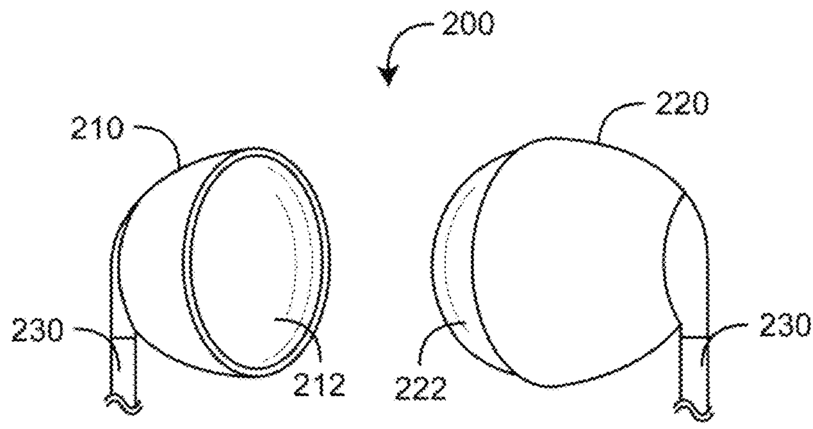

FIGS. 2A-B illustrate an ear bud embodiment of an ear sensor 200 having an emitter ear bud 210, a detector ear bud 220 and connecting cables 230. The emitter ear bud 210 has a generally concave surface for attachment to the back of an ear. The detector ear bud 220 has a generally convex surface 222 for attachment inside the ear at a concha site opposite the emitter ear bud 210. Sensor cables 230 are attached at the back of each ear bud having wires for electrical communications with a physiological monitor, such as a pulse oximeter. In particular, the emitter ear bud 210 includes wires for receiving emitter drive current from a monitor and the detector ear bud 220 includes wires for transmitting photodiode current to the monitor.

Figure 3A:
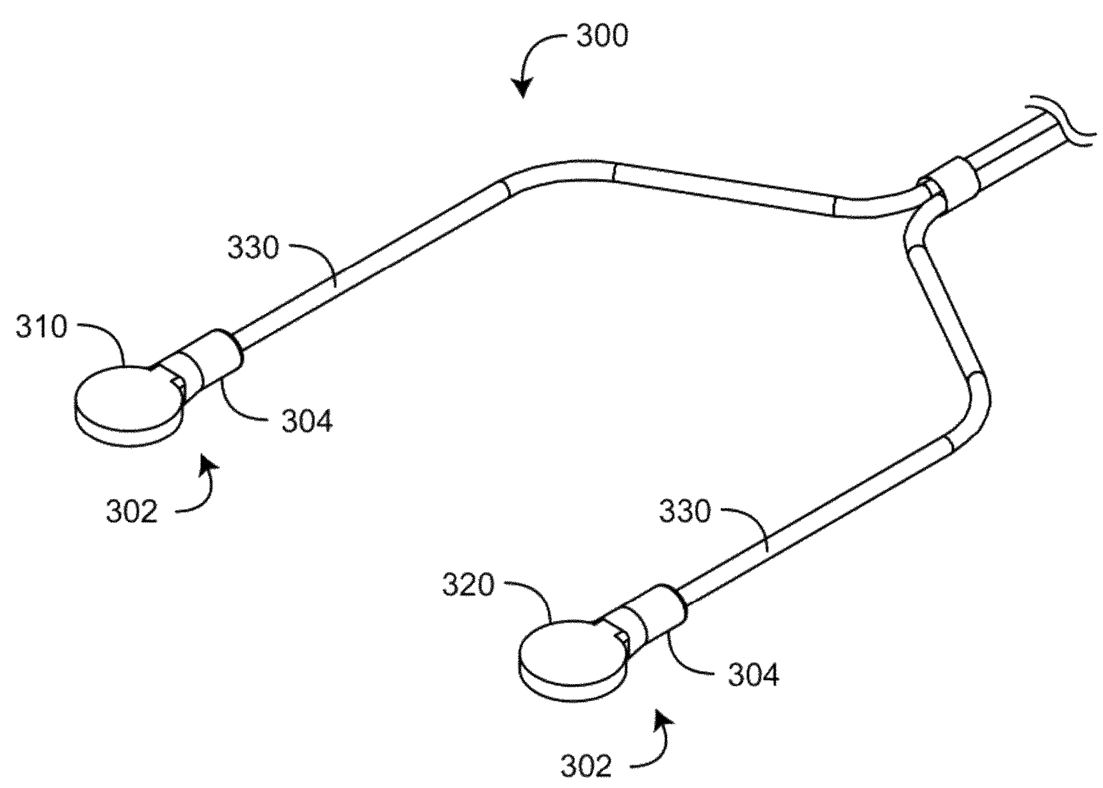
Figure 3B:
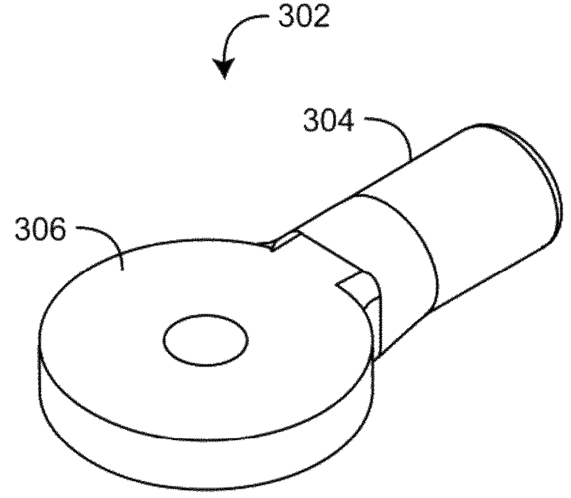

FIGS. 3A-B illustrate a flexible ear pad embodiment of an ear sensor 300 having an emitter pad 310, a detector pad 320 and corresponding cables 330. The sensor pads 310, 320 advantageously include a housing for each of the emitter pad 310 and the detector pad 320, minimizing the number of unique parts for the ear sensor. The detector pad 320 houses a shielded detector assembly (not shown). The emitter pad houses 310 an emitter (not shown). Both the detector pad 320 and the emitter pad 310 are connected to a sensor cable 330. The pads 310, 320 have an integrated bend relief 304 providing a finger grip. The pad face 306 provides a generally planar, pliant contact surface that can adapt to the curved front and back surfaces of a concha site. The pad face 306 has a relatively large area to minimize contact force. The housing 302 is injection molded of a pliant material. In one embodiment, the material is a medical grade thermoplastic elastomer.

FIGS. 2A-B and 3A-B, above, illustrate various ear sensor embodiments. Although described with respect to ear bud and flexible ear pad enclosures, the sensor emitter and detector may be enclosed in any number of housings having various sizes and shapes of ear tissue contact surfaces, may use various types of electrical interconnect and use various materials so as to noninvasively measure blood parameters from the concha area of the ear. As an example, the detector and emitter may both be mounted at one end of a "Y"-shaped flex circuit that has a connector at the opposite end. Although described above with respect to a detector placed inside the ear and an emitter placed outside the ear, a suitable alternative is the emitter inside and the detector outside the ear. Detector and emitter assemblies are described with respect to FIGS. 19-20, below.

FIGS. 4A-D illustrate "C"-clip embodiments 400 for attaching an ear sensor 410 to a concha site. The clip 400 is adapted for use with either the ear bud or the ear pad embodiments described above. The clip 400 has sensor mounts 420 fixedly attached to each end of a flexible "C"-shaped body 422. The body 422 is made of a suitable material having an appropriate stiffness so as to provide a comfortable yet secure attachment to ear tissue. The sensor mounts 420 have mounting apertures sized for the ear buds or ear pads described above. The ear buds or pads are secured within the apertures with a friction fit or adhesive. In an alternative embodiment, the sensor housings are molded or otherwise integrated with the sensor mounts.

Figures 4A, 4B, 4C, 4D:
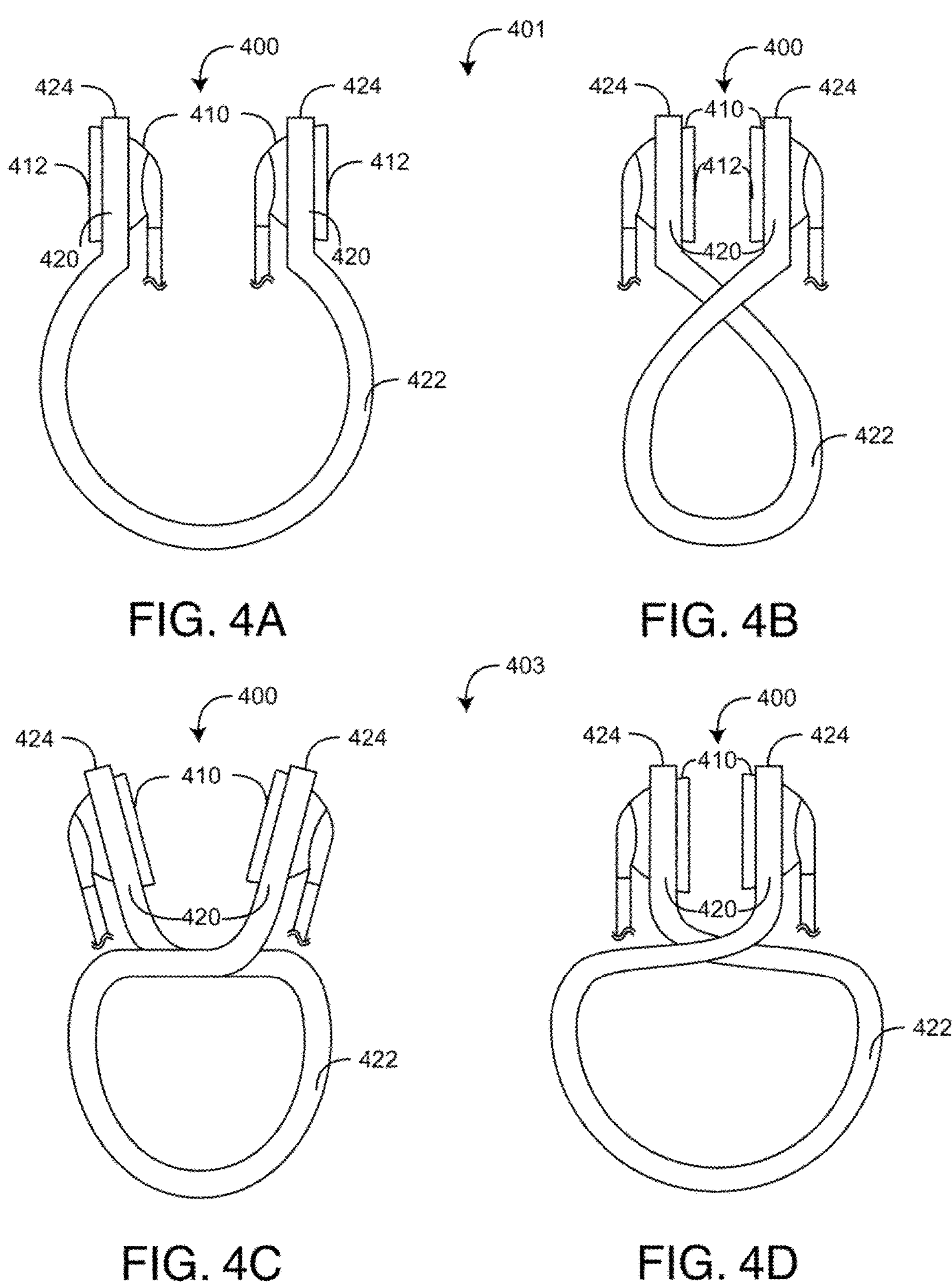
FIGS. 4A-D, 5A-B, 6A-B, and 7A-C illustrate various ear bud/pad attachment embodiments for a concha site.

As shown in FIGS. 4A-B, in one embodiment 401 the unflexed clip 400 (FIG. 4A) is compressed between fingertips so that the clip ends 424 are crossed (FIG. 4B) and the contact surfaces of the ear sensor 412 are facing each other. The clip 400 is placed over the ear so that the detector and emitter ear buds are on opposite sides of the ear. Finger pressure on the clip 400 is then released so that the clip tension holds the sensor contact surfaces 412 against the concha tissue. As shown in FIGS. 4C-D, in another embodiment 403 the clip ends 424 are crossed in both the flexed position (FIG. 4C) and the unflexed position (FIG. 4D). Otherwise, sensor attachment is as described above. Although described above as a "C"-shape, the clip body can be constructed of any of various springy, pre-formed materials having a variety of shapes and sizes so as to attach to ear tissue via compression and release between finger and thumb.

Figures 5A, 5B:
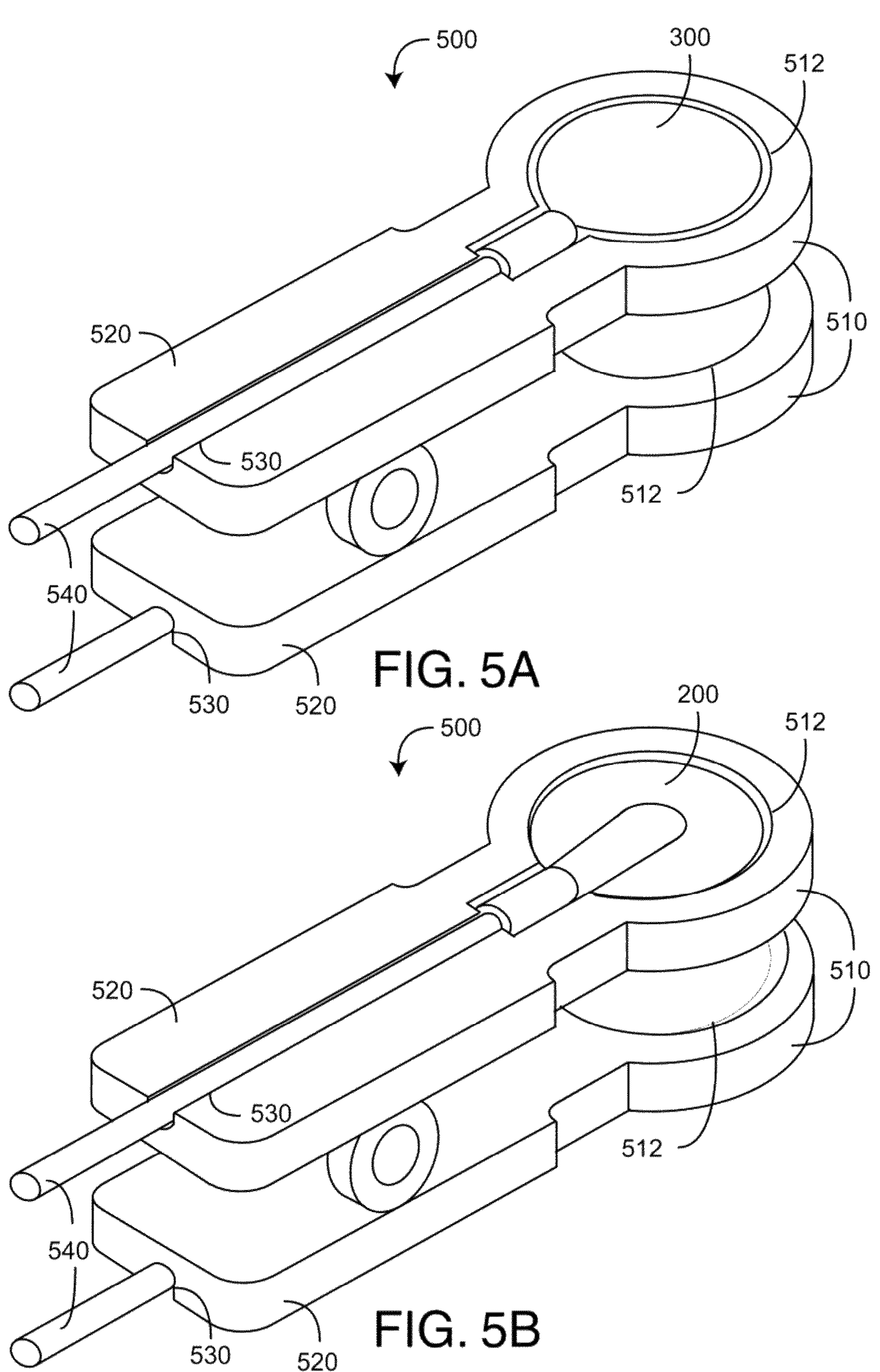

FIGS. 5A-B illustrate an alligator clip embodiment for attaching an ear sensor to a concha site. The alligator clip 500 has opposing heads 510, each with a thru-hole 512 sized to accommodate either an ear pad sensor 300 (FIG. 5A) or an ear bud sensor 200 (FIG. 5B). The alligator clip 500 also has finger grips 520 each with a channel 530 for routing the sensor cabling 540. The alligator clip is compressed and released to position and then attach the corresponding ear sensor to a concha site.

Figure 6A:
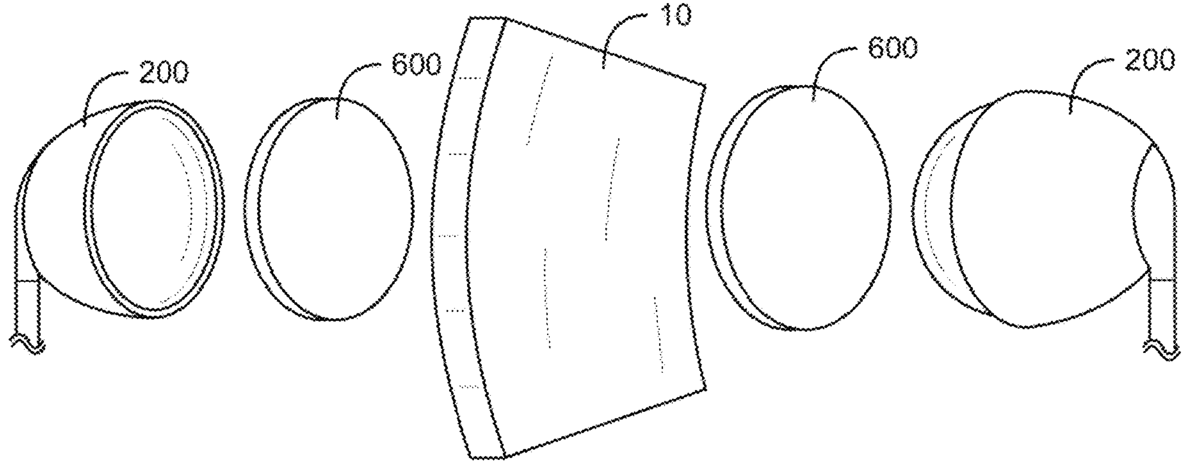
Figure 6B:
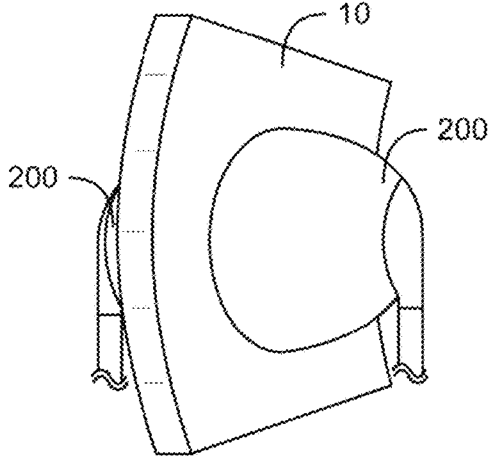

FIGS. 6A-B illustrate an adhesive disk embodiment for attaching an ear sensor to a concha site. Clear disks 600 have an adhesive on both surfaces. The adhesive is bio-compatible on at least the tissue-facing surface. The disks 600 are first attached to the sensor 200 or to a concha site 10. Then the ear sensor 200 is attached on opposite sides of the concha tissue 10. The disks 600 are sized to accommodate either an ear bud sensor 200, as shown, or an ear pad sensor 300 (FIGS. 3A-B).

Figure 7A:
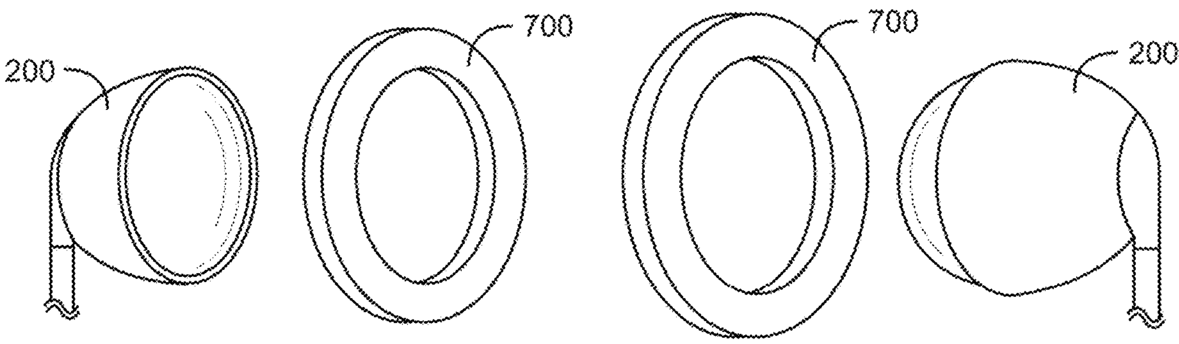
Figure 7B:
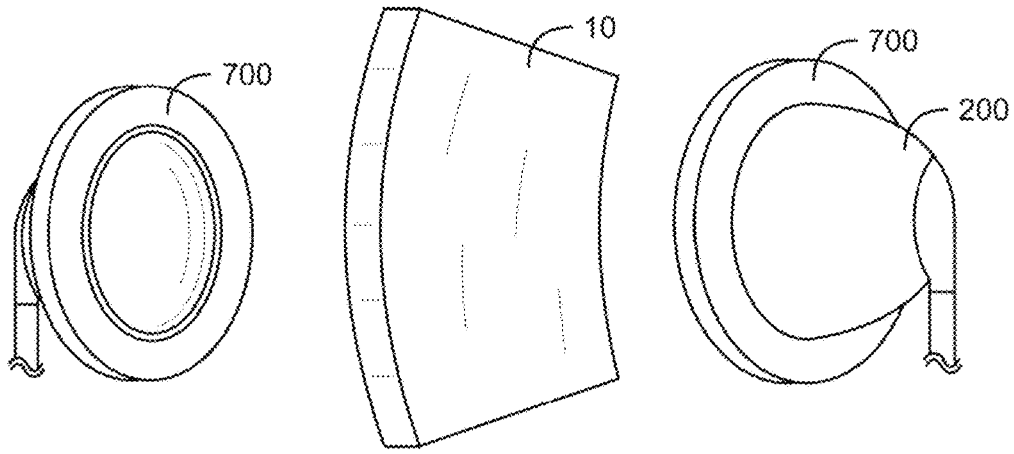
Figure 7C:
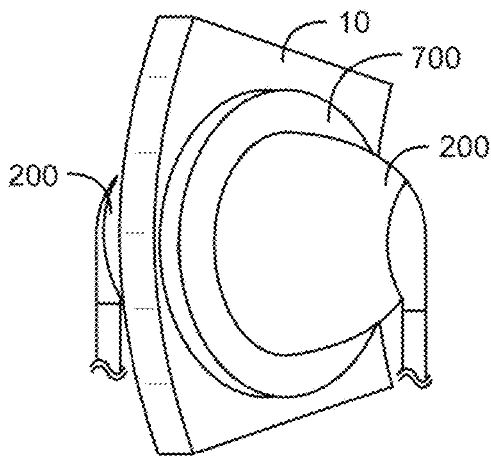

FIGS. 7A-C illustrate a flexible magnet disk embodiment for attaching an ear sensor to a concha site. Flexible magnetic disks 700, such as made from a mixture of a ferrite powder and a rubber polymer resin, are permanently or temporarily attached to an ear sensor 200. The attachment may be by friction fit or a removable or permanent adhesive. The ear sensor 200 is then placed on opposite sides of the concha site 10 and held in place by the magnetic force of the disks. One or both disks may be permanently magnetized during manufacture. The disks 700 are sized to accommodate either the ear bud sensor 200, as shown, or the ear pad sensor 300 (FIGS. 3A-B). In an alternative embodiment, each of the ear sensor housings is at least partially composed of a high magnetic permeable material. One or both of the housings are magnetized. In another embodiment, one or more rare earth magnets are embedded in one or both housings.

FIGS. 4A-D, 5A-B, 6A-B, and 7A-C, described above, illustrate various ear sensor attachment embodiments. Although described with respect to clips and adhesive or magnetic disks, the sensor emitter and detector may be attached to an ear tissue site using various other materials and mechanisms. For example, ear buds or pads may attach via suction cups or disks. Also, an emitter and detector may be integrated with disposable adhesive pads configured with snaps or other mechanical connectors for attaching and removing sensor leads from the disposable pads. In another embodiment, a sensor may be mounted in the concha or the ear canal using an expanding foam material that is first squeezed and then released after sensor placement within the ear.

Figures 8A, 8B:
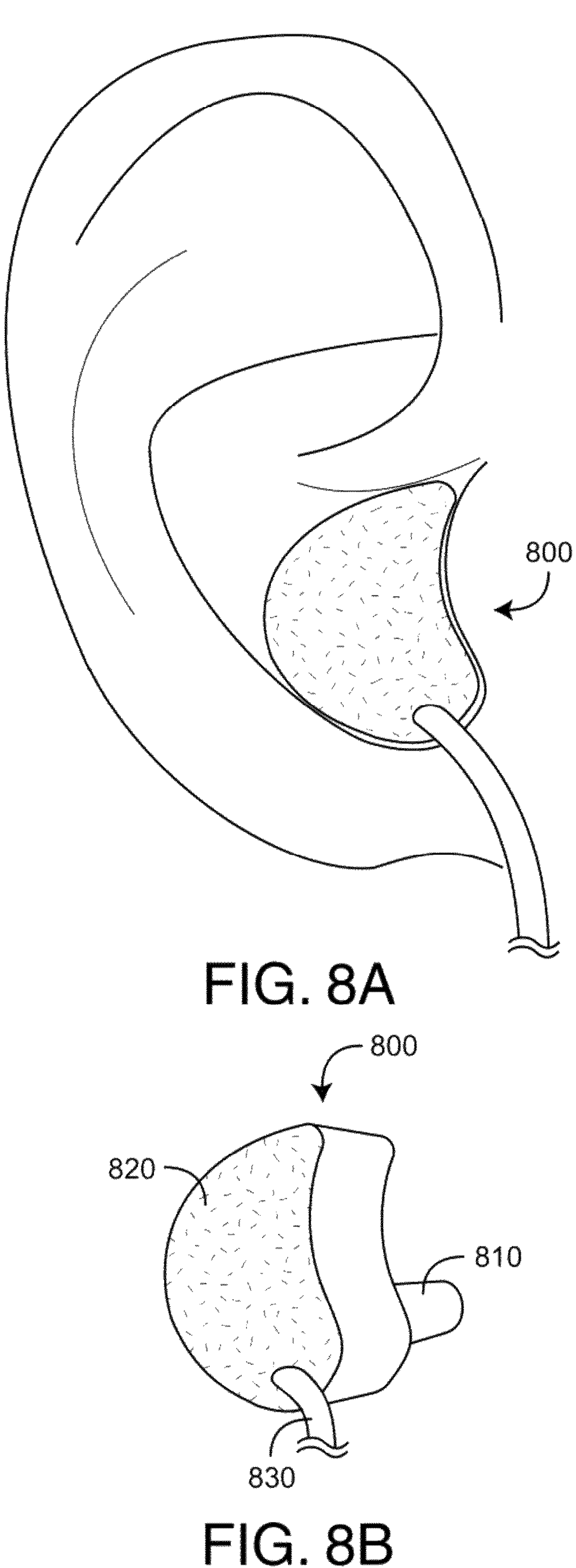
FIGS. 8A-B, 9A-B, and 10A-B illustrate various "hearing aid" style ear sensor embodiments that integrate the ear sensor with an attachment mechanism.

FIGS. 8A-B illustrate a concha-placed reflective sensor embodiment. In one embodiment the sensor 800 has an ear canal extension 810 (FIG. 8B). In an embodiment, the ear canal extension has at least one emitter and at least one detector disposed proximate the extension surface so as to transmit light into ear canal tissue and to detect the transmitted light after attenuation by pulsatile blood flow within the ear canal tissue. In an embodiment, the emitter and detector are axially spaced on the extension. In an embodiment, the emitter and detector are radially spaced on the extension at a fixed angle, which may be, as examples, 30, 45, 90, 120, 135, 160 or 180 degrees.

In an embodiment, the concha-placed sensor body 820 has at least one emitter and at least one detector in lieu of an ear canal extension emitter and detector. The sensor body emitter and detector are disposed proximate the concha surface so as to transmit light into concha tissue and to detect the transmitted light after attenuation by pulsatile blood flow within the concha tissue. In an embodiment, the concha-placed sensor body 820 and the ear canal extension 810 both have at least one emitter and at least one detector, creating a multi-site (concha and ear canal) reflective sensor. Connected with the sensor body 820 is a sensor cable 830 providing electrical communications between sensor body/ear canal emitter(s) and detector(s) and a monitor. Detector and emitter assemblies are described with respect to FIGS. 19-20, below.

Figure 9A:
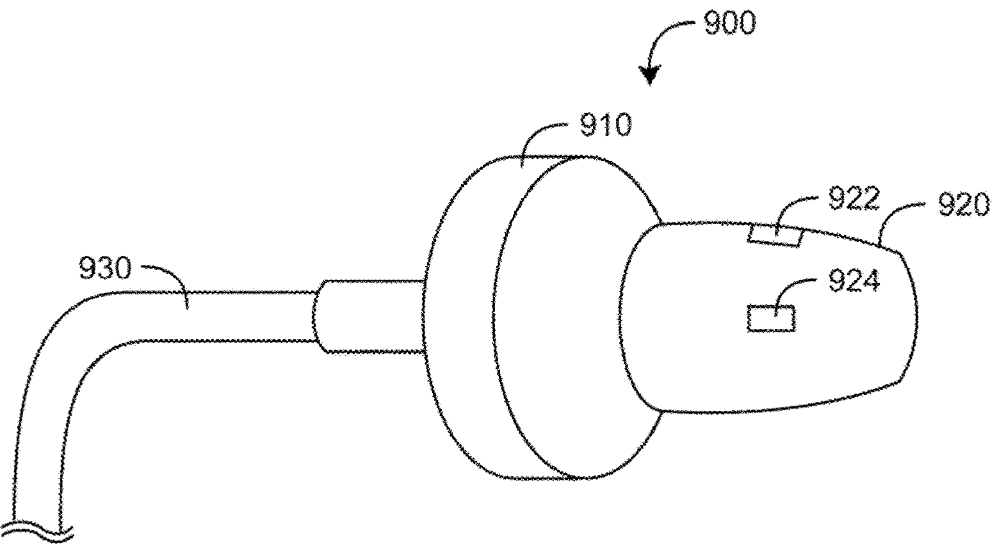
Figure 9B:
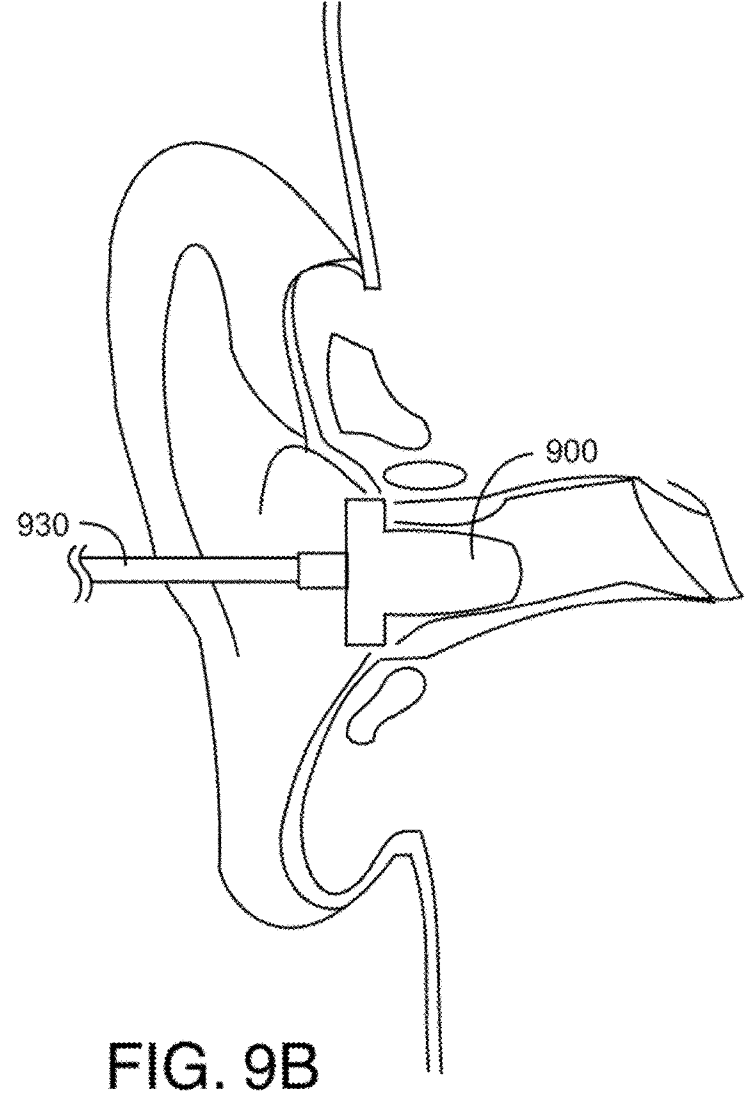

FIGS. 9A-B illustrate an "in-the-canal" ear sensor embodiment. The ear canal sensor 900 has a base 910, an ear canal extension 920 and a sensor cable 930. Similar to the embodiment described above, the ear canal extension 920 has at least one emitter 922 and at least one detector 924 disposed proximate the extension surface so as to transmit light into ear canal tissue and to detect the transmitted light after attenuation by pulsatile blood flow within the ear canal tissue. The emitter 922 and detector 924 may be axially-spaced on the ear canal extension a fixed distance. Alternatively, the emitter and detector may be radially-spaced on the ear canal extension at any of various angles, such as 30, 45, 90, 120, 135, 160 or 180 degrees, to name a few. A sensor cable 930 is attached to the sensor so as to extend from the ear canal to a corresponding monitor.

Figures 10A, 10B:
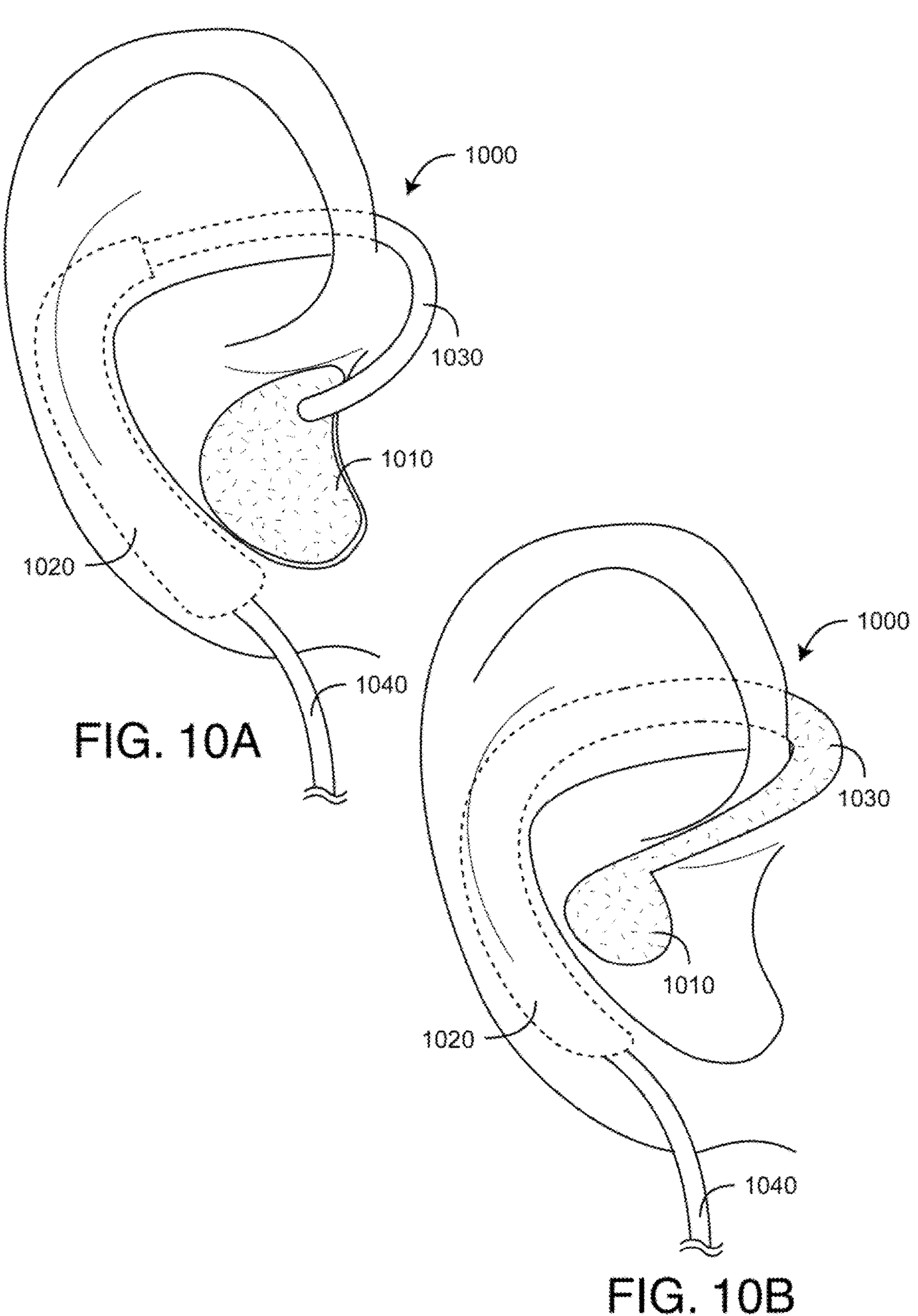

FIGS. 10A-B illustrate "behind-the-ear" transmissive and/or reflective sensor embodiments. The ear sensor 1000 has a concha-placed body 1010, an ear piece 1020, a connecting piece 1030 attaching the concha body 1010 and the ear piece 1020 and a sensor cable 1040. In one embodiment, a concha-placed body 1010 houses a detector and the ear piece 1020 houses an emitter opposite the detector so as to configure a transmissive concha sensor. In an embodiment, the concha-placed body 1010 or the ear piece 1020 has both an emitter and a detector so as to configure a reflective concha sensor. In an embodiment, the concha body 1010 and the ear piece 1020 are configured for multi-site transmissive and/or reflective concha tissue measurements. In an embodiment, the concha body 1010 also has an ear canal extension (see, e.g. 810 FIG. 8B), which may also have an emitter and detector for multi-site concha and ear canal measurements. A sensor cable 1040 extends from the ear piece 1020 as shown. Alternatively, a sensor cable extends from the concha body, such as shown in FIG. 8B, above.

Figures 11A, 11B:
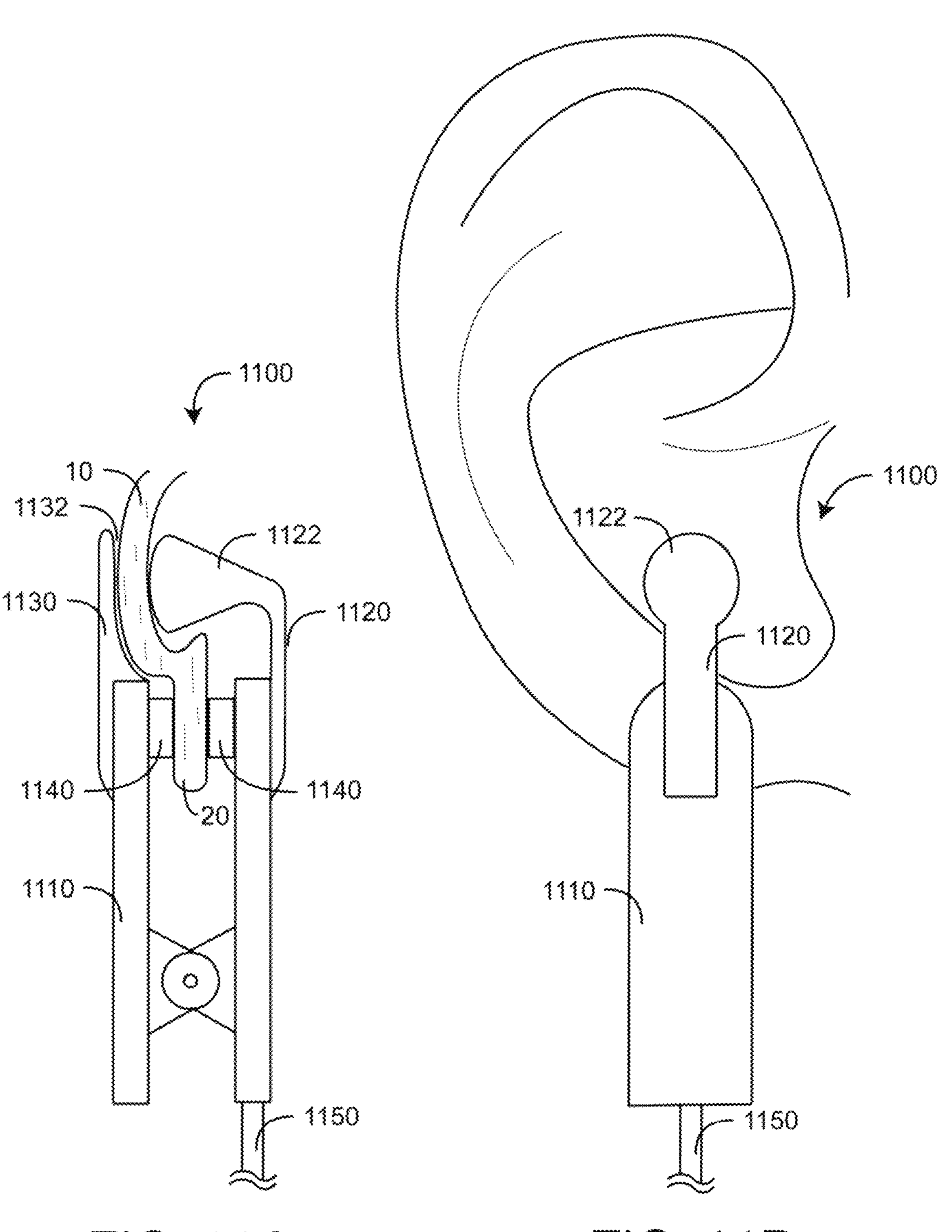
FIGS. 11A-B and 12A-F illustrate additional integrated ear sensor and attachment embodiments.
Figure 12A:
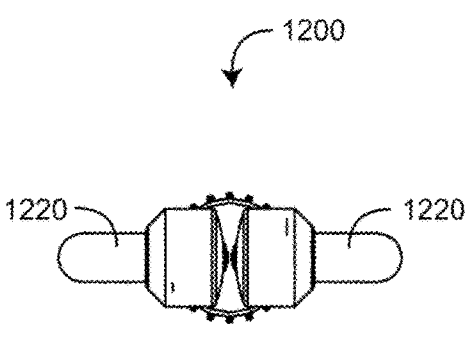
Figure 12B:
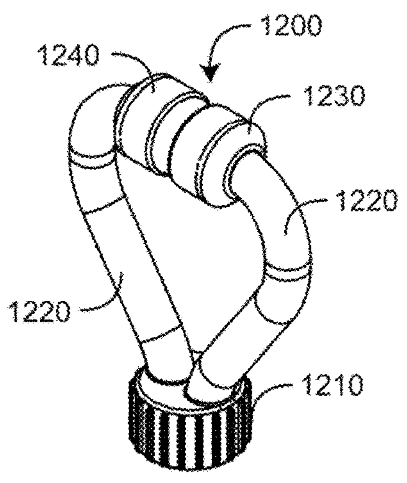
Figure 12C:
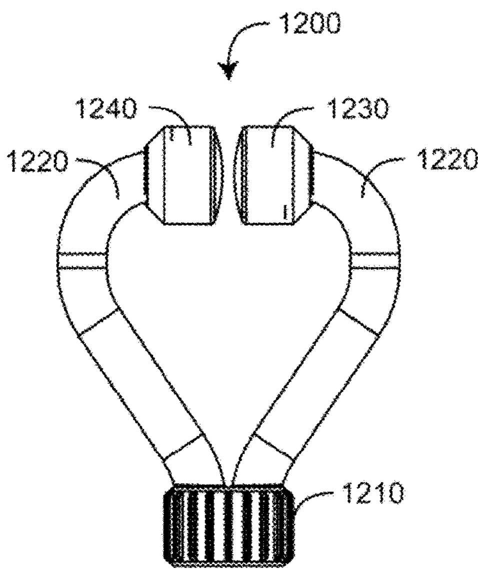
Figure 12D:
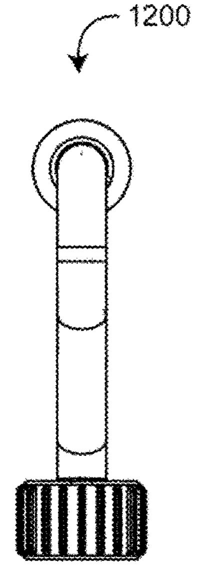
Figure 12E:
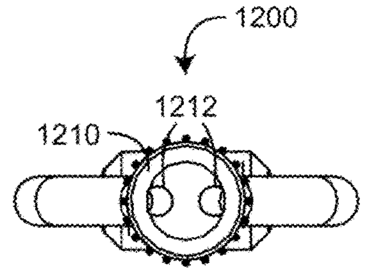
Figure 12F:
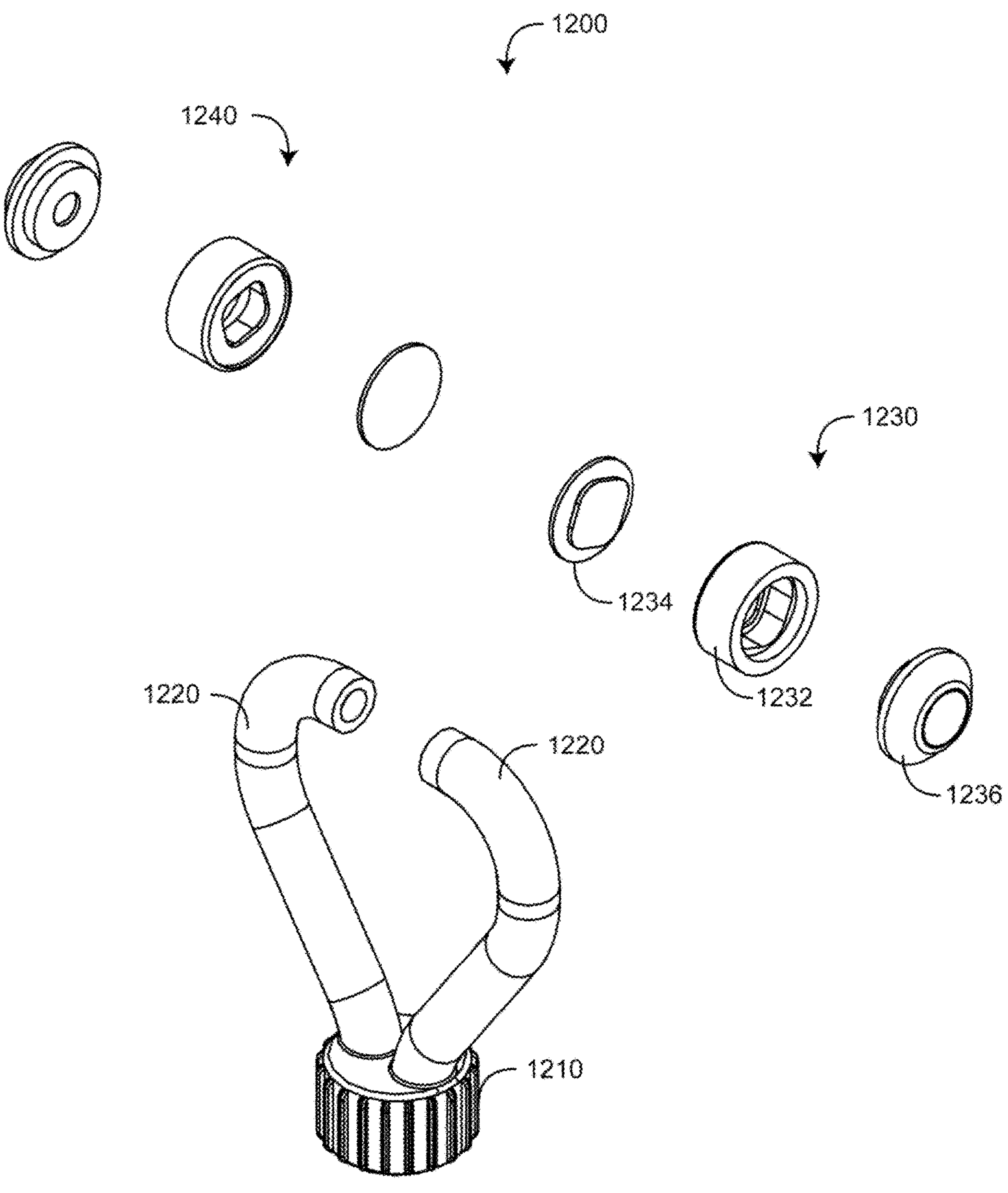
Figure 13A:
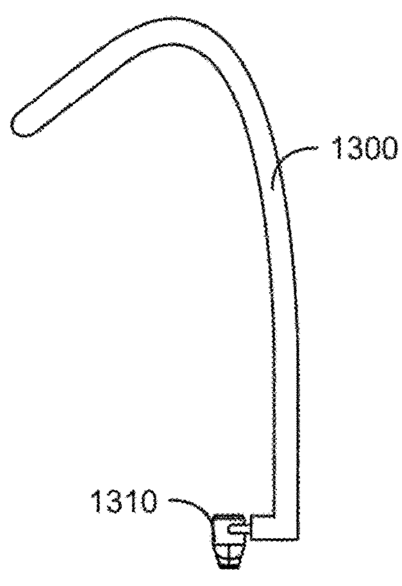
FIGS. 13A-F, 14A-B, 15A-B, and 16 illustrate various ear sensor attachment support embodiments.
Figure 13B:
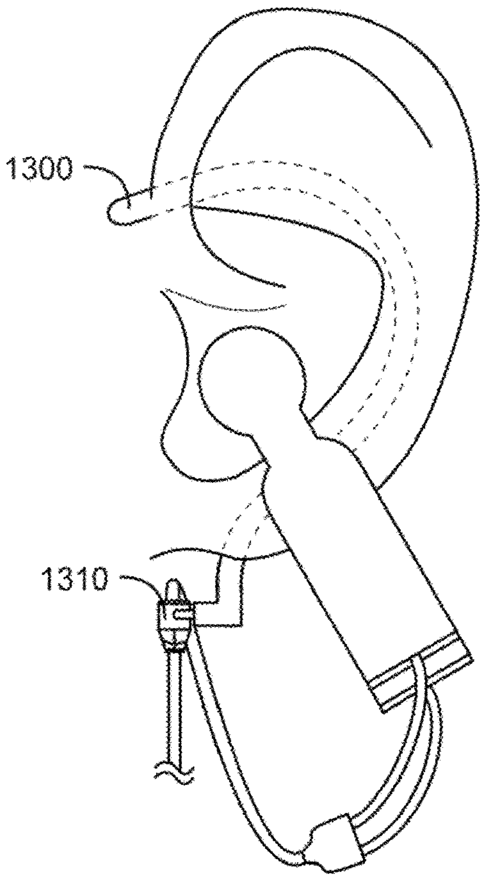
Figure 13C:
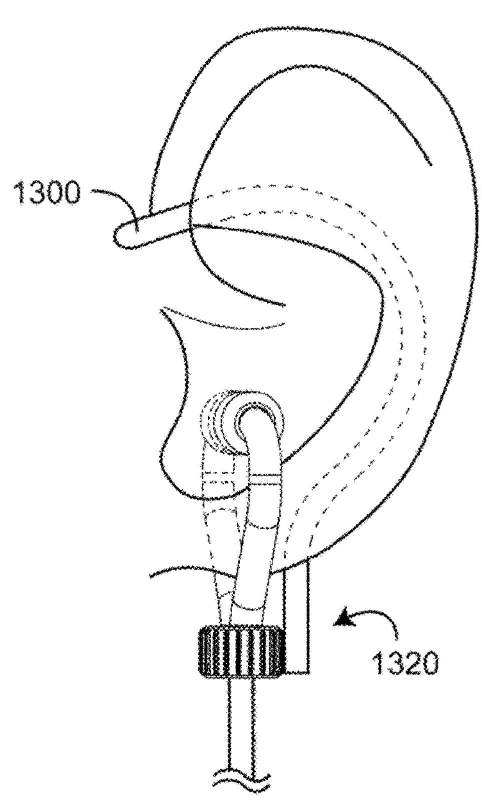
Figure 13D:
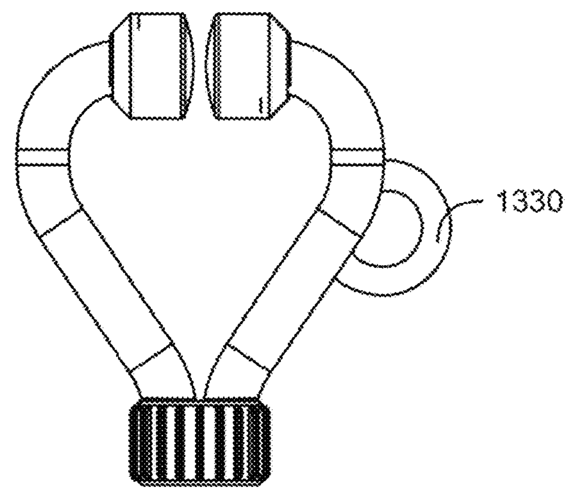
Figure 13E:
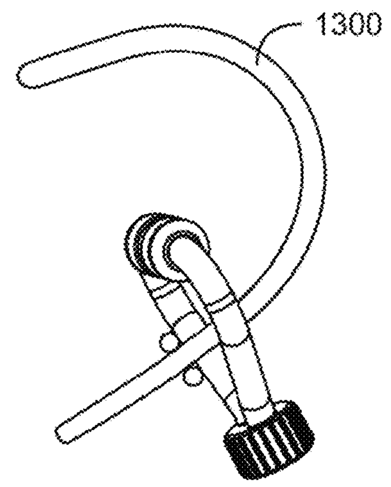
Figure 13F:
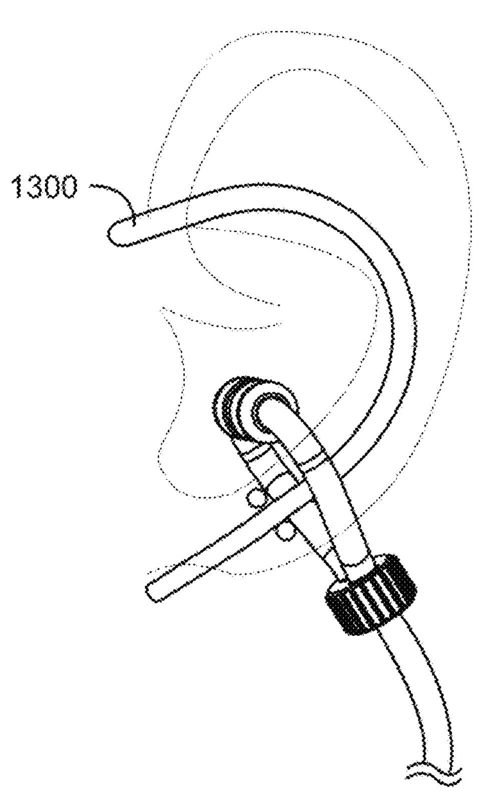

FIGS. 11A-B illustrate a concha sensor 1100 having an alligator clip 1110, a concha piece 1120, a ear back piece 1130, a lobe attachment 1140 and a sensor cable 1150. In an embodiment, the alligator clip 1110 attaches to the ear lobe 20 so as to provide the physical support for a concha sensor 1100. A convex body 1122 extends from the concha piece 1120. A detector disposed at the convex body 1122 surface is disposed against the concha tissue 10. A concave surface 1132 is defined on the back piece 1130 and positioned behind the ear. An emitter disposed at the concave surface 1132 is disposed against the ear wall opposite the concha detector. The concha piece 1120 and ear back piece 1130 are "springy" so as to securely contact the concha tissue 10 under the force of the alligator clip 1110, but without undue discomfort. In an embodiment, the lobe attachment 1140 also has an emitter and detector so as to provide multi-site ear tissue measurements at the ear lobe 20 and the concha 10.

FIGS. 12A-F illustrate a "Y"-clip ear sensor 1200 having a base 1210, a pair of curved clips 1220 extending from the base, an emitter assembly 1230 extending from one clip end and a detector assembly 1240 extending from another clip end. The clips 1220 are tubular so as to accommodate wires from the emitter/detector assemblies, which extend from apertures 1212 in the base. Each assembly has a pad 1232, a molded lens 1234 and a lid 1236, which accommodate either an emitter subassembly or a detector subassembly. The Y-"clips" flex so as to slide over the ear periphery and onto either side of the concha. The integrated emitter and detector, so placed, can then transmit multiple wavelength light into the concha tissue and detect that light after attenuation by pulsatile blood flow within the concha tissue.

FIGS. 13A-F illustrate ear hook sensor support embodiments having an ear hook 1300 with cable 1310, fixed 1320 or sliding 1330 support for either an alligator clip or a "Y"-clip sensor. These embodiments are also applicable to "C"-clip sensors and alligator clip sensors, among others.

Figure 14A:
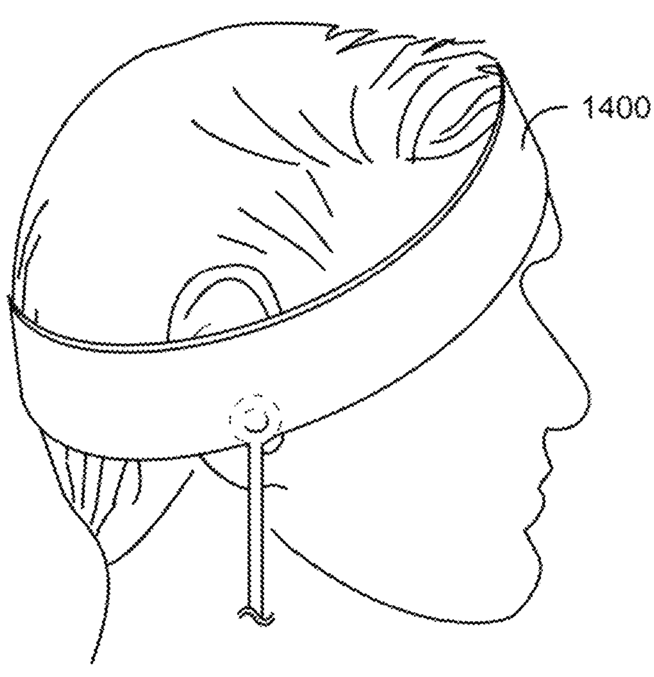
Figure 14B:
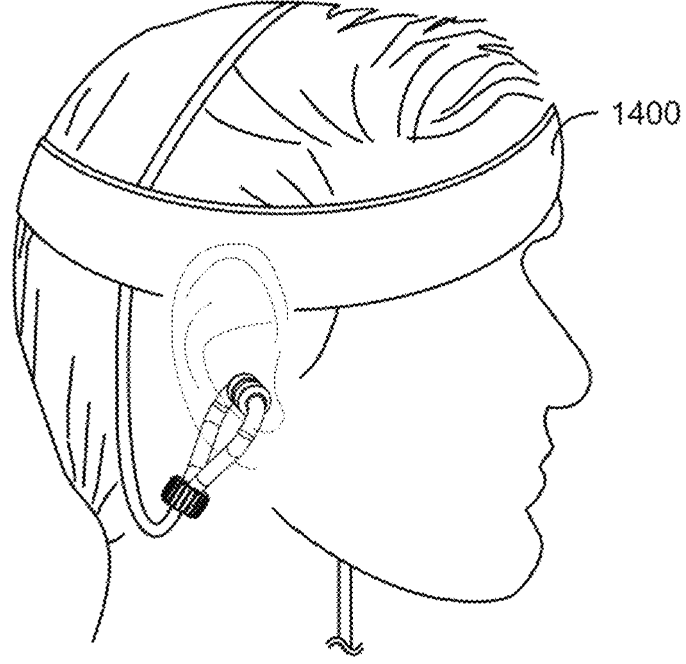

FIGS. 14A-B illustrate headband sensor support embodiments. In one embodiment, the headband 1400 secures a concha body (FIGS. 8A-B) or an ear canal sensor (FIGS. 9A-B) by placement over the ear. In another embodiment, the headband 1400 provides a cable support for an ear clip sensor.

Figure 15A:
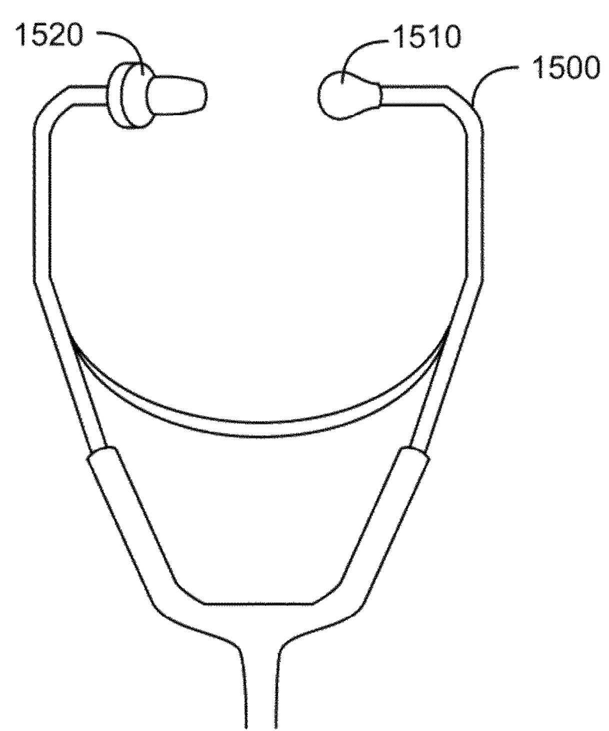
Figure 15B:
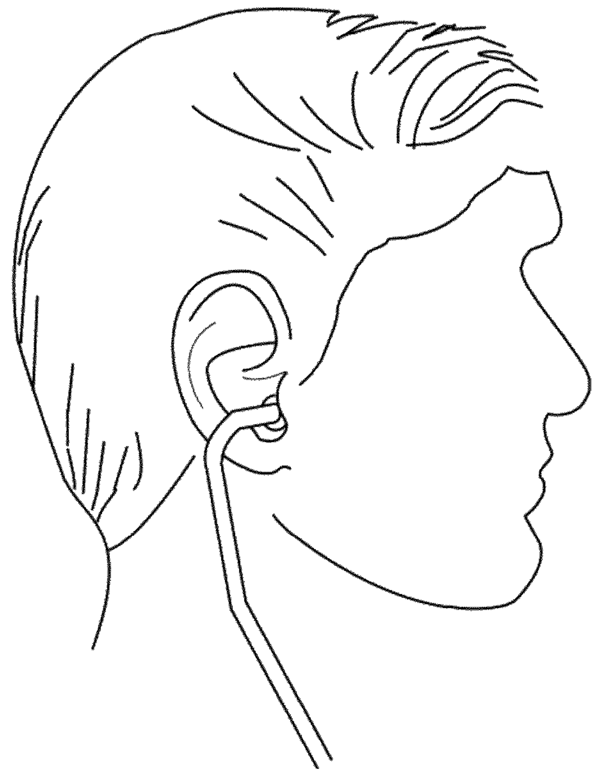

FIGS. 15A-B illustrate a "stethoscope" 1500 sensor support embodiment. In this embodiment, one ear piece 1510 is integrated with an ear canal sensor 1520, such as described above with respect to FIGS. 9A-B. In another embodiment, both stethoscope ear pieces 1510 are integrated with ear canal sensors for multi-site (both ears) blood parameter measurements.

Figure 16:
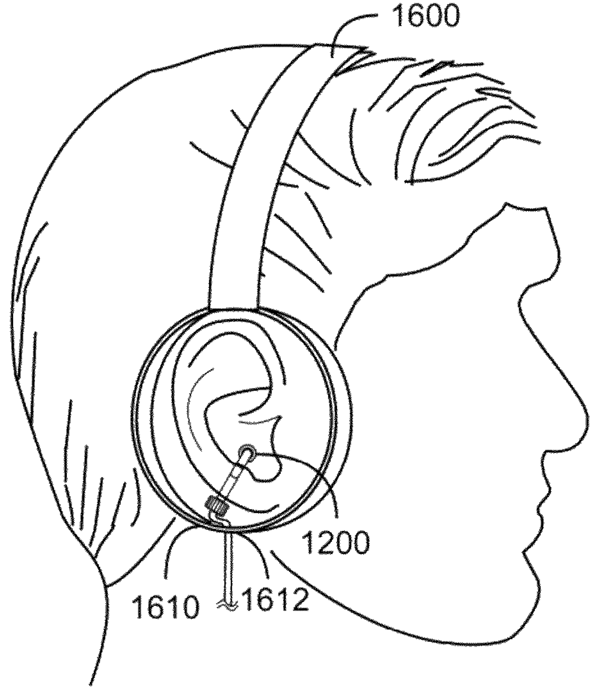

FIG. 16 illustrates a "headphone" 1600 support embodiment. In one embodiment (not shown), a headphone ear piece secures a concha body (FIGS. 8A-B) or an ear canal sensor (FIGS. 9A-B) by placement over the ear, in a similar manner as described with respect to FIGS. 14A-B. In another embodiment, the headphone 1600 provides a "ring-shaped" earpiece 1610 that provides a cable support 1612 for an ear clip sensor 1200, as shown.

Figures 17A, 17B:
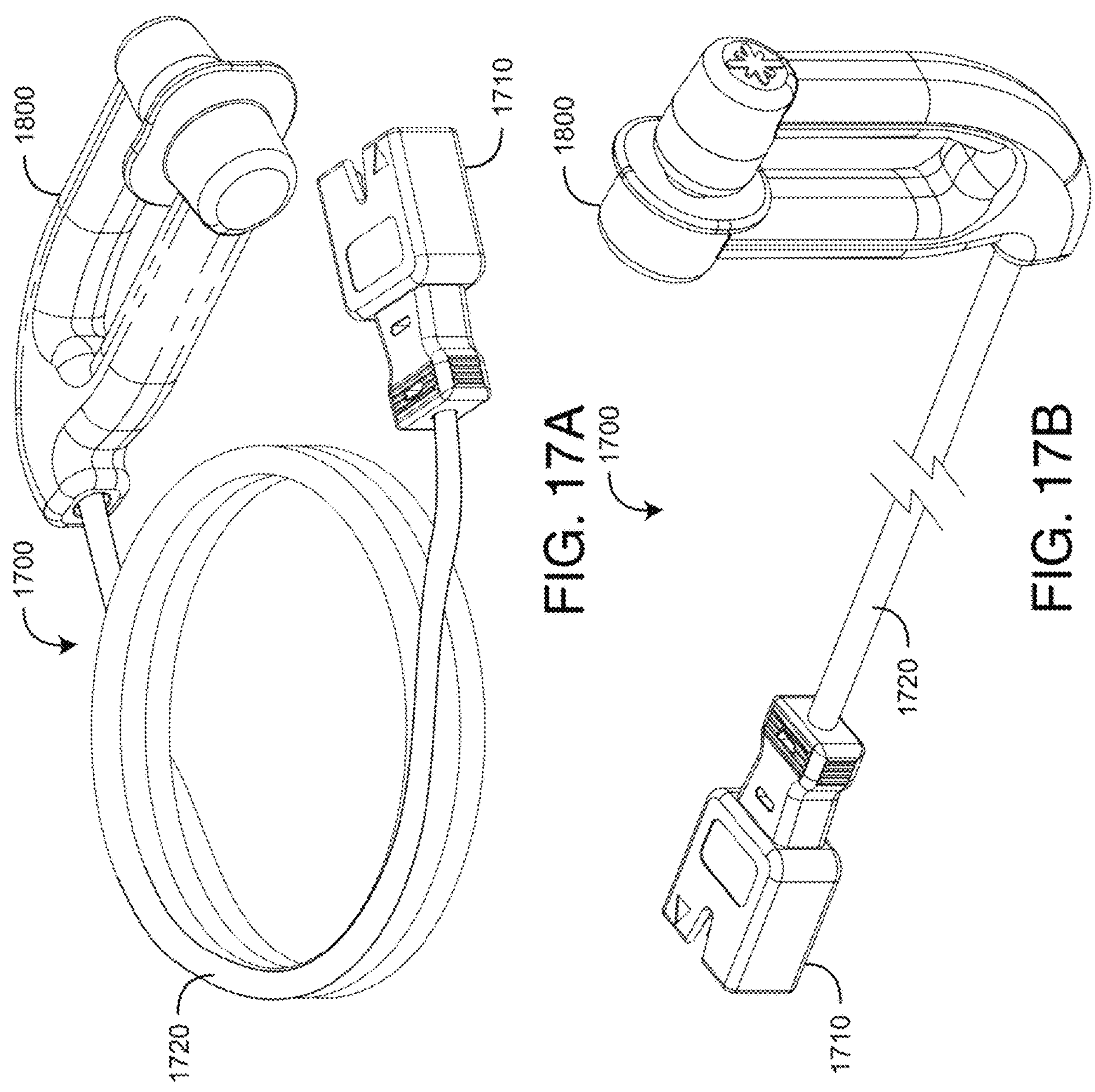
FIGS. 17A-B, 18A-E, 19, 20A-B, 21A-B, 22A-B, 23A-B, 24A-C, 25A-E, 26A-F, and 27A-F illustrate a concha-clip sensor embodiment having an orthogonally-routed sensor cable.
Figures 18A, 18B, 18C, 18D, 18E:
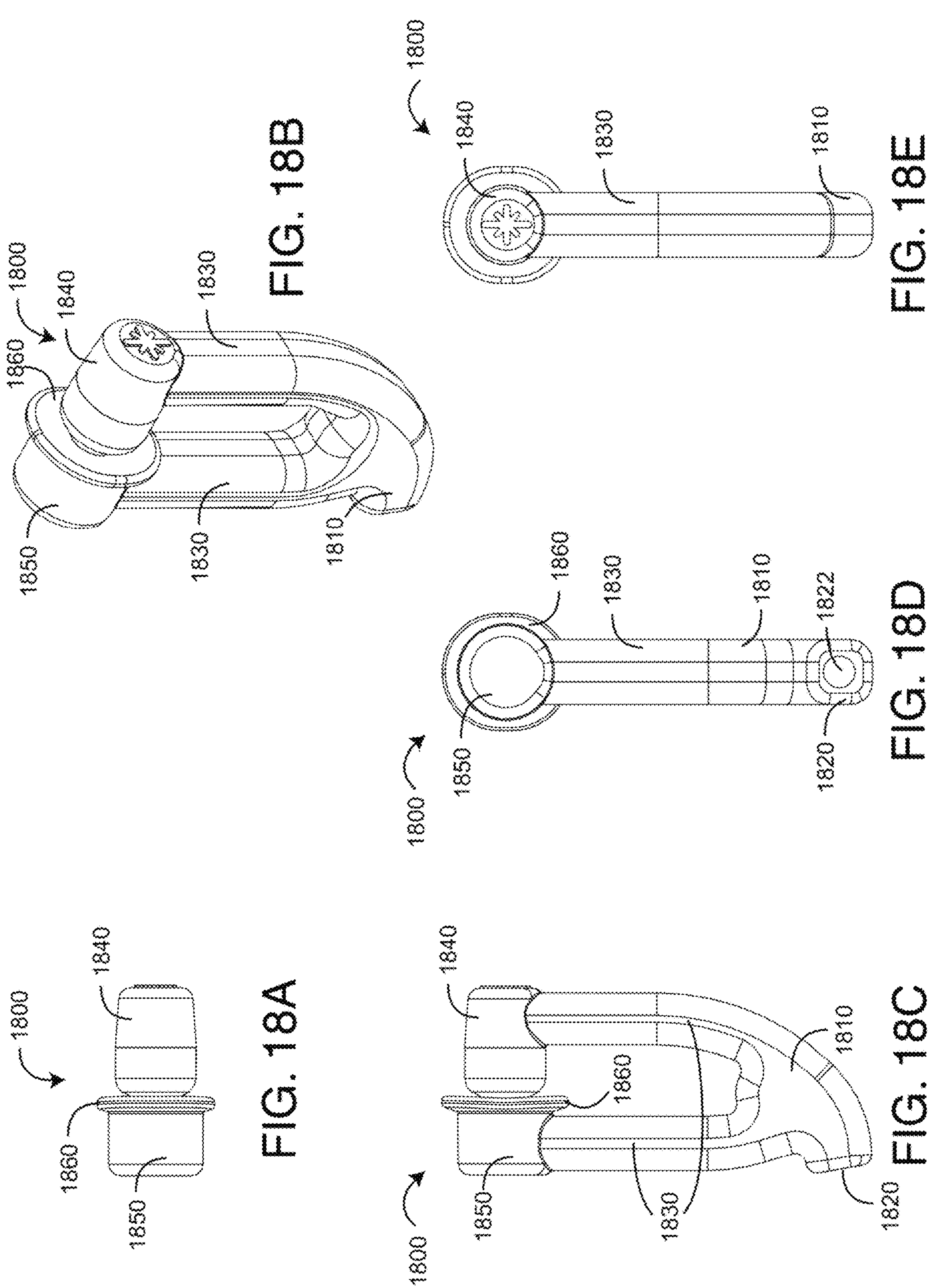

FIGS. 17A-B illustrate a concha-clip ear sensor 1700 embodiment having a sensor body 1800, a connector 1710 and a sensor cable 1720 providing communications between the sensor body 1800 and the connector 1710. As described in further detail with respect to FIGS. 18A-E, the sensor body 1800 has resilient legs that are manually flexed so as to slide over an ear periphery and onto either side of a concha site. As described in further detail with respect to FIG. 19, the sensor body 1800 incorporates an optical assembly 1910 (FIG. 19) configured to transmit multiple wavelength light into the concha tissue and detect that light after attenuation by pulsatile blood flow within the concha tissue. In a particular embodiment, the sensor body 1800 has an emitter housing 1840 (FIGS. 18A-E) configured to fit inside the ear and a detector housing 1850 (FIGS. 18A-E)

configured to fit outside the ear. In other embodiments, the sensor body is configured so as to place an emitter outside the ear and a detector inside the ear. In an embodiment, the sensor body 1800 is configured so that the sensor cable 1720 extends generally perpendicular to the sensor body 1800, as shown and described with respect to FIGS. 17-26. In another sensor body embodiment 2700 (FIGS. 27A-F) the sensor cable 1720 extends generally parallel to the sensor body, as described in further detail with respect to FIGS. 27A-E, below. Although the sensor body 1800, 2700 as described below has legs 1830 extending from a base 1810 so as to generally form a "U"-shape, the sensor body 1800, 2700 can be constructed of any of various resilient, pre-formed materials having a variety of shapes and sizes so as to attach to ear tissue, such as a concha site or ear lobe site.

FIGS. 18A-E further illustrate a sensor body 1800 having a base 1810, a strain relief 1820 formed at a side of the base 1810 and a pair of resilient legs 1830 extending from the base 1810. The strain relief 1820 has a cable aperture 1822 that accommodates the sensor cable 1720 (FIGS. 17A-B). An emitter housing 1840 extends from one leg 1830 and a detector housing 1850 extends from the other leg 1830. The legs 1830 accommodate cable conductors extending between the connector 1710 (FIGS. 17A-B) and an optical assembly 1910 (FIG. 19) located in the housings 1840, 1850. Each housing 1840, 1850 has an optical end 1842, 1852 (FIG. 20B) having an aperture 1844, 1854 (FIG. 20B) that passes light from the emitter housing 1840 to the detector housing 1850. In an embodiment, the housings 1840, 1850 fit on either side of a concha tissue site so that light is transmitted from an emitter 1916 (FIG. 19), through the concha tissue and received by a detector 1912 (FIG. 19), as described in detail below. In an embodiment, the emitter housing 1840 fits within the ear and the detector housing 1850 outside the ear. In an embodiment, a cup 1860 extends from the detector housing 1850. The cup 1860 has a generally circular edge and a curvature that accommodates the surface behind the ear. Accordingly, the cup 1860 advantageously provides a more comfortable and secure fit of the detector housing 1850 to the ear and further functions as a light shield, blocking external light sources from the detector 1912. The resilient legs 1830 are manually flexed so that the emitter housing 1840 is moved away from the detector housing 1850 so as to position the detector housing 1850 and emitter housing 1840 over opposite sides of a concha site. The legs are then released to an unflexed position so that the concha site is grasped between the detector housing 1850 and emitter housing 1840.

Figure 19:
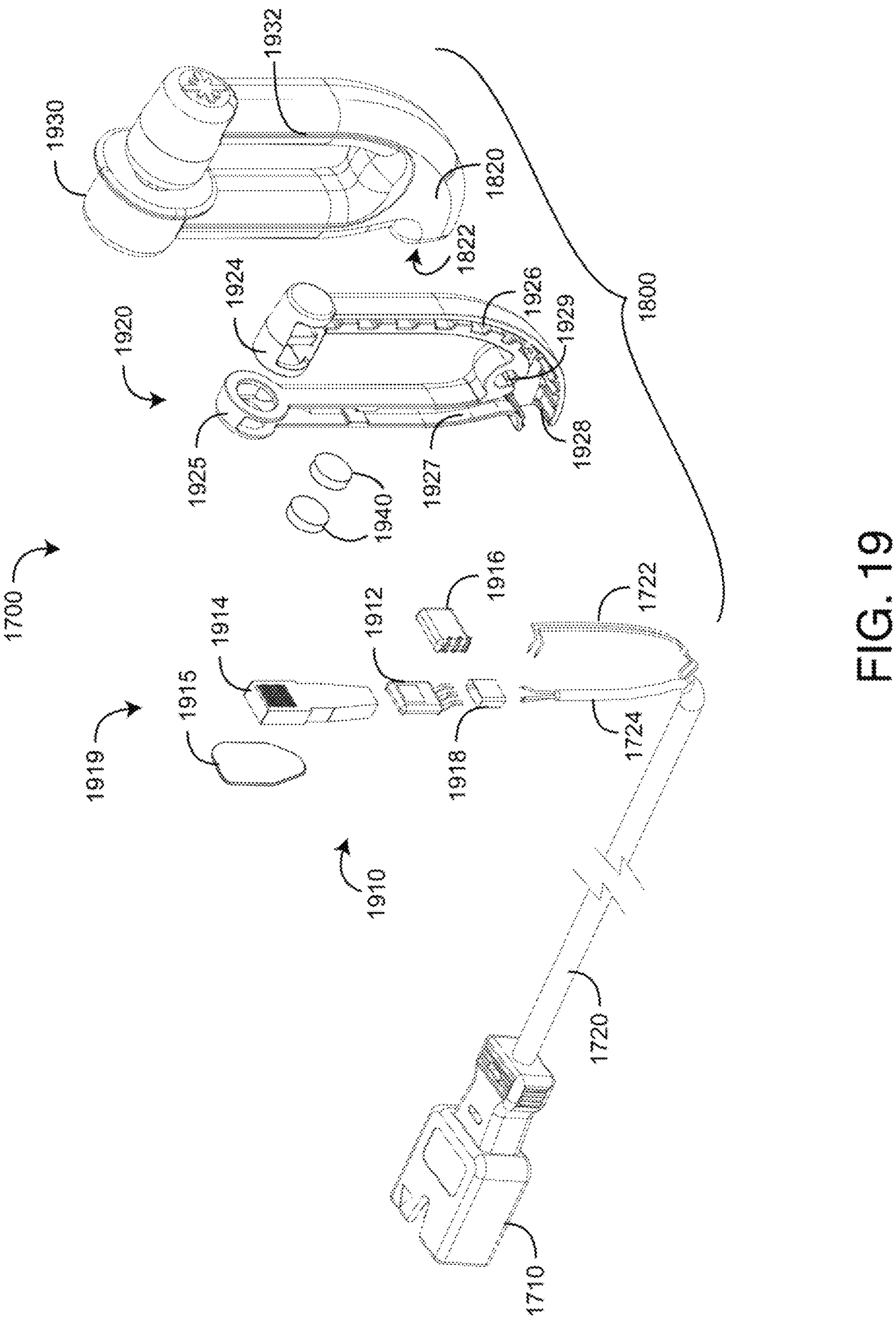
Figures 20A, 20B:
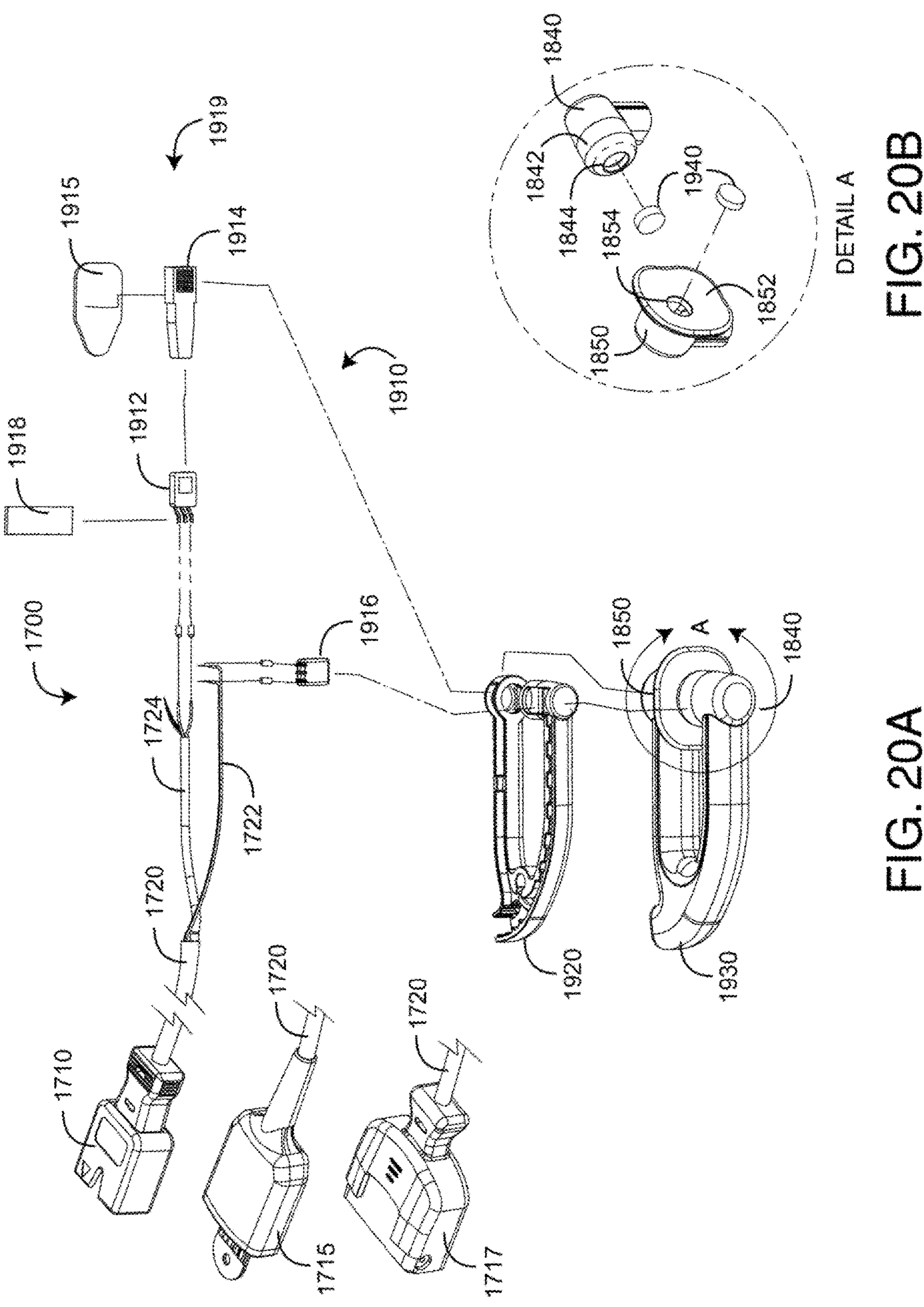
Figures 21A, 21B:
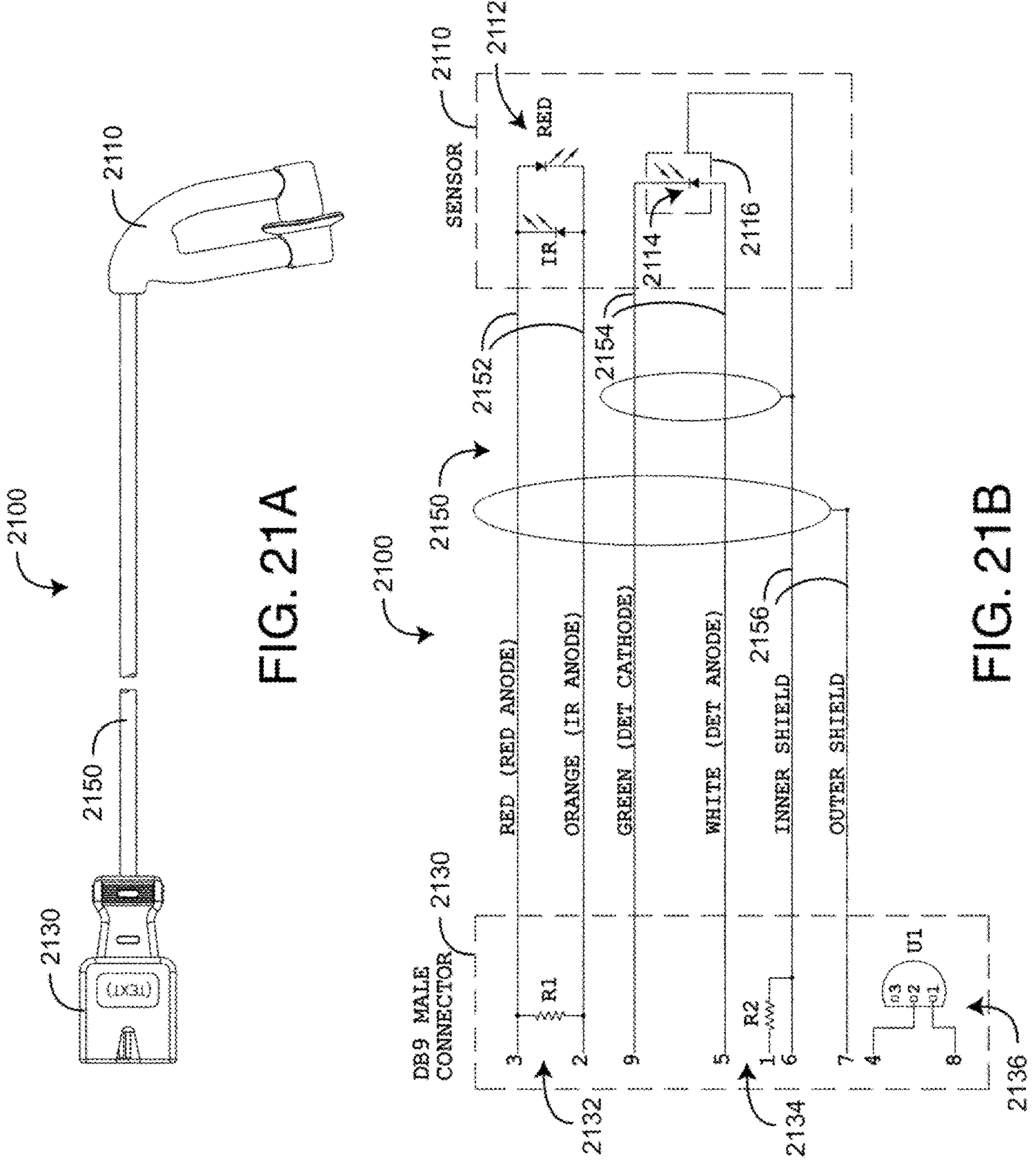
Figures 22A, 22B:
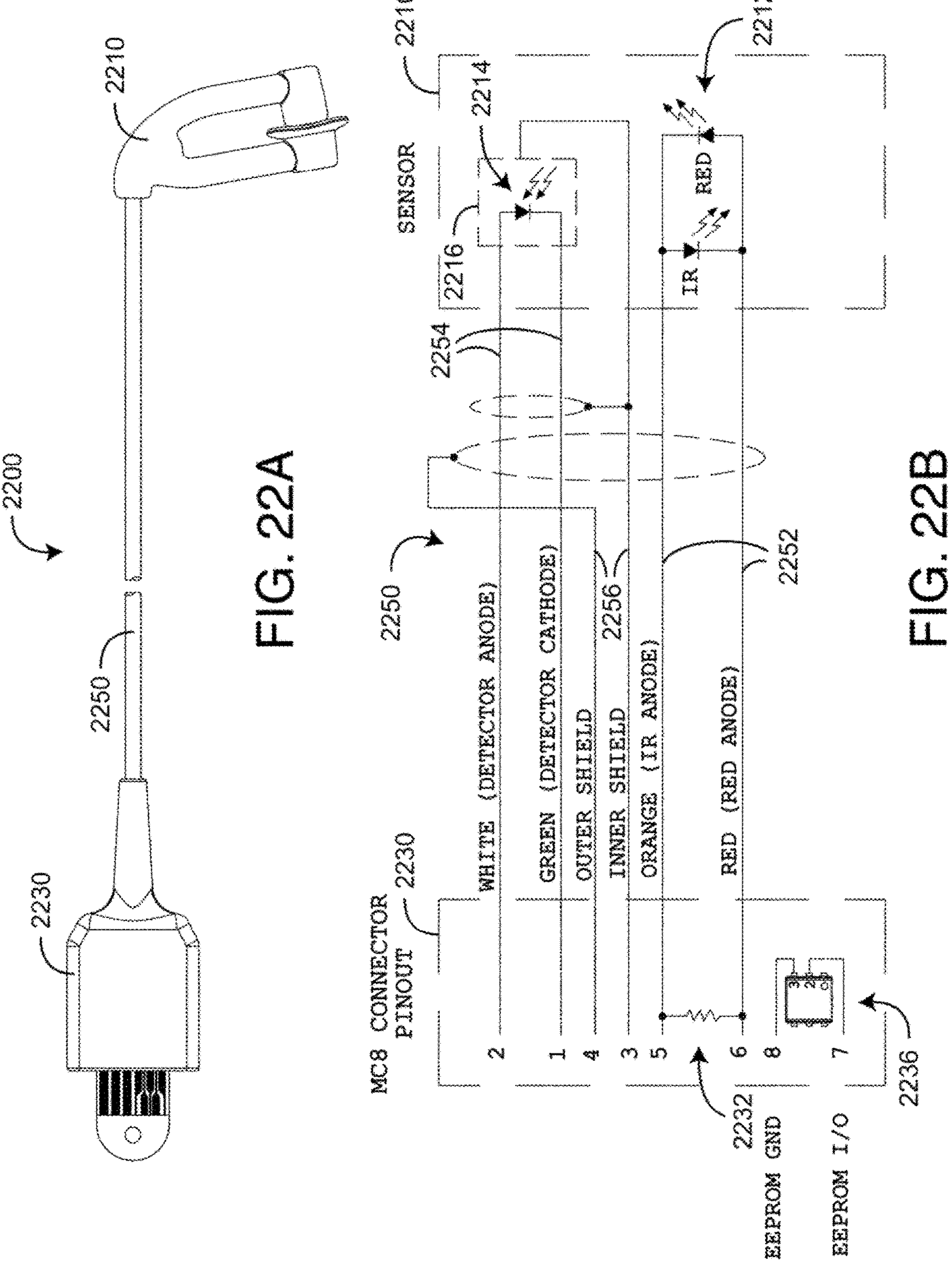

FIGS. 19, 20A-B further illustrates a concha-clip ear sensor 1700 having a connector 1710 in communications with a sensor body 1800 via a sensor cable 1720. The sensor body 1800 has an optical assembly 1910, a resilient frame 1920, a sensor housing 1930 and lenses 1940. As shown in FIGS. 19-20, the optical assembly 1910 has a detector 1912, a detector shield 1914, a light barrier 1915, an emitter 1916 and white electrical tape 1918. The cable 1720 has emitter wires 1722 and detector wires 1724 that are soldered to the emitter 1916 and detector 1912, respectively, and communicate emitter drive signals and detector response signals to/from the connector 1710.

Also shown in FIGS. 19, 20A-B, the resilient frame 1920 has an emitter channel 1926 terminating at an emitter holder 1924, a detector channel 1927 terminating at a detector holder 1925, a strain relief 1928 and a frame hole 1929. The optical assembly 1910 fits within the resilient frame 1920. In particular, the emitter wires 1722 are disposed within the emitter channel 1926, the detector wires 1724 are disposed in the detector channel 1927, the emitter is disposed in the emitter holder 1924 and the detector 1912 and corresponding shield 1914 and light barrier 1915 are disposed in the detector holder 1925. In an embodiment, the sensor housing 1930 is a one piece silicon skin disposed over the resilient frame 1920 and the optical assembly 1910, as described with respect to FIGS. 24A-C, below. In an embodiment, the resilient frame 1920 is a polypropylene/santoprene blend. The lenses 1940 are disposed within housing apertures 1844, 1854. In an embodiment, the lenses 1940 are formed from a translucent silicone adhesive. In an alternative embodiment, the lenses 1940 are separately formed from clear silicone and glued into place with a translucent silicone adhesive.

Figures 23A, 23B:
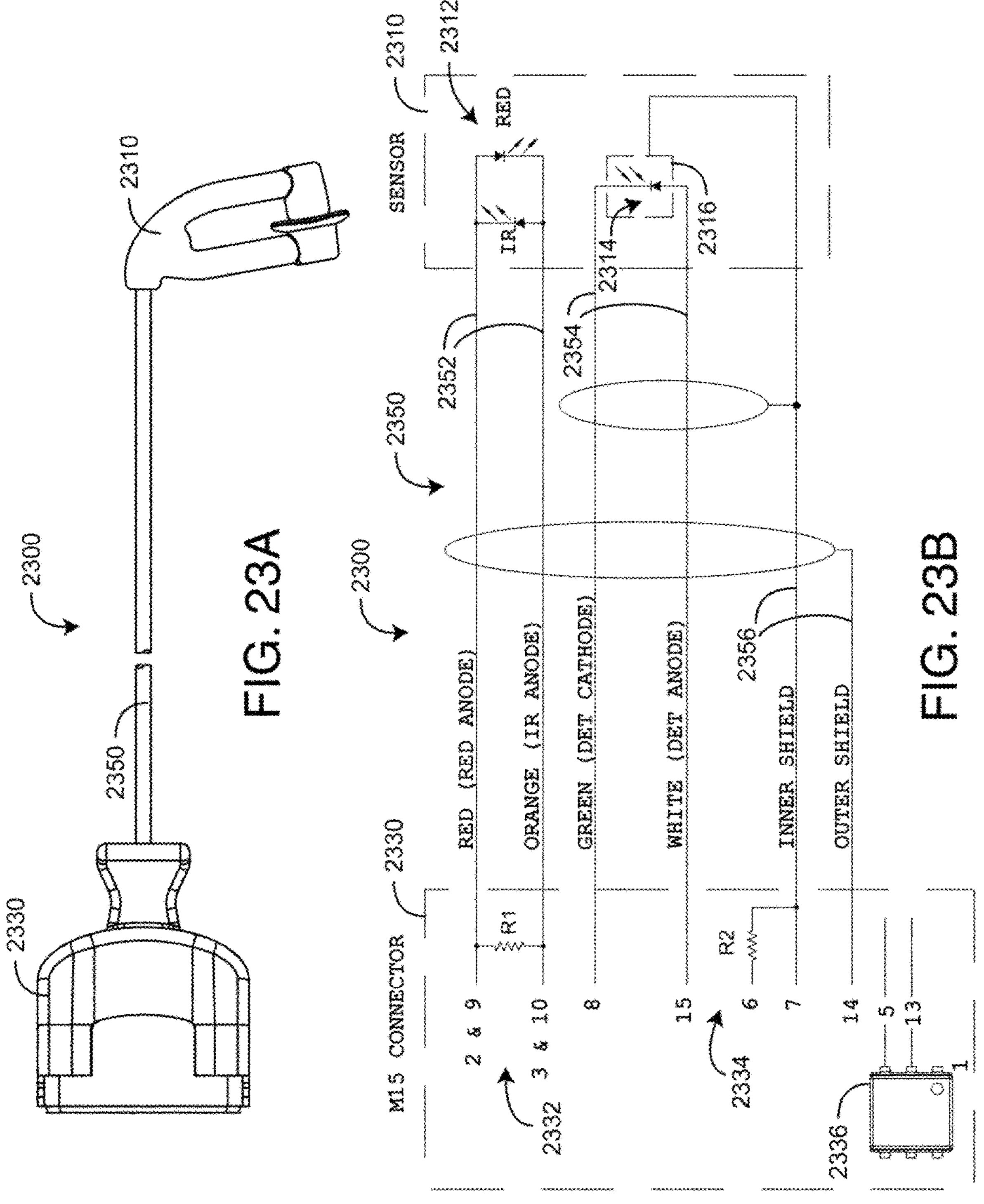

FIGS. 21A-B, 22A-B, 23A-B further illustrate concha-clip sensor embodiments 2100, 2200, 2300 having a DB9 connector 2130 (FIGS. 21A-B), a MC8 connector 2230 (FIGS. 22A-B) or a M15 connector 2330 (FIGS. 23A-B). The sensor bodies 2110, 2220, 2330 have red and IR emitters 2112, 2212, 2312 and detectors 2114, 2214, 2314 in communication with connectors 2130, 2230, 2330 via emitter wires 2152, 2252, 2352 and detector wires 2154, 2254, 2354. Sensor ID resistors 2132, 2232, 2332 are mounted in parallel with the emitters, and can be read by a monitor generating currents below the emitter-on thresholds. Compatibility resistors 2134, 2334 can be read by other monitor types. EEPROMs 2136, 2236, 2336 programmed with various sensor information can be read by more advanced monitors. Shield wires 2156, 2256, 2356 provide conductive paths via the connectors to a common shield ground. In an embodiment, ID resistors are 12.7 KΩ, compatibility resistors are 6.81 KΩ, and EEPROMs are 1-wire, 20 Kbit memories available from Maxim Integrated Products, Inc., Sunnyvale, CA.

Figure 24A:
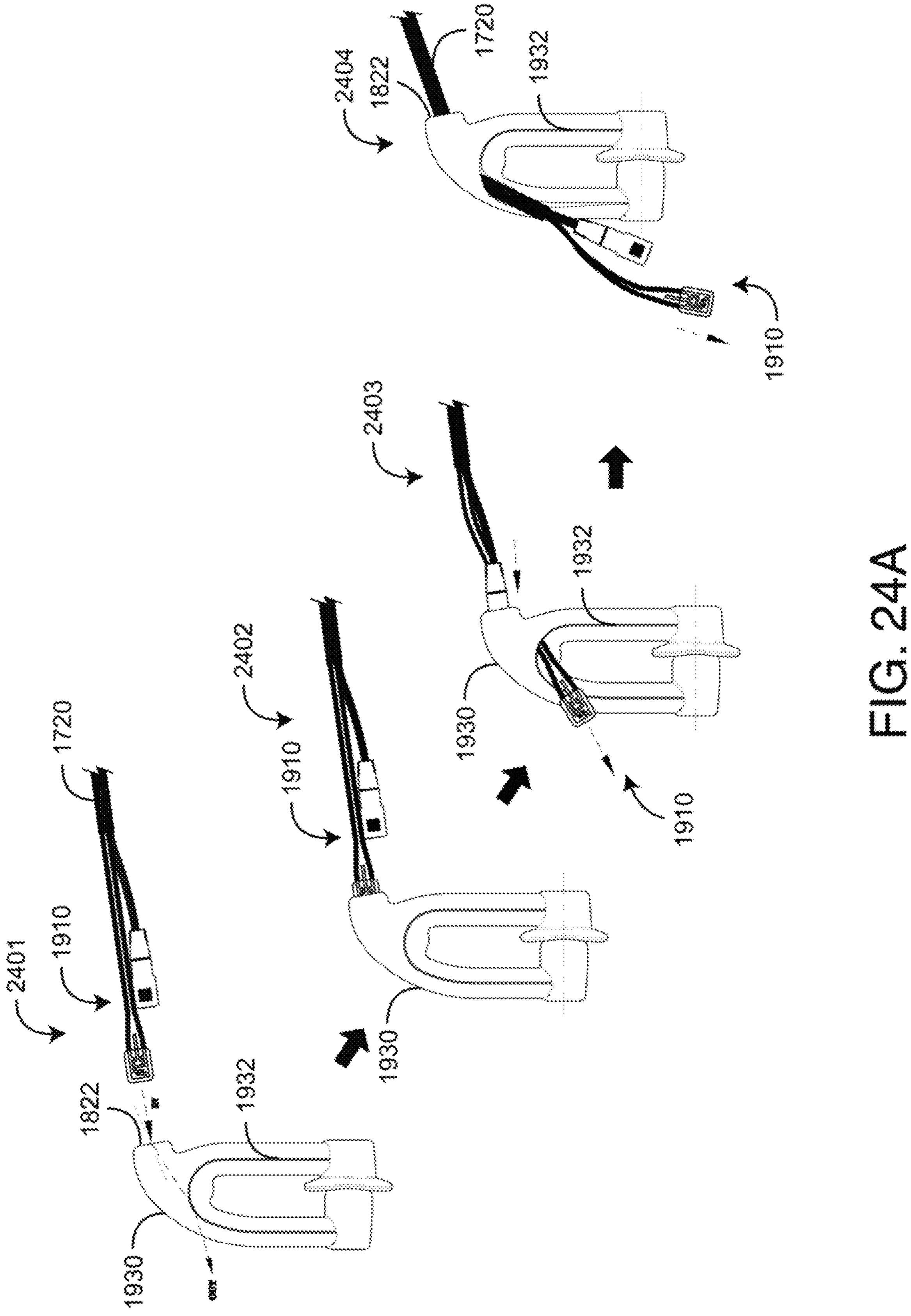
Figure 24B:
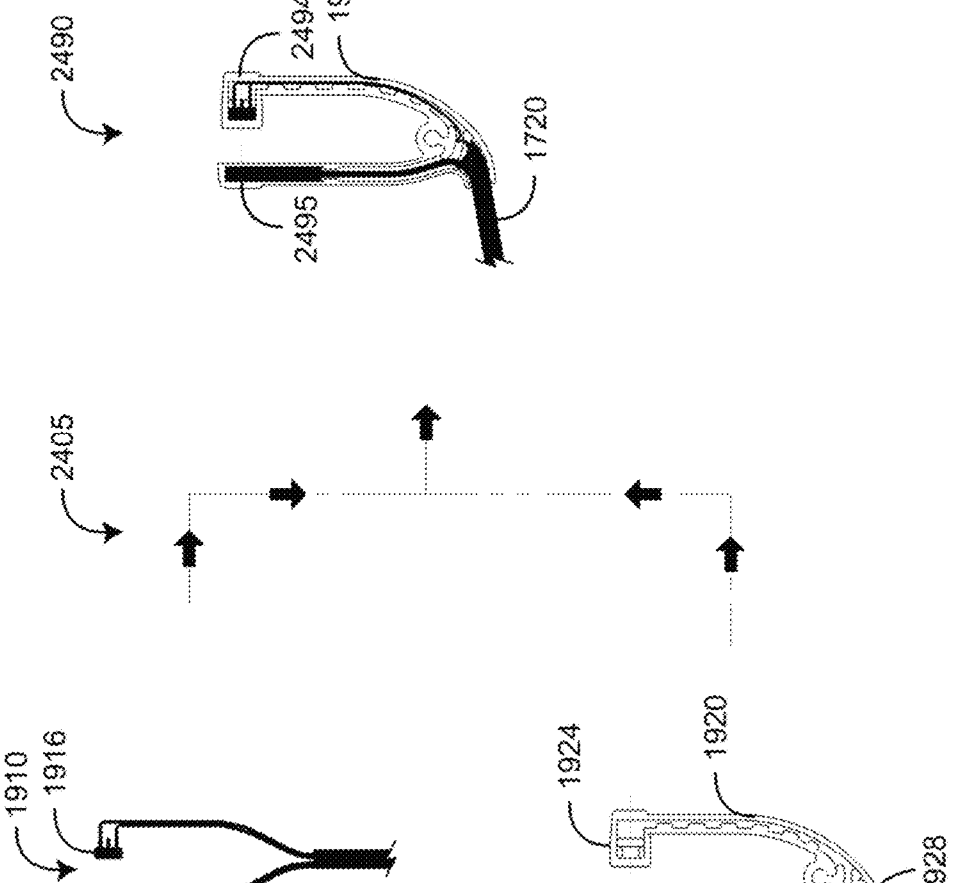
Figure 24B:
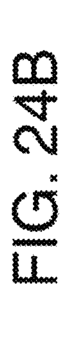
Figure 24C:
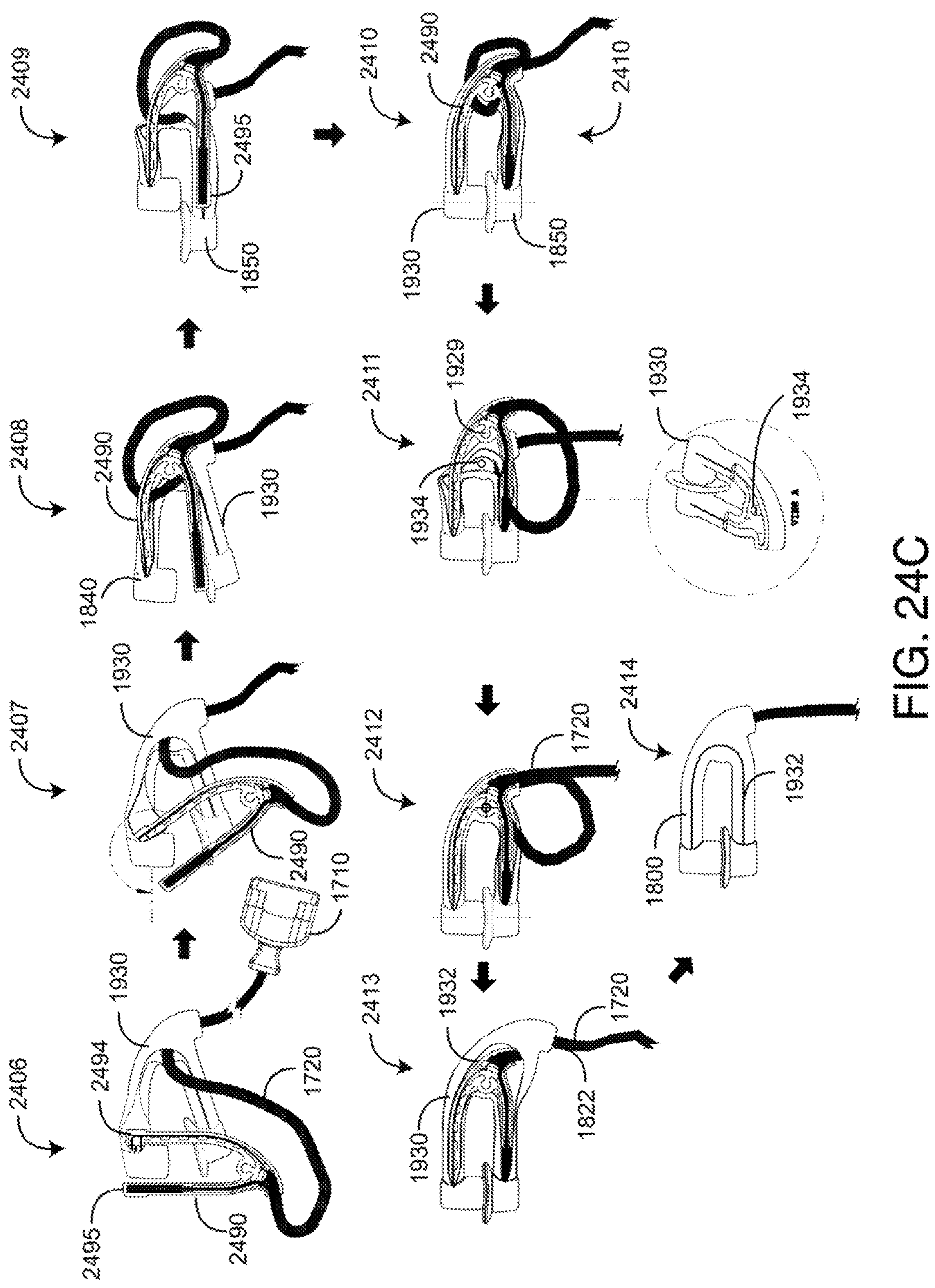
Figure 25A:
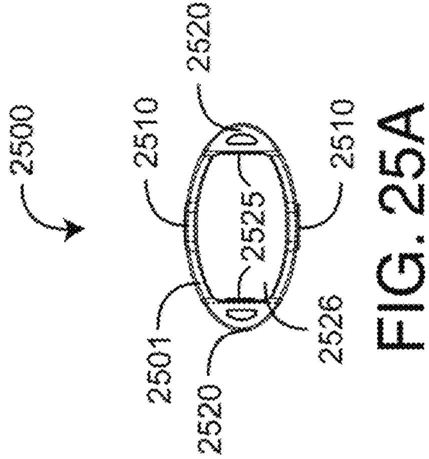
Figure 25B:
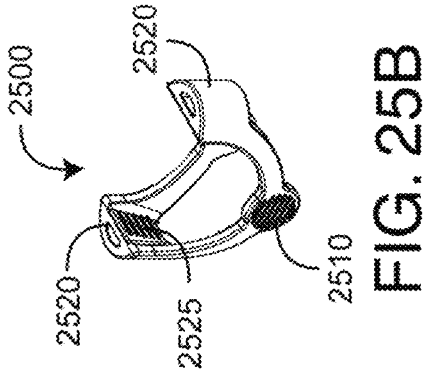
Figure 25C:
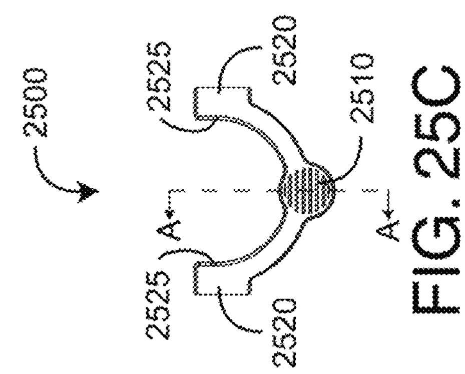
Figure 25D:
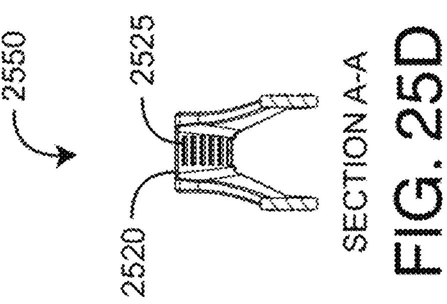
Figure 25E:
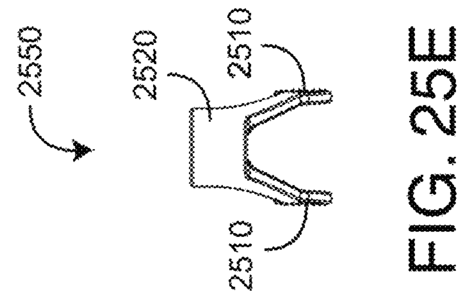
Figure 26A:
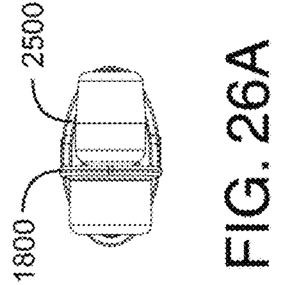
Figure 26B:
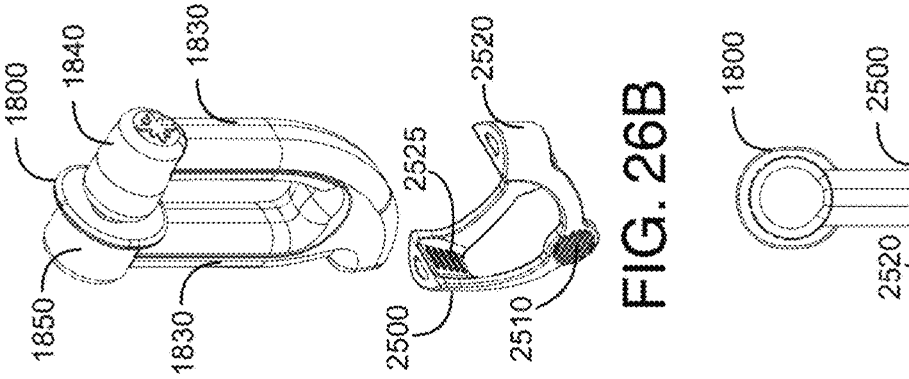
Figure 26C:
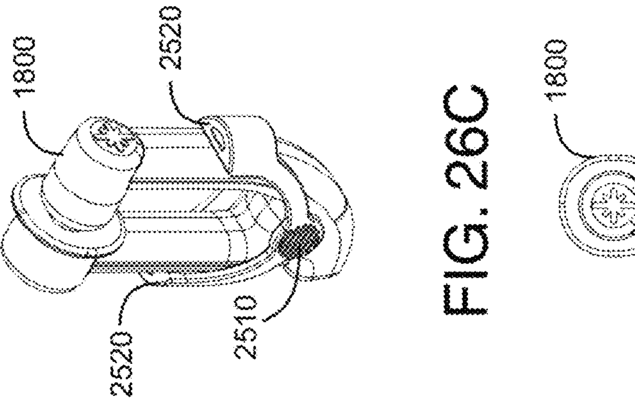
Figure 26D:
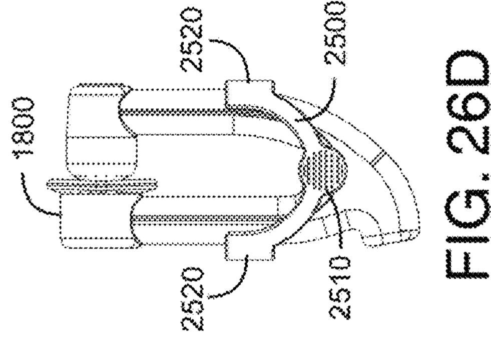
Figure 26E:
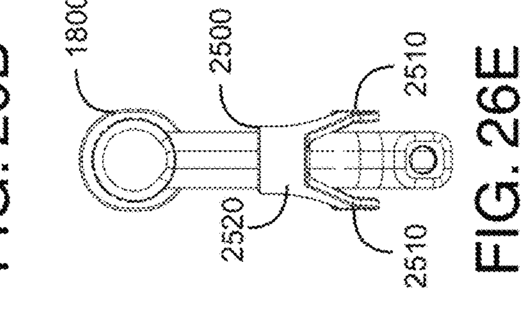
Figure 26F:
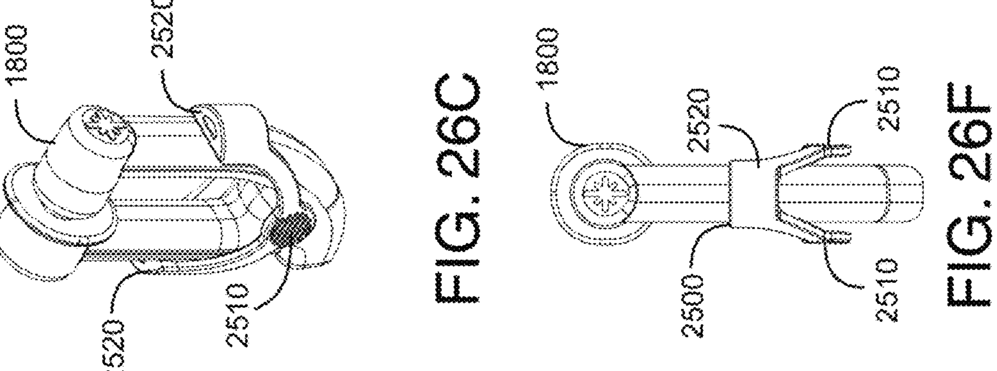
Figures 27A, 27B, 27C, 27D, 27E, 27F:
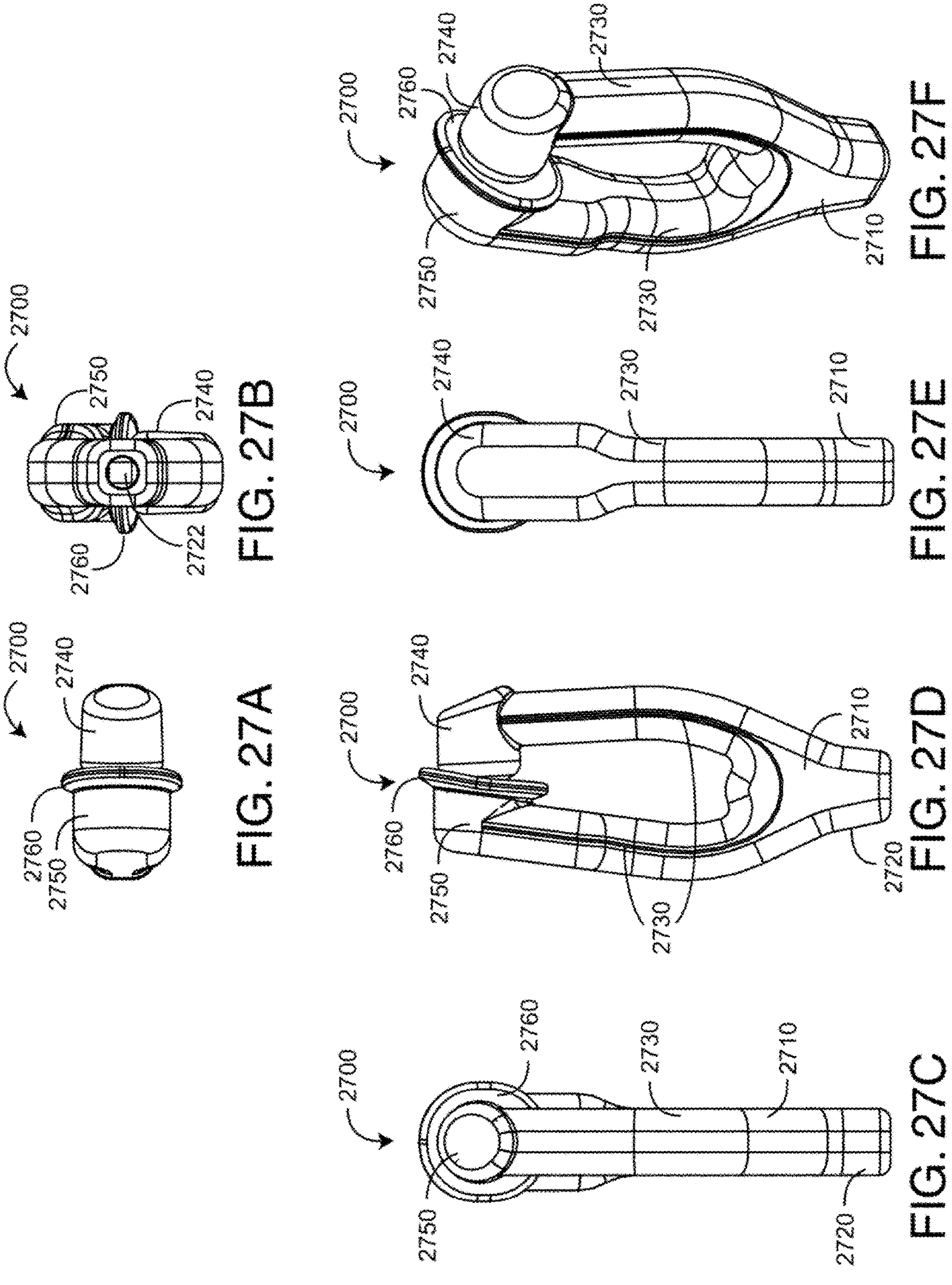

FIGS. 24A-C illustrate integration of the optical assembly 1910 disposed at the end of a sensor cable 1720, the resilient frame 1920 and the sensor housing 1930. As shown in FIG. 24A, the optical assembly 1910 is threaded into the sensor housing 1930. In particular, in a couple steps 2401-2402, the optical assembly 1910 is inserted into the sensor housing 1930 through the cable aperture 1822. In a further couple steps 2403-2404, the optical assembly 1910 and portions of the attached sensor cable 1720 are pulled through the cable aperture 1822 and out of a U-slot 1932 of the sensor housing 1930.

As shown in FIG. 24B, in a step 2405, the optical assembly 1910 is integrated with the resilient frame 1920 to form a frame assembly 2490. In particular, the detector assembly 1919 is inserted into a detector holder 1925 to form a framed detector 2495. Also, the emitter 1916 is inserted into an emitter holder 1924 to form a framed emitter 2495.

As shown in FIG. 24C, the frame assembly 2490 is integrated with the sensor housing 1930 to form the sensor body 1800. In several steps 2406-2408 the framed emitter 2494 is inserted into a pocket within the emitter housing 1840. In a couple additional steps 2409-2410, the framed detector 2495 is inserted into a pocket within the detector housing 1850. In a step 2411, a housing post 1934 is inserted into the frame hole 1929. In several additional steps 2412-2414, excess cable 1720 is removed from the sensor housing 1930 via the cable aperture 1822, and the U-slot 1932 is closed and sealed with an adhesive. The resulting sensor body 1800 is described in detail with respect to FIGS. 18A-E, above.

FIGS. 25A-E, 26A-F illustrate a force adjustment ring 2500 that slidably attaches to the sensor body 1800 so as to adjust the force of the sensor housings 1840, 1850 against concha tissue. The ring 2500 forms a generally oval opening 2526 having a pair of opposing sensor grips 2520 generally centered along a long axis of the opening 2526 and a pair of finger releases 2510 generally centered along a short axis of the opening 2526. The sensor grips 2520 have toothed faces 2525 configured to contact the sensor body legs 1830. The finger releases 2510 allow the ring to be squeezed between a finger and thumb, say, so as to compress the ring short axis, thereby lengthening the ring long axis and releasing the toothed faces 2525 from the legs 1830. In this manner, the ring 2500 can be positioned closer to or farther from the housings 1840, 1850 so as to increase or decrease the force on a concha tissue site.

FIGS. 27A-F illustrate an sensor body 2700 configured for a parallel-routed sensor cable, as compared with the sensor body 1800 (FIGS. 18A-E) configured for a perpendicular-routed sensor cable, as described above. The sensor body 2700 has a base 2710, a strain relief 2720 formed at a bottom end of the base 2710 and a pair of resilient legs 2730 extending from an opposite end of the base 2710. The strain relief 2720 has an aperture 2722 that accommodates the sensor cable 1720 (FIGS. 17A-B). An emitter housing 2740 extends from one leg 2730 and a detector housing 2750 extends from the other leg 2530. The legs 2730 accommodate cable conductors extending between a connector 1710 (FIGS. 17A-B) and an optical assembly 1910 (FIG. 19) located in the housings 2740, 2750. Each housing 2740, 2750 has an optical end having an aperture that passes light from the emitter housing 2740 to the detector housing 2750. In an embodiment, the housings 2740, 2750 fit on either side of a concha tissue site so that light is transmitted from an emitter of the optical assembly, through the concha tissue and received by a detector of the optical assembly. In an embodiment, the emitter housing 2740 fits within the ear and the detector housing outside the ear. In an embodiment, a cup 2760 extends from the optical end of the detector housing 2750. The cup 2760 has a generally circular edge and a curvature that accommodates the outside curvature of the ear. Accordingly, the cup 2760 advantageously provides a more comfortable and secure fit of the detector housing 2750 to the ear and further functions as a light shield, blocking external light sources from the detector assembly.

A sensor body 1800 (FIGS. 18A-E), 2700 (FIGS. 27A-F) is described above with respect to directly flexing resilient legs in order to space apart emitter and detector housings for placement on a concha site. In another embodiment, a pair of finger levers can extend from the legs to a position below the sensor body base opposite the resilient legs. The finger levers can be squeezed between finger and thumb so as to flex the resilient legs for concha site placement.

In a particular advantageous embodiment, a single finger lever can extend from one leg to a position below the base. This single finger lever can be squeezed using a sensor cable portion extending from the sensor body base for leverage. Such a single finger lever configuration eliminates potential discomfort from a second lever poking a patient's neck area.

An ear sensor has been disclosed in detail in connection with various embodiments. These embodiments are disclosed by way of examples only and are not to be construed as limiting the scope of the claims that follow. One of ordinary skill in art will appreciate many variations and modifications.

What is claimed is:

1. A physiological measurement device configured for placement at an ear of a user, the physiological measurement device comprising:

a body portion configured to be placed at a front portion of the user's ear proximate a concha and an ear canal of the user's ear, the body portion comprising a rounded shape and further comprising at least one emitter and at least one detector, the at least one emitter and the at least one detector of the body portion being spaced from one another and arranged in a reflective measurement configuration, wherein the at least one emitter of the body portion is configured to emit light towards a first tissue portion of the user, and wherein the at least one detector of the body portion is configured to output at least one signal responsive to detecting light reflected from said first tissue portion of the user, said at least one signal outputted by the at least one detector of the body portion indicative of at least one of pulse rate and oxygen saturation;

an ear piece portion configured to be positioned between a rear portion of the user's ear and a side of a head of the user, the ear piece portion comprising at least one emitter and at least one detector, the at least one emitter and at least one detector of the ear piece portion being spaced from one another and arranged in a reflective measurement configuration, wherein the at least one emitter of the ear piece portion is configured to emit light towards a second tissue portion of the user, and wherein the at least one detector of the ear piece portion is configured to output at least one signal responsive to detecting light reflected from said second tissue portion of the user, said at least one signal outputted by the at least one detector of the ear piece portion indicative of at least one of pulse rate and oxygen saturation;

a connecting portion comprising a first end connected to the body portion and a second end opposite the first end and connected to the ear piece portion, wherein the connecting portion and the ear piece portion cooperate to hook around a portion of the user's ear; and an ear canal portion extending from said body portion, the ear canal portion comprising a resilient material configured to facilitate securement of the ear canal portion within the user's ear canal.

2. The physiological measurement device of claim 1, further comprising a cable.

3. The physiological measurement device of claim 2, wherein the cable is configured to communicate said at least one signal outputted by the at least one detector of each of the body portion and ear piece portion to a monitoring device.

4. The physiological measurement device of claim 1, wherein the body portion is shaped to conform to a tragus of the user's ear.

5. A physiological measurement device configured for placement at an ear of a user, the physiological measurement device comprising:

a body portion configured to be placed at a front portion of the user's ear proximate a concha and an ear canal of the user's ear, the body portion comprising a rounded shape and comprising at least one emitter and at least one detector, the at least one emitter and the at least one detector being spaced from one another and arranged in a reflective measurement configuration, wherein the at least one emitter is configured to emit light towards tissue of the user, and wherein the at least one detector is configured to output at least one signal responsive to detecting light reflected from said tissue of the user, said at least one signal outputted by the at least one detector indicative of at least one physiological parameter;

an ear piece portion configured to be positioned between a rear portion of the user's ear and a side of a head of the user;

a connecting portion comprising a first end connected to the body portion and a second end opposite the first end and connected to the ear piece portion, wherein the connecting portion and the ear piece portion cooperate to hook around a portion of the user's ear; and an ear canal portion extending from said body portion, the ear canal portion comprising a resilient material configured to facilitate securement of the ear canal portion within the user's ear canal.

6. The physiological measurement device of claim 5, further comprising a cable.

7. The physiological measurement device of claim 6, wherein the cable is configured to communicate said at least one signal outputted by the at least one detector to a monitoring device.

8. The physiological measurement device of claim 6, wherein said cable extends from the ear piece portion.

9. The physiological measurement device of claim 5, wherein the body portion is shaped to conform to a tragus of the user's ear.

10. The physiological measurement device of claim 5, wherein:

the at least one emitter of the body portion is configured to emit light towards a first tissue portion of the user, and the at least one detector of the body portion is configured to output said at least one signal responsive to detecting light reflected from said first tissue portion of the user; and the ear piece portion comprises at least one emitter and at least one detector spaced from one another and arranged in a reflective measurement configuration, wherein the at least one emitter of the ear piece portion is configured to emit light towards a second tissue portion of the user, and wherein the at least one detector of the ear piece portion is configured to output at least one signal responsive to detecting light reflected from said second tissue portion of the user, said at least one signal outputted by the at least one detector of the ear piece portion indicative of at least one physiological parameter.

11. The physiological measurement device of claim 5, wherein:

the at least one emitter of the body portion is configured to emit light towards a first tissue portion of the user, and the at least one detector of the body portion is configured to output said at least one signal responsive to detecting light reflected from said first tissue portion of the user; and the ear canal portion comprises at least one emitter and at least one detector spaced from one another and arranged in a reflective measurement configuration, wherein the at least one emitter of the ear piece portion is configured to emit light towards a second tissue portion of the user, said second tissue portion being within the user's ear canal, and wherein the at least one detector of the ear canal portion is configured to output at least one signal responsive to detecting light reflected from said second tissue portion of the user, said at least one signal outputted by the at least one detector of the ear piece portion indicative of at least one physiological parameter.

12. A physiological measurement device configured for placement at an ear of a user, the physiological measurement device comprising: a body portion configured to be placed proximate a concha and an ear canal of the user's ear, the body portion comprising at least one emitter and at least one detector, wherein the at least one emitter is configured to emit light towards tissue of the user, and wherein the at least one detector is configured to output at least one signal responsive to detecting light reflected from said tissue the user, said at least one signal outputted by the at least one detector indicative of at least one physiological parameter; an ear piece portion configured to be positioned proximate a rear portion of the user's ear; a connecting portion connected to and extending between the body portion and the ear piece portion, wherein the connecting portion and the ear piece portion are configured to hook around a portion of the user's ear; and an ear canal portion extending from said body portion and configured to facilitate securement of the ear canal portion within the user's ear canal, wherein the at least one emitter of the body portion is configured to emit light towards a first tissue portion of the user, and the at least one detector of the body portion is configured to output said at least one signal responsive to detecting light reflected from said first tissue portion of the user; and the ear canal portion comprises at least one emitter and at least one detector spaced from one another and arranged in a reflective measurement configuration, wherein the at least one emitter of the ear piece portion is configured to emit light towards a second tissue portion of the user, said second tissue portion being within the user's ear canal, and wherein the at least one detector of the ear canal portion is configured to output at least one signal responsive to detecting light reflected from said second tissue portion of the user, said at least one signal outputted by the at least one detector of the ear piece portion indicative of at least one physiological parameter.

13. The physiological measurement device of claim 12, further comprising a cable.

14. The physiological measurement device of claim 13, wherein the cable is configured to communicate said at least one signal outputted by the at least one detector of the ear piece portion to a monitoring device.

15. The physiological measurement device of claim 12, wherein the body portion is shaped to conform to a tragus of the user's ear.

16. The physiological measurement device of claim 12, wherein said at least one physiological parameter comprises at least one of pulse rate and oxygen saturation.

17. The physiological measurement device of claim 12, wherein the ear canal portion comprises a resilient material configured to facilitate securement of the ear canal portion within the user's ear canal.

* * * * *